(12) United States Patent
Schwede et al.

(10) Patent No.: US 7,842,809 B2
(45) Date of Patent: Nov. 30, 2010

(54) PYRAZOLOPYRIDINES AND SALTS THEREOF, A PHARMACEUTICAL COMPOSITION COMPRISING SAID COMPOUNDS, A METHOD OF PREPARING SAME AND USE OF SAME

(75) Inventors: Wolfgang Schwede, Glienicke (DE); Hans Briem, Bremen (DE); Hermann Kuenzer, Berlin (DE); Manfred Husemann, Hohen Neuendorf (DE); Georg Kettschau, Berlin (DE); Martina Schaefer, Berlin (DE); Antonius Ter Laak, Berlin (DE); Karl-Heinz Thierauch, Berlin (DE); Stuart James Ince, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 1298 days.

(21) Appl. No.: 11/337,114

(22) Filed: Jan. 23, 2006

(65) Prior Publication Data
US 2006/0252754 A1    Nov. 9, 2006

Related U.S. Application Data

(60) Provisional application No. 60/647,407, filed on Jan. 28, 2005.

(30) Foreign Application Priority Data

Jan. 24, 2005    (EP) .................................. 05075177

(51) Int. Cl.
*C07D 513/02*    (2006.01)
(52) U.S. Cl. ..................................... 546/119
(58) Field of Classification Search ................. 546/119; 548/360.5
See application file for complete search history.

(56) References Cited

U.S. PATENT DOCUMENTS 7,297,709 B2    11/2007    Dai et al.
7,323,472 B2    1/2008    Adams et al.

FOREIGN PATENT DOCUMENTS

WO    WO 0119828 A2    3/2001
WO    WO 2004113304 A1    12/2004

OTHER PUBLICATIONS

El-Semary, Mona M.A. et al., "Synthesis and Biological Evaluation of Some Pyridine Derivatives as Potential Cardiotonic Agents," Alexandria Journal of Pharmaceutical Sciences, 2003, pp. 59-63, vol. 17, No. 1, XP008062291.
Abdalla, M. et al., "Synthesis and Reaction of 3-Cyano 2-(1H)-Pyridones," Pakistan J. Ind. Res., 1977, pp. 139-149, vol. 20, No. 3, XP008062289.
Elneairy M. A. A., "Cyanothioacetamide in Heterocyclic Synthesis . . . " Phosphorus, Sulfur and Silicon and the Related Elements, Gordon and Breach Science publishers, Amsterdam, GB, 2003, pp. 2201-2214, vol. 178, No. 10, XP008040312.

*Primary Examiner*—Janet L. Andres
*Assistant Examiner*—David E. Gallis
(74) *Attorney, Agent, or Firm*—Millen, White, Zelano & Branigan, P.C.

(57) ABSTRACT

The invention relates to pyrazolopyridines according to the general formula (I):

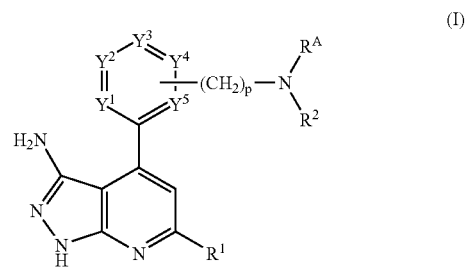

and salts thereof, to pharmaceutical compositions comprising said pyrazolopyridines and to a method of preparing said pyrazolopyridines as well as the use thereof for manufacturing a pharmaceutical composition for the treatment of diseases of dysregulated vascular growth or of diseases which are accompanied with dysregulated vascular growth, wherein the compounds effectively interfere with angiopoietin and therefore influence Tie2 signalling.

25 Claims, 1 Drawing Sheet

PYRAZOLOPYRIDINES AND SALTS THEREOF, A PHARMACEUTICAL COMPOSITION COMPRISING SAID COMPOUNDS, A METHOD OF PREPARING SAME AND USE OF SAME

This application claims the benefit of the filing date of U.S. Provisional Application Ser. No. 60/647,407 filed Jan. 28, 2005 which is incorporated by reference herein.

The invention relates to pyrazolopyridine compounds of general formula (I) and salts thereof, to pharmaceutical compositions comprising said pyrazolopyridine compounds, to methods of preparing said pyrazolopyridines as well as to the use thereof.

In order to defeat diseases with dysregulated vascular growth such as cancer different strategies were developed. One possible strategy is the blockade of angiogenesis to the tumour tissue, because tumour angiogenesis is a prerequisite for the growth of solid tumours.

The angiogenesis represents beside the vasculogenesis one of two basic processes during the genesis of vasculature. Vasculogensis names the neoplasm of vascular tissue during the embryo development, wherein the angiogenesis describes the neoplasm of vasculature by sprouts or division of present vasculature. It has been found that two receptors expressed on endothelial cells, VEGF- (vascular endothelial growth factor) and Tie-receptors (also called Tek), are essential for normal development of vasculature as blood vessels (Dumont et al.: "Dominant-negative and targeted null mutations in the endothelial receptor tyrosine kinase Tie-2 reveal a critical role in vasculogenesis of the embryo" *Genes Dev.* 1994, 8:1897-909; Sato et al.: "Distinct roles of the receptor tyrosine kinases Tie-1 and Tie-2 in blood vessel formation" *Nature.* 1995, Jul. 6; 376(6535):70-4.).

The mechanism of Tie2 signalling was characterized by different researchers, wherein different angiopoietins were found to be involved. So it could be explained that angiopoietin-1 if bound to the extracellular domain of the Tie2-receptor stimulates autophosphorylation and activates the intracellular kinase domain. Angiopoietin-1 activation of Tie2, however, does not stimulate mitogenesis but rather migration. Angiopoietin-2 can block angiopoietin-1 mediated Tie2 activation and the resulting endothelial migration. This indicates that angiopoietin-2 is a naturally occurring inhibitor of Tie2 activation (Maisonpierre et al.: "Angiopoietin-2, a natural antagonist for Tie2 that disrupts in vivo angiogenesis". Science. 1997, Jul. 4; 277(5322):55-60; Witzenbichler et al.: "Chemotactic properties of angiopoietin-1 and -2, ligands for the endothelial-specific receptor tyrosine kinase Tie2". *J Biol. Chem.* 1998, Jul. 17; 273(29):18514-21). For an overview see FIG. 1 modified by Peters et al. (Peters et al.: "Functional significance of Tie2 signalling in the adult vasculature". *Recent Pros Horm Res.* 2004; 59:51-71. Review.).

Receptor dimerization results in cross-phosphorylation on specific tyrosine-residues. Receptor cross-phosphorylation has a dual effect: it enhances the receptor's kinase activity and it provides binding sites for signalling molecules possessing phosphotyrosine binding domains (SH2 and PTB domains) (Pawson T.: "Regulation and targets of receptor tyrosine kinases". *Eur J Cancer.* 2002, September, 38 Suppl 5:S3-10. Review).

The signalling cross-talk between the PI3-K pathway and the Dok-R pathway is required for an optimal chemotactic response downstream of Tie2. Other recent studies have shown that Tie2-mediated activation of the PI3-K/Akt pathway is required for endothelial nitric oxide synthase (eNOS) activation, focal adhesion kinase activation, and protease secretion, all of which may contribute importantly to Tie2 function during angiogenesis (Kim I. et al.: "Angiopoietin-1 regulates endothelial cell survival through the phosphatidylinositol 3'-Kinase/Akt signal transduction pathway". *Circ Res.* 2000, Jan. 7-21; 86(1):24-9; Babaei et al.: "Angiogenic actions of angiopoietin-1 require endothelium-derived nitric oxide". *Am J Pathol.* 2003, June; 162(6):1927-36).

For normal development a balanced interaction between the receptors and so-called ligands is necessary. Especially the angiopoietins, which signal via Tie2 receptors, play an important role in angiogenesis (Babaei et al., 2003).

The broad expression of Tie2 in adult vasculature has been confirmed in transgenic mice using Tie2 promoter driven reporters (Schlaeger et al.: "Uniform vascular-endothelial-cell-specific gene expression in both embryonic and adult transgenic mice". *Proc Natl Acad Sci U S A.* 1997, Apr. 1; 94(7):3058-63; Motoike et al.: "Universal GFP reporter for the study of vascular development". *Genesis.* 2000, October; 28(2):75-81). Immunohistochemical analysis demonstrated the expression of Tie2 in adult rat tissues undergoing angiogenesis. During ovarian folliculogenesis, Tie2 was expressed in the neo-vessels of the developing corpus luteum. Angiopoietin-1 and angiopoietin-2 also were expressed in the corpus luteum, with angiopoietin-2 localizing to the leading edge of proliferating vessels and angiopoietin-1 localizing diffusely behind the leading edge (Maisonpierre et al., 1997). It was suggested that angiopoietin-2-mediated inhibition of Tie2 activation serves to "destabilize" the vessel, to make it responsive to other angiogenic growth factors such as VEGF. Subsequently, angiopoietin-1-mediated activation of Tie2 would trigger stabilization of the neovasculature.

The disruption of Tie2 function shows the relevance of Tie2 for neoangiogenesis in transgenic mice resulting in early embryonic lethality as a consequence of vascular abnormalities (Dumont et al., 1994; Sato et al., 1995). Tie2−/− embryos failed to develop the normal vessel hierarchy, suggestive of a failure of vascular branching and differentiation. Tie2−/− embryos have a decreased number of endothelial cells and furthermore less contact between endothelial cells and the underlying pericytes/smooth muscle cells. This implies a role in the maturation and stabilization of newly formed vasculature.

The studies in mice with transgenic or ablated Tie2 gene suggest a critical role for Tie2 in maturation of vascular development in embryos and in adult vasculature. Conditional expression of Tie2 in the endothelium of mice homozygous for a Tie2 null allele partially rescued the embryonic lethality of the Tie2 null phenotype (Jones et al., "Tie receptors: new modulators of angiogenic and lymphangiogenic responses", Nat Rev Mol Cell Biol. 2001 April; 2(4):257-67. Review). Mice lacking functional angiopoietin-1 expression and mice overexpressing angiopoietin-2 both displayed a phenotype similar to Tie2−/− mice (Suri et al., "Requisite role of angiopoietin-1, a ligand for the Tie2 receptor, during embryonic angiogenesis.", Cell. 1996 December 27; 87(7): 1171-80; Maisonpierre et al., "Angiopoietin-2, a natural antagonist for Tie2 that disrupts in vivo angiogenesis.", Science, 1997 Jul. 4; 277(5322):55-60).

Angiopoietin-2 −/− mice have profound defects in the growth and patterning of lymphatic vasculature and fail to remodel and regress the hyaloid vascutature of the neonatal tens (Gale et al.: "Angiopoietin 2 is required for postnatal angiogenesis and lymphatic patterning, and only the latter role is rescued by Angiopoietin-1 ". *Dev Cell.* 2002, September; 3(3):411-23). Angiopoietin-1 rescued the lymphatic defects, but not the vascular remodeling defects. So angiopoietin-2 might function as a Tie2 antagonist in blood vasculature but as a Tie2 agonist in developing lymph vasculature.

Tie2 also plays a role in pathological angiogenesis. It was shown that mutations in Tie2 that cause inherited venous malformations and enhance both ligand dependent and independent Tie2 kinase activity (Vikkula et al.: "Dysmorphogenesis caused by an activating mutation in the receptor tyrosine kinase Tie2". Cell. 1996, Dec. 27; 87(7):1181-90). Tie2 expression was investigated in human breast cancer tumour specimens and Tie2 expression was found in the vascular endothelium both in normal breast tissue and in breast tumours. The proportion of Tie2-positive tumour microvessels was increased in tumours as compared to normal breast tissue (Peters et al., "Expression of Tie2/Tek in breast tumour vasculature provides a new marker for evaluation of tumour angiogenesis.", Br J Cancer. 1998; 77(1):51-6).

Angiopoietin-1 overexpression in tumour models resulted in decreased tumour growth. The effect is possibly related to angiopoietin-1 mediated stabilization of the tumour vasculature, which renders the vessels resistant to angiogenic stimuli (Hayes et al.: "Expression and function of angiopoietin-1 in breast cancer". Br J Cancer. 2000, November; 83(9):1154-60; Shim et al.: "Inhibition of angiopoietin-1 expression in tumour cells by an antisense RNA approach inhibited xenograft tumour growth in immunodeficient mice". Int J Cancer. 2001, Oct. 1; 94(1):6-15; Shim et al.: "Angiopoietin 1 promotes tumour angiogenesis and tumour vessel plasticity of human cervical cancer in mice". Exp Cell Res. 2002, Oct. 1; 279(2):299-309; Hawighorst et al.: "Activation of the tie2 receptor by angiopoietin-1 enhances tumour vessel maturation and impairs squamous cell carcinoma growth". Am J Pathol. 2002, April; 160(4):1381-92.; Stoeltzing et al.: "Angiopoietin-1 inhibits vascular permeability, angiogenesis, and growth of hepatic colon cancer tumours". Cancer Res. 2003, Jun. 15; 63(12):3370-7.).

Corneal angiogenesis induced by tumour cell conditioned medium was inhibited by recombinant sTie, despite the presence of VEGF. Mammary tumour growth was significantly inhibited in a skin chamber tumour model recombinant sTie2 (Lin et al.: "Inhibition of tumour angiogenesis using a soluble receptor establishes a role for Tie2 in pathologic vascular growth". J Clin Invest. 1997, Oct. 15; 100(8):2072-8; Lin et al.: "Antiangiogenic gene therapy targeting the endothelium-specific receptor tyrosine kinase Tie2". Proc Natl Acad Sci USA. 1998, Jul. 21; 95(15):8829-34). Similar sTie constructs have shown comparable effects in different tumour models (Siemeister et al.: "Two independent mechanisms essential for tumour angiogenesis: inhibition of human melanoma xenograft growth by interfering with either the vascular endothelial growth factor receptor pathway or the Tie-2 pathway". Cancer Res. 1999, Jul. 1; 59(13):3185-91; Stratmann et al.: "Differential inhibition of tumour angiogenesis by tie2 and vascular endothelial growth factor receptor-2 dominant-negative receptor mutants". Int J Cancer. 2001, Feb. 1; 91(3): 273-82; Tanaka et al.: "Tie2 vascular endothelial receptor expression and function in hepatocellular carcinoma". Hepatology. 2002, April; 35(4):861-7).

When the interaction of angiopoietin-2 with its receptor is blocked by application of a neutralizing anti-angiopoietin-2 monoclonal antibody, the growth of experimental tumours can be blocked efficiently again pointing to the important role of Tie2 in tumour angiogenesis and growth (Oliner et al.: "Suppression of angiogenesis and tumour growth by selective inhibition of angiopoietin-2". Cancer Cell. 2004, November; 6(5):507-16.) So inhibiting the Tie2 pathway will inhibit pathological angiogenesis.

To influence the interaction between receptor and ligand it could be shown that angiogenesis may be blocked with blockers such as Avastin which interfere with VEGF signal transduction to endothelial cells.

Avastin is a clinically effective antibody that functions as tumour growth inhibitor by blockade of VEGFR mediated angiogenic signalling. Thus interference with VEGF signalling is a proven clinical principle. VEGF-C is a molecule inducing lymph angiogenesis via VEGFR 3. The blockade of this signal pathway is inhibiting diseases associated with lymph angiogenesis as is lymphoedema and related diseases (Saharinen et al.: "Lymphatic vascutature: development, molecular regulation and role in tumour metastasis and inflammation." Trends Immunol. 2004, Jul.: 25(7): 387-95. Review).

Pyrazolopyridines have been disclosed as antimicrobiotic substances (e.g. Attaby et al., Phosphorus, Sulfur and Silicon and the related Elements (1999), 149, 49-64; ibid. (1999), 155, 253-270).

U.S. Pat. No. 5,478,830 further discloses fused heterocycles for the treatment of atherosclerosis.

WO 01/19828 discloses 125 templates, including pyrazolopyridines, as modulators of the activity of receptor and non-receptor tyrosine and serine/threonine kinases.

WO 04/113304 discloses indazoles, benzisoxazoles and benzisothiazoles as inhibitors of protein tyrosine kinases.

There is a high demand for active compounds which can be used as inhibitors of Tie2 and/or VEGFR-2 and in the treatment of diseases of dysregulated vascular growth or diseases which are accompanied with dysregulated vascular growth, in particular solid tumours and metastases thereof. However, it would be desirable to have compounds at one's disposal which display more selective inhibition of appropriate kinases, such as Tie2. More particularly it would be desirable to have compounds which display a stronger inhibition of both Tie-2 and VEGF-R2, wherein the respective inhibition of either Tie2 or VEGFR-2 can be tuned according to the appropriate therapeutic needs.

Surprisingly, compounds of the present invention display a more selective inhibition of Tie-2 compared with other kinases. Even more surprisingly appropriate modifications produce compounds which display a stronger inhibition of both Tie-2 and VEGF-R2, wherein the respective inhibition of either Tie2 or VEGFR-2 can be tuned according to the appropriate therapeutic needs. Such pharmacological profiles are highly desirable not only for treating diseases of dysregulated vascular growth or diseases which are accompanied with dysregulated vascular growth, in particular solid tumours and metastases thereof, but for treating non-oncological diseases of dysregulated vascular growth or non-oncological diseases which are accompanied with dysregulated vascular growth, such as retinopathy, other angiogenesis dependent diseases of the eye, in particular cornea transplant rejection or age-related macular degeneration, rheumatoid arthritis, and other inflammatory diseases associated with angiogenesis, in particular psoriasis, delayed type hypersensitivity, contact dermatitis, asthma, multiple sclerosis, restenosis, pulmonary hypertension, stroke, and diseases of the bowel, diseases such as coronary and peripheral artery disease, wherein treatment of the said non-oncological diseases are preferably accomplished with less side-effects than in the treatment of oncological diseases.

The solution to the above-mentioned novel technical problem is achieved by providing compounds derived, in accordance with the present invention, from a class of pyrazolopyridines and salts thereof, methods of preparing pyrazolopyridines, a pharmaceutical composition containing said pyrazolopyridines, use of said pyrazolopyridines and a method for treating diseases with said pyrazolopyridines, all in accordance with the description, as defined in the claims of the present Application.

The invention thus relates to compounds of general formula (I):

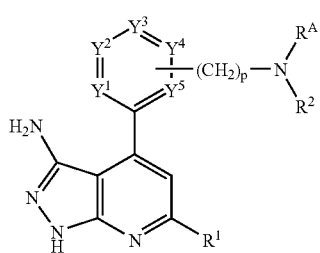

wherein:

R$^1$ stands for C$_1$-C$_6$-alkyl, C$_2$-C$_6$-alkenyl, C$_2$-C$_6$-alkynyl, C$_3$-C$_{10}$-cycloalkyl, C$_3$-C$_{10}$-heterocycloalkyl, aryl or heteroaryl optionally being substituted one or more times, the same way or differently with K, whereby C$_3$-C$_{10}$-heterocycloalkyl itself must at least once be interrupted by an atom of the group comprising, preferably consisting of, nitrogen, oxygen and/or sulfur and whereby C$_3$-C$_{10}$-cycloalkyl ring and/or C$_3$-C$_{10}$-heterocycloalkyl ring can optionally be interrupted one or more times, the same or differently with a group —C(O)—, —S(O)— or —S(O)$_2$— and whereby C$_3$-C$_{10}$-cycloalkyl ring and/or C$_3$-C$_{10}$-heterocycloalkyl ring can optionally contain one or more double bonds, K stands for halogen, hydroxy or a substituent of the group comprising, preferably consisting of, —OR$^3$ or —NR$^5$R$^6$ or for C$_3$-C$_{10}$-cycloalkyl, C$_3$-C$_{10}$-heterocycloalkyl, aryl or heteroaryl optionally being substituted one or more times, the same way or differently with L, whereby C$_3$-C$_{10}$-heterocycloalkyl itself must at least one time be interrupted by an atom of the group comprising, preferably consisting of, nitrogen, oxygen and/or sulfur and whereby C$_3$-C$_{10}$-cycloalkyl ring and/or C$_3$-C$_{10}$-heterocycloalkyl ring can optionally be interrupted one or more times, the same or differently with a group —C(O)—, —S(O)— or —S(O)$_2$— and whereby C$_3$-C$_{10}$-cycloalkyl ring and/or C$_3$-C$_{10}$-heterocycloalkyl ring can optionally contain one or more double bonds, L stands for a substituent of the group comprising, preferably consisting of, —C(O)R$^4$ or —NR$^5$R$^6$ or for C$_1$-C$_6$-alkyl optionally being substituted one or more times, the same way or differently with halogen, hydroxy, cyano, nitro or the group —NR$^5$R$^6$ or —C(O)R$^4$, R$^4$ stands for hydrogen or C$_1$-C$_6$-alkyl optionally being substituted one or more times, the same way or differently with halogen, hydroxy, cyano, nitro or the group —NR$^5$R$^6$ or —C(O)R$^4$, R$^2$ stands for a substituent of the group comprising, preferably consisting of, —C(O)—NR$^7$R$^{7a}$, —S(O)$_2$—R$^7$, —S(O)$_2$NR$^7$R$^{7a}$, —S(O)(NH)R$^7$, —C(O)R$^7$ or —C(O)OR$^7$, R$^3$ stands for C$_1$-C$_6$-alkyl, aryl or —(CH$_2$)$_n$-aryl, wherein C$_1$-C$_6$-alkyl, aryl or —(CH$_2$)$_n$-aryl can optionally be substituted one or more times, the same way or differently with C$_1$-C$_6$-alkyl, C$_1$-C$_6$-alkoxy, halogen, hydroxy, cyano, nitro or the group —NR$^5$R$^6$ or —C(O)R$^4$, R$^4$ stands for hydrogen, hydroxy, C$_1$-C$_6$-alkyl, C$_1$-C$_6$-haloalkyl, C$_1$-C$_6$-alkoxy or the group —NR$^5$R$^6$, R$^5$ and R$^6$ independently from one another stand for hydrogen, C$_1$-C$_6$-alkyl, aryl, —(CH$_2$)$_n$-aryl, or for a group —C(O)R$^4$, wherein C$_1$-C$_6$-alkyl or aryl can optionally be substituted one or more times, the same way or differently with halogen, hydroxy, cyano, nitro or the group —NR$^7$R$^{7a}$ or —C(O)R$^4$, or R$^5$ and R$^6$ together with the nitrogen atom to which they are attached, form a 3 to 10 membered heterocycloalkyl ring, whereby heterocycloalkyl ring itself must at least one time be interrupted by an atom of the group comprising, preferably consisting of, nitrogen, oxygen and/or sulfur and can optionally be interrupted one or more times, the same way or differently with a group —C(O)—, —S(O)— and/or —S(O)$_2$— and can optionally contain one or more double bonds, R$^7$ and R$^{7a}$ independently from one another stand for hydrogen, C$_1$-C$_6$-alkyl C$_3$-C$_{10}$-cycloalkyl, C$_3$-C$_{10}$-heterocycloalkyl, aryl or heteroaryl, wherein C$_1$-C$_6$-alkyl, C$_3$-C$_{10}$-cycloalkyl, C$_3$-C$_{10}$-heterocycloalkyl, aryl or heteroaryl can optionally be substituted one or more times, the same way or differently with M, whereby C$_3$-C$_{10}$-heterocycloalkyl itself must at least one time be interrupted by an atom of the group comprising, preferably consisting of, nitrogen, oxygen and/or sulfur and whereby C$_3$-C$_{10}$-cycloalkyl ring and/or C$_3$-C$_{10}$-heterocycloalkyl ring can optionally be interrupted one or more times, the same way or differently with a group —C(O)—, —S(O)— or —S(O)$_2$— and whereby C$_3$-C$_{10}$-cycloalkyl ring and/or C$_3$-C$_{10}$-heterocycloalkyl ring can optionally contain one or more double bonds, or R$^7$ and R$^{7a}$ together with the nitrogen atom to which they are attached, form a 3 to 10 membered heterocycloalkyl ring, whereby heterocycloalkyl ring itself must at least one time be interrupted by an atom of the group comprising, preferably consisting of, nitrogen, oxygen and/or sulfur and can optionally be interrupted one or more times, the same way or differently with a group —C(O)—, —S(O)— or —S(O)$_2$— and can optionally contain one or more double bonds, M stands for a substituent of the group comprising, preferably consisting of, cyano, halogen, hydroxy, nitro or for C$_1$-C$_6$-alkyl, C$_2$-C$_6$-alkenyl, C$_2$-C$_6$-alkynyl, C$_1$-C$_6$-alkoxy, C$_1$-C$_6$-haloalkoxy, C$_1$-C$_6$-haloalkyl, aryl, C$_3$-C$_{10}$-heteroaryl, —(CH$_2$)$_m$-phenyl or —(CH$_2$)$_m$—O—(CH$_2$)$_q$phenyl, wherein C$_1$-C$_6$-alkyl, C$_2$-C$_6$-alkenyl, C$_2$-C$_6$-alkynyl, C$_1$-C$_6$-alkoxy, aryl, C$_3$-C$_{10}$-heteroaryl, —(CH$_2$)$_m$-phenyl or —(CH$_2$)$_m$—O—(CH$_2$)$_q$phenyl can optionally be substituted one or more times, the same way or differently with a substituent of the group comprising, preferably consisting of, amino, cyano, halogen, hydroxy, nitro, C$_1$-C$_6$-alkyl, C$_1$-C$_6$-alkoxy, C$_1$-C$_6$-haloalkoxy, C$_1$-C$_6$-haloalkyl, —(CH$_2$)$_m$-phenyl or —(CH$_2$)$_m$—O—(CH$_2$)$_q$phenyl,

Y$^1$, Y$^2$, Y$^3$,

Y$^4$ and Y$^5$ independently from each other stand for —CH═, —CZ═ or —N═ and —N═ can stand 0, 1, 2, or 3 times as a ring atom, z stands for cyano, nitro, halogen, hydroxy or a substituent of the group comprising, preferably consisting of, —NR$^5$R$^6$, —OR$^3$, —C(O)R$^7$, —C(O)OR$^7$, —C(O)NR$^7$R$^{7a}$, —S(O) R$^7$ or —S(O)$_2$R$^7$ or for C$_1$-C$_6$-alkyl, C$_2$-C$_6$-alkenyl, C$_2$-C$_6$-alkynyl or C$_3$-C$_{10}$-cycloalkyl, whereby C$_1$-C$_6$-alkyl, C$_2$-C$_6$-alkenyl, C$_2$-C$_6$-alkynyl or C$_3$-C$_{10}$-cycloalkyl can optionally be substituted one or more times, the same way or different with cyano, nitro, halogen, hydroxy, —OR$^3$ or —NR$^5$R$^6$, m stands for an integer of 0, 1, 2, 3, or 4,
n stands for an integer of 0, 1, 2, 3, or 4,
p stands for an integer of 0, 1, 2, 3, or 4, and
q stands for an integer of 0, 1, 2, 3, or 4, as well as:

N-oxides, solvates, hydrates, isomers, diastereomers, enantiomers and salts thereof, which are effective inhibitors of Tie2 kinase.

The terms as mentioned hereinbelow and in the claims have preferably the following meanings:

The term "alkyl" is to be understood as preferably meaning branched and unbranched alkyl, meaning e.g. methyl, ethyl, n-propyl, iso-propyl, n-butyl, iso-butyl, tert-butyl, sec-butyl, pentyl, iso-pentyl, hexyl, heptyl, octyl, nonyl and decyl and the isomers thereof.

The term "alkoxy" is to be understood as preferably meaning branched and unbranched alkoxy, meaning e.g. methoxy, ethoxy, propyloxy, iso-propyloxy, butyloxy, iso-butyloxy, tert-butyloxy, sec-butyloxy, pentyloxy, iso-pentyloxy, hexyloxy, heptyloxy, octyloxy, nonyloxy, decyloxy, undecyloxy and dodecyloxy and the isomers thereof.

The term "haloalkoxy" is to be understood as preferably meaning branched and unbranched alkoxy, meaning e.g. methoxy, ethoxy, propyloxy, iso-propyloxy, butyloxy, iso-butyloxy, tert-butyloxy, sec-butyloxy, pentyloxy, iso-pentyloxy, hexyloxy, heptyloxy, octyloxy, nonyloxy, decyloxy, undecyloxy and dodecyloxy and the isomers thereof, in which one or more of the hydrogen substituents is replaced in the same way or differently by halogen. More preferably the halogen is fluorine. Particularly preferably haloalkoxy is selected from —OCF$_3$, —OCHF$_2$, —OCH$_2$F, —OCF$_2$CF$_3$, or —OCH$_2$CF$_3$.

The term "haloalkyl" is to be understood as preferably meaning branched and unbranched alkyl, meaning e.g. methyl, ethyl, n-propyl, iso-propyl, n-butyl, iso-butyl, tert-butyl, sec-butyl, pentyl, iso-pentyl, hexyl, heptyl, octyl, nonyl and decyl and the isomers thereof, in which one or more of the hydrogen substituents is replaced in the same way or differently by halogen. More preferably the halogen is fluorine. Particularly preferably haloalkyl is selected from —CF$_3$, —CHF$_2$, —CH$_2$F, —CF$_2$CF$_3$, or —CH$_2$CF$_3$.

The term "C$_3$-C$_{10}$-cycloalkyl" is to be understood as preferably meaning cycloalkyl, meaning e.g. cyclopropyl, cyclobutyl, cyclopentyl, cyclohexyl, cycloheptyl, cyclooctyl, cyclononyl and cyclodecyl. C$_3$-C$_{10}$-cycloalkyl ring can optionally be interrupted one or more times, the same or differently with a group —C(O)—, —S(O)— or —S(O)$_2$— and can optionally contain one or more double bonds e.g. cycloalkenyl, such as cyclopropenyl, cyclobutenyl, cyclopentenyl, cyclohexenyl and cycloheptenyl, cyclooctenyl, cyclononenyl, cyclodecenyl, wherein the linkage can be provided to the double or single bond.

The term "C$_3$-C$_{10}$-heterocycloalkyl" preferably is a C$_3$-C$_{10}$-cycloalkyl group which is at least once interrupted by an atom, the same or different, of the group comprising, preferably consisting of, nitrogen, oxygen and/or sulfur e.g. oxyranyl, oxetanyl, aziridinyl, azetidinyl, tetrahydrofuranyl, pyrrolidinyl, morpholinyl, dithianyl, thiomorpholinyl, piperazinyl, trithianyl and chinuclidinyl. C$_3$-C$_{10}$-heterocycloalkyl ring can optionally be interrupted one or more times, the same or differently with a group —C(O)—, —S(O)— or —S(O)$_2$— and C$_3$-C$_{10}$-heterocycloalkyl ring can optionally contain one or more double bonds, e.g. 4H-pyran, 2H-pyran, 3H-diazirine, 2,5-dihydro-1H-pyrrole, [1,3]dioxole; 4H-[1,3,4]thiadiazine, 2,5-dihydrofuran, 2,3-dihydrofuran, 2,5-dihydrothiophene, 2,3-dihydrothiophene, 4,5-dihydrooxazole or 4H-[1,4]thiazine.

The term "halogen" or "hal" is to be understood as preferably meaning fluorine, chlorine, bromine, or iodine.

The term "alkenyl" is to be understood as preferably meaning branched and unbranched alkenyl, e.g. vinyl, propen-1-yl, propen-2-yl, but-1-en-1-yl, but-1-en-2-yl, but-2-en-1-yl, but-2-en-2-yl, but-1-en-3-yl, 2-methyl-prop-2-en-1-yl and 2-methyl-prop-1-en-1-yl.

The term "alkynyl" is to be understood as preferably meaning branched and unbranched alkynyl, e.g. ethynyl, prop-1-yn-1-yl, but-1-yn-1-yl, but-2-yn-1-yl and but-3-yn-1-yl.

As used herein, the term "aryl" is defined in each case as having 3-12 carbon atoms, preferably 6-12 carbon atoms, such as, for example, cyclopropenyl, cyclopentadienyl, phenyl, tropyl, cyclooctadienyl, indenyl, naphthyl, azulenyl, biphenyl, fluorenyl, anthracenyl etc, phenyl being preferred.

As used herein, the term "heteroaryl" is understood as meaning an aromatic ring system which comprises 3-16 ring atoms, preferably 5 or 6 or 9 or 10 atoms, and which contains at least one heteroatom which may be identical or different, said heteroatom being such as oxygen, nitrogen or sulfur, and can be monocyclic, bicyclic, or tricyclic, and in addition in each case can be benzocondensed. Preferably, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, e.g., benzofuranyl, benzothienyl, benzoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, isoquinolinyl, etc.; or azocinyl, indolizinyl, purinyl, etc., and benzo derivatives thereof; or cinnolinyl, phthalazinyl, quinazolinyl, quinoxalinyl, naphth-pyridinyl, pteridinyl, carbazolyl, acridinyl, phenazinyl, phenothiazinyl, phenoxazinyl, xanthenyl, or oxepinyl, etc.

As used herein, the term "C$_1$-C$_6$", as used throughout this text, e.g. in the context of the definition of "C$_1$-C$_6$-alkyl", "C$_1$-C$_6$-haloalkyl", "C$_1$-C$_6$-alkoxy", or "C$_1$-C$_6$-haloalkoxy" is to be understood as meaning an alkyl group having a finite number of carbon atoms of 1 to 6, i.e. 1, 2, 3, 4, 5, or 6 carbon atoms. It is to be understood further that said term "C$_1$-C$_6$" is to be interpreted as any sub-range comprised therein, e.g. C$_1$-C$_6$, C$_2$-C$_5$, C$_3$-C$_4$, C$_1$-C$_2$, C$_1$-C$_3$, C$_1$-C$_4$, C$_1$-C$_5$ C$_1$-C$_6$; preferably C$_1$-C$_2$, C$_1$-C$_3$, C$_1$-C$_4$, C$_1$-C$_5$, C$_1$-C$_6$; more preferably C$_1$-C$_4$; in the case of "C$_1$-C$_6$-haloalkyl" or "C$_1$-C$_6$-haloalkoxy" even more preferably C$_1$-C$_2$.

Similarly, as used herein, the term "C$_2$-C$_6$", as used throughout this text, e.g. in the context of the definitions of "C$_2$-C$_6$-alkenyl" and "C$_2$-C$_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "C$_2$-C$_6$" is to be interpreted as any sub-range comprised therein, e.g. C$_2$-C$_6$, C$_3$-C$_5$, C$_3$-C$_4$, C$_2$-C$_3$, C$_2$-C$_4$, C$_2$-C$_5$ preferably C$_2$-C$_3$.

Further, as used herein, the term "C$_3$-C$_{10}$", as used throughout this text, e.g. in the context of the definitions of "C$_3$-C$_{10}$-cycloalkyl" or "C$_3$-C$_{10}$-heterocycloalkyl", is to be understood as meaning a cycloalkyl group having a finite number of carbon atoms of 3 to 10, i.e. 3, 4, 5, 6, 7, 8, 9 or 10 carbon atoms, preferably 3, 4, 5 or 6 carbon atoms. It is to be understood further that said term "C$_3$-C$_{10}$" is to be interpreted as any sub-range comprised therein, e.g. C$_3$-C$_{10}$, C$_4$-C$_9$, C$_5$-C$_8$, C$_6$-C$_7$; preferably C$_3$-C$_6$.

Moreover, as used herein, the structural moiety:

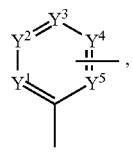

as contained in the general formula (I) of the present invention, which structural moiety is substituted in any position with the:

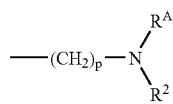

substituent (in which the meanings of $p$, $R^A$ and $R^2$ are given supra), is understood as preferably meaning a six-membered, aromatic "spacer" ring system, which is connected, via the lower bond shown thereon, to the 4-position of the pyrazolopyridine moiety of the general formula (I) of the present invention, in which $Y^1, Y^2, Y^3, Y^4$ and $Y^5$, independently from each other, stand for —CH=, —CZ= or —N=, and —N= can stand 0, 1, 2, or 3 times as a ring atom. Preferably, said six-membered, aromatic "spacer" ring system is selected from the group consisting of:

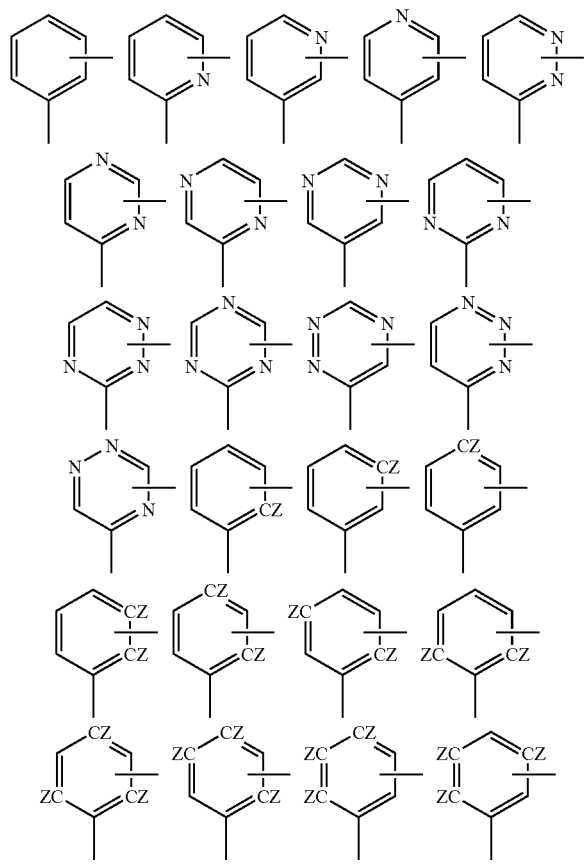

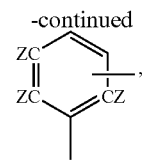

wherein Z is defined as for general formula (I) of the present invention, supra. More preferably, said six-membered, aromatic "spacer" ring system is:

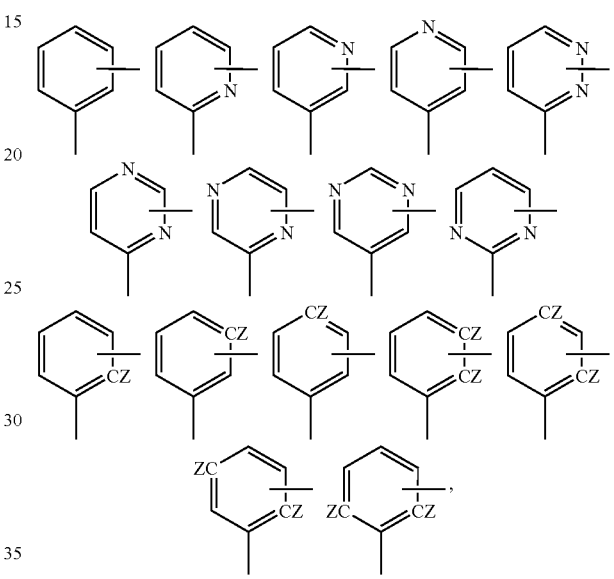

wherein Z is defined as for general formula (I) of the present invention, supra. More preferably still, said six-membered, aromatic "spacer" ring system is:

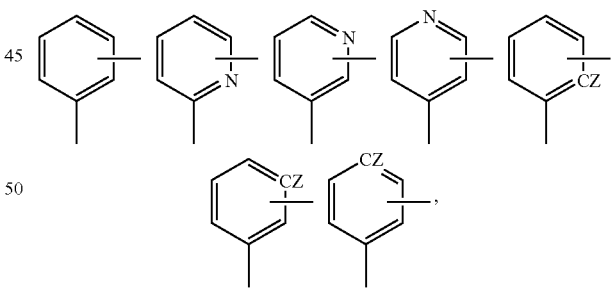

wherein Z is defined as for general formula (I) of the present invention, supra.

The term "isomers" is to be understood as meaning chemical compounds with the same number and types of atoms as another chemical species. There are two main classes of isomers, constitutional isomers and stereoisomers.

The term "constitutional isomers" is to be understood as meaning chemical compounds with the same number and types of atoms, but they are connected in differing sequences. There are functional isomers, structural isomers, tautomers or valence isomers.

In stereoisomers, the atoms are connected sequentially in the same way, such that condensed formulae for two isomeric molecules are identical. The isomers differ, however, in the way the atoms are arranged in space. There are two major sub-classes of stereoisomers; conformational isomers, which interconvert through rotations around single bonds, and configurational isomers, which are not readily interconvertable.

Configurational isomers are, in turn, comprised of enantiomers and diastereomers. Enantiomers are stereoisomers which are related to each other as mirror images. Enantiomers can contain any number of stereogenic centers, as long as each center is the exact mirror image of the corresponding center in the other molecule. If one or more of these centers differs in configuration, the two molecules are no longer mirror images. Stereoisomers which are not enantiomers are called diastereomers. Diastereomers which still have a different constitution, are another sub-class of diastereomers, the best known of which are simple cis-trans isomers.

In order to limit different types of isomers from each other reference is made to IUPAC Rules Section E (*Pure Appl Chem* 45, 11-30, 1976).

The compound according to Formula (I) can exist in free form or in a salt form. A suitably pharmaceutically acceptable salt of the pyrazolopyridines of the present invention may be, for example, an acid-addition salt of a pyrazolopyridine of the invention which is sufficiently basic, for example, an acid-addition salt with, for example, an inorganic or organic acid, for example hydrochloric, hydrobromic, sulphuric, phosphoric, trifluoroacetic, para-toluenesulphonic, methylsulphonic, citric, tartaric, succinic or maleic acid. In addition, another suitably pharmaceutically acceptable salt of a pyrazolopyridine of the invention which is sufficiently acidic is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, 1,6-hexadiamine, ethanolamine, glucosamine, sarcosine, serinol, tris-hydroxy-methyl-aminomethane, aminopropandiol, sovak-base, 1-amino-2,3,4-butantriol.

The compound according to Formula (I) can exist as N-oxides which are defined in that at Least one nitrogen of the compounds of the general Formula (I) may be oxidized.

The compound according to Formula (I) can exist as solvates, in particular as hydrate, wherein the compound according to Formula (I) may contain polar solvents, in particular water, as structural element of the crystal lattice of the compounds. The amount of polar solvents, in particular water, may exist in a stoichiometric or unstoichiometric ratio. In case of stoichiometric solvates, e.g. hydrate, are possible hemi-, (semi-), mono-, sesqui-, di-, tri-, tetra-, penta- etc. solvates or hydrates, respectively.

As used herein, the term "in vivo hydrolysable ester" is understood as meaning an in vivo hydrolysable ester of a compound of formula (I) containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention. An in vivo hydrolysable ester of a compound of formula (I) containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Compounds of general formula (I), supra, of the present invention are preferred wherein:

$R^1$ stands for $C_1$-$C_6$-alkyl, $C_2$-$C_6$-alkenyl, $C_2$-$C_6$-alkynyl, $C_3$-$C_{10}$-cycloalkyl, $C_3$-$C_{10}$-heterocycloalkyl, aryl or heteroaryl optionally being substituted one or more times, the same way or differently with K, whereby $C_3$-$C_{10}$-heterocycloalkyl itself must at least once be interrupted by an atom of the group comprising, preferably consisting of, nitrogen, oxygen and/or sulfur and whereby $C_3$-$C_{10}$-cycloalkyl ring and/or $C_3$-$C_{10}$-heterocycloalkyl ring can optionally be interrupted one or more times, the same or differently with a group —C(O)—, —S(O)— or —S(O)$_2$— and whereby $C_3$-$C_{10}$-cycloalkyl ring and/or $C_3$-$C_{10}$-heterocycloalkyl ring can optionally contain one or more double bonds, K stands for halogen, hydroxy or a substituent of the group comprising, preferably consisting of, —OR$^3$ or —NR$^5$R$^6$ or for $C_3$-$C_{10}$-cycloalkyl, $C_3$-$C_{10}$-heterocycloalkyl, aryl or heteroaryl optionally being substituted one or more times, the same way or differently with L, whereby $C_3$-$C_{10}$-heterocycloalkyl itself must at least one time be interrupted by an atom of the group comprising, preferably consisting of, nitrogen, oxygen and/or sulfur and whereby $C_3$-$C_{10}$-cycloalkyl ring and/or $C_3$-$C_{10}$-heterocycloalkyl ring can optionally be interrupted one or more times, the same or differently with a group —C(O)—, —S(O)— or —S(O)$_2$— and whereby $C_3$-$C_{10}$-cycloalkyl ring and/or $C_3$-$C_{10}$-heterocycloalkyl ring can optionally contain one or more double bonds, L stands for a substituent of the group comprising, preferably consisting of, —C(O)R$^4$ or —NR$^5$R$^6$ or for $C_1$-$C_6$-alkyl optionally being substituted one or more times, the same way or differently with halogen, hydroxy, cyano, nitro or the group —NR$^5$R$^6$ or —C(O)R$^4$, $R^4$ stands for hydrogen or $C_1$-$C_6$-alkyl optionally being substituted one or more times, the same way or differently with halogen, hydroxy, cyano, nitro or the group —NR$^5$R$^6$ or —C(O)R$^4$, $R^2$ stands for a substituent of the group comprising, preferably consisting of, —C(O)—NR$^7$R$^{7a}$, —S(O)$_2$—R$^7$, —S(O)$_2$NR$^7$R$^{7a}$, —S(O)(NH)R$^7$—C(O)R$^7$ or —C(O)OR$^7$, $R^3$ stands for $C_1$-$C_6$-alkyl, aryl or —(CH$_2$)$_n$-aryl, wherein $C_1$-$C_6$-alkyl, aryl or —(CH$_2$)$_n$-aryl can optionally be substituted one or more times, the same way or differently with $C_1$-$C_6$-alkyl, $C_1$-$C_6$-alkoxy, halogen, hydroxy, cyano, nitro or the group —NR$^5$R$^6$ or —C(O)R$^4$, $R^4$ stands for hydrogen, hydroxy, $C_1$-$C_6$-alkyl, $C_1$-$C_6$-haloalkyl, $C_1$-$C_6$-alkoxy or the group —NR$^5$R$^6$, $R^5$ and $R^6$ independently from one another stand for hydrogen, $C_1$-$C_6$-alkyl, aryl, —(CH$_2$)$_n$-aryl, or for a group —C(O)R$^4$, wherein $C_1$-$C_6$-alkyl or aryl can optionally be substituted one or more times, the same way or differently with halogen, hydroxy, cyano, nitro or the group —NR$^7$R$^{7a}$ or —C(O)R$^4$, or R$^5$ and R$^6$ together with the nitrogen atom to which they are attached, form a 3 to 10 membered heterocycloalkyl ring, whereby heterocycloalkyl ring itself must at least one time be interrupted by an atom of the group comprising, preferably consisting of, nitrogen, oxygen and/or sulfur and can optionally be interrupted one or more times, the same way or differently with a group —C(O)—, —S(O)— and/or —S(O)$_2$— and can optionally contain one or more double bonds, R$^7$ and R$^{7a}$, independently from one another stand for hydrogen, C$_1$-C$_6$-alkyl, C$_3$-C$_{10}$-cycloalkyl, C$_3$-C$_{10}$-heterocycloalkyl, aryl or heteroaryl, wherein C$_1$-C$_6$-alkyl, C$_3$-C$_{10}$-cycloalkyl, C$_3$-C$_{10}$-heterocycloalkyl, aryl or heteroaryl can optionally be substituted one or more times, the same way or differently with M, whereby C$_3$-C$_{10}$-heterocycloalkyl itself must at least one time be interrupted by an atom of the group comprising, preferably consisting of, nitrogen, oxygen and/or sulfur and whereby C$_3$-C$_{10}$-cycloalkyl ring and/or C$_3$-C$_{10}$-heterocycloalkyl ring can optionally be interrupted one or more times, the same way or differently with a group —C(O)—, —S(O)— or —S(O)$_2$— and whereby C$_3$-C$_{10}$-cycloalkyl ring and/or C$_3$-C$_{10}$-heterocycloalkyl ring can optionally contain one or more double bonds, or R$^7$ and R$^{7a}$ together with the nitrogen atom to which they are attached, form a 3 to 10 membered heterocycloalkyl ring, whereby heterocycloalkyl ring itself must at least one time be interrupted by an atom of the group comprising, preferably consisting of, nitrogen, oxygen and/or sulfur and can optionally be interrupted one or more times, the same way or differently with a group —C(O)—, —S(O)— or —S(O)$_2$— and can optionally contain one or more double bonds, M stands for a substituent of the group comprising, preferably consisting of, cyano, halogen, hydroxy, nitro or for C$_1$-C$_6$-alkyl, C$_2$-C$_6$-alkenyl, C$_2$-C$_6$-alkynyl, C$_1$-C$_6$-alkoxy, C$_1$-C$_6$-haloalkoxy, C$_1$-C$_6$-haloalkyl, aryl, C$_3$-C$_{10}$-heteroaryl, —(CH$_2$)$_m$-phenyl or —(CH$_2$)$_m$—O—(CH$_2$)$_q$phenyl, wherein C$_1$-C$_6$-alkyl, C$_2$-C$_6$-alkenyl, C$_2$-C$_6$-alkynyl, C$_1$-C$_6$-alkoxy, aryl, C$_3$-C$_{10}$-heteroaryl, —(CH$_2$)$_m$-phenyl or —(CH$_2$)$_m$—O—(CH$_2$)$_q$phenyl can optionally be substituted one or more times, the same way or differently with a substituent of the group comprising, preferably consisting of, amino, cyano, halogen, hydroxy, nitro, C$_1$-C$_6$-alkyl, C$_1$-C$_6$-alkoxy, C$_1$-C$_6$-haloalkoxy, C$_1$-C$_6$-haloalkyl, —(CH$_2$)$_m$-phenyl or —(CH$_2$)$_m$—O—(CH$_2$)$_q$phenyl, the structural moiety:

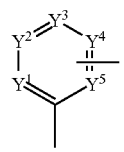

is selected from the group consisting of:

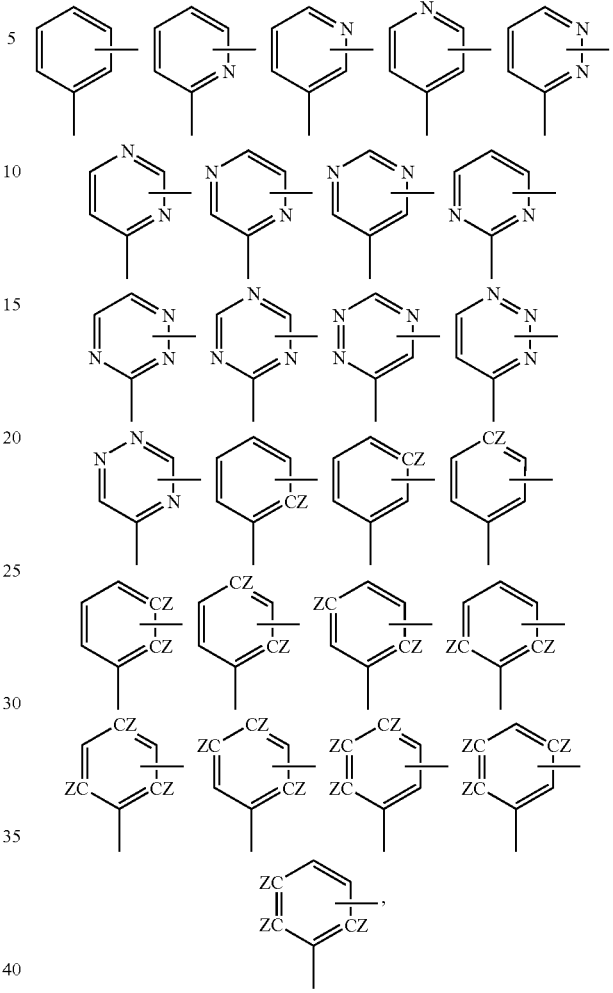

wherein z stands for cyano, nitro, halogen, hydroxy or a substituent of the group comprising, preferably consisting of, —NR$^5$R$^6$, —OR$^3$, —C(O)R$^7$, —C(O)OR$^7$, —C(O)NR$^7$R$^{7a}$, —S(O)R$^7$ or —S(O)$_2$R$^7$ or for C$_1$-C$_6$-alkyl, C$_2$-C$_6$-alkenyl, C$_2$-C$_6$-alkynyl or C$_3$-C$_{10}$-cycloalkyl, whereby C$_1$-C$_6$-alkyl, C$_2$-C$_6$-alkenyl, C$_2$-C$_6$-alkynyl or C$_3$-C$_{10}$-cycloalkyl can optionally be substituted one or more times, the same way or different with cyano, nitro, halogen, hydroxy, —OR$^3$ or —NR$^5$R$^6$, m stands for an integer of 0, 1, 2, 3, or 4, n stands for an integer of 0, 1, 2, 3, or 4, p stands for an integer of 0, 1, 2, 3, or 4, and q stands for an integer of 0, 1, 2, 3, or 4, as welt as N-oxides, solvates, hydrates, isomers, diastereomers, enantiomers and salts thereof, which are effective inhibitors of Tie2 kinase.

Compounds of general formula (I) are more preferred, wherein:

R$^1$ stands for C$_1$-C$_6$-alkyl, C$_2$-C$_6$-alkenyl, C$_2$-C$_6$-alkynyl, C$_3$-C$_{10}$-cycloalkyl, aryl or heteroaryl optionally being substituted one or more times, the same way or differently with K, K stands for halogen, hydroxy or stands for morpholinyl, piperazinyl, piperidinyl, pyrrolidinyl or phenoxy optionally substituted with L, L stands for $C_1$-$C_6$-alkyl or —C(O)O—$C_1$-$C_6$ alkyl, whereby $C_1$-$C_6$-alkyl or —C(O)O—$C_1$-$C_6$ alkyl can optionally be substituted one or more times, the same way or differently with halogen, $R^A$ stands for hydrogen or $C_1$-$C_6$-alkyl optionally being substituted one or more times, the same way or differently with halogen, hydroxy, cyano, nitro or the group —$NR^5R^6$ or —C(O)$R^4$, $R^2$ stands for a substituent of the group comprising, preferably consisting of, —C(O)—$NR^7R^{7a}$, —S(O)$_2$—$R^7$, —S(O)$_2NR^7R^{7a}$, —S(O)(NH)$R^7$, —C(O)$R^7$ or —C(O)O$R^7$, $R^3$ stands for $C_1$-$C_6$-alkyl, aryl or —$(CH_2)_n$-aryl, wherein $C_1$-$C_6$-alkyl, aryl or —$(CH_2)_n$-aryl can optionally be substituted one or more times, the same way or differently with $C_1$-$C_6$-alkyl, $C_1$-$C_6$-alkoxy, halogen, hydroxy, cyano, nitro or the group —$NR^5R^6$ or —C(O)$R^4$, $R^4$ stands for hydrogen, hydroxy, $C_1$-$C_6$-alkyl, $C_1$-$C_6$-haloalkyl, $C_1$-$C_6$-alkoxy or the group —$NR^5R^6$, $R^5$ and $R^6$ independently from one another stand for hydrogen, $C_1$-$C_6$-alkyl, aryl or for a group —C(O)$R^4$, wherein $C_1$-$C_6$-alkyl or aryl can optionally be substituted one or more times, the same way or differently with halogen, hydroxy, cyano, nitro or the group —$NR^7R^{7a}$ or —C(O)$R^4$, $R^7$ and $R^{7a}$ independently from one another stand for hydrogen, $C_1$-$C_6$-alkyl, $C_3$-$C_{10}$-cycloalkyl, $C_3$-$C_{10}$-heterocycloalkyl, aryl or heteroaryl, wherein $C_1$-$C_6$-alkyl, $C_3$-$C_{10}$-cycloalkyl, $C_3$-$C_{10}$-heterocycloalkyl, aryl or heteroaryl optionally being substituted one or more times, the same way or differently with M, M stands for a substituent of the group comprising, preferably consisting of, cyano, halogen, hydroxy, nitro or for $C_1$-$C_6$-alkyl, $C_2$-$C_6$-alkenyl, $C_2$-$C_6$-alkynyl, $C_1$-$C_6$-alkoxy, aryl, $C_3$-$C_{10}$-heteroaryl, —$(CH_2)_m$-phenyl or —$(CH_2)_m$—O—$(CH_2)_q$phenyl, wherein $C_1$-$C_6$-alkyl, $C_2$-$C_6$-alkenyl, $C_2$-$C_6$-alkynyl, $C_1$-$C_6$-alkoxy, aryl, $C_3$-$C_{10}$-heteroaryl, —$(CH_2)_m$-phenyl or —$(CH_2)_m$—O—$(CH_2)_q$phenyl can optionally be substituted one or more times, the same way or differently with a substituent of the group comprising, preferably consisting of, amino, cyano, halogen, hydroxy, nitro, or $C_1$-$C_6$-alkoxy, the structural moiety:

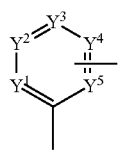

is selected from the group consisting of:

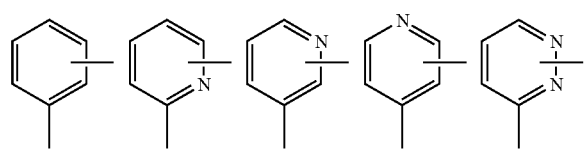

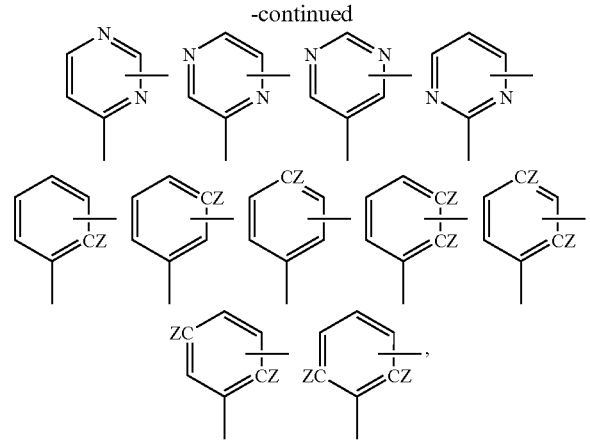

wherein

Z stands for cyano, nitro, halogen, hydroxy or a substituent of the group comprising, preferably consisting of, —$NR^5R^6$, —$OR^3$, —C(O)$R^7$, —C(O)O$R^7$, —C(O)$NR^7R^{7a}$, —S(O)$R^7$ or —S(O)$_2R^7$ or for $C_1$-$C_6$-alkyl, $C_2$-$C_6$-alkenyl, $C_2$-$C_6$-alkynyl or $C_3$-$C_{10}$-cycloalkyl, whereby $C_1$-$C_6$-alkyl, $C_2$-$C_6$-alkenyl, $C_2$-$C_6$-alkynyl or $C_3$-$C_{10}$-cycloalkyl can optionally be substituted one or more times, the same way or different with cyano, nitro, halogen, hydroxy, —$OR^3$ or —$NR^5R^6$, m stands for an integer of 0, 1, 2, 3, or 4,
n stands for an integer of 0, 1, 2, 3, or 4,
p stands for an integer of 0, 1, 2, 3, or 4, and
q stands for an integer of 0, 1, 2, 3, or 4, as well as N-oxides, solvates, hydrates, isomers, diastereomers, enantiomers and salts thereof.

Compounds of general formula (I) are more particularly preferred, wherein:

$R^1$ stands for $C_1$-$C_6$-alkyl substituted with K, $C_3$-$C_{10}$-cycloalkyl substituted with K, unsubstituted $C_1$-$C_6$-alkyl, particularly tert-butyl, or isopropyl, or unsubstituted $C_3$-$C_{10}$-cycloalkyl, particularly cyclopropyl, K stands for halogen, hydroxy or stands for morpholinyl, piperazinyl, piperidinyl or phenoxy, L stands for $C_1$-$C_6$-alkyl or —C(O)O—$C_1$-$C_6$-alkyl, whereby $C_1$-$C_6$-alkyl or —C(O)O—$C_1$-$C_6$-alkyl can optionally be substituted one or more times, the same way or differently with halogen, $R^A$ stands for hydrogen, $R^2$ stands for a substituent of the group comprising, preferably consisting of, —C(O)—NH—$R^7$, —S(O)$_2$—$R^7$, or —C(O)$R^7$, $R^3$ stands for $C_1$-$C_6$-alkyl, aryl or —$(CH_2)_n$-aryl, wherein $C_1$-$C_6$-alkyl, aryl or —$(CH_2)_n$-aryl can optionally be substituted one or more times, the same way or differently with $C_1$-$C_6$-alkyl, $C_1$-$C_6$-alkoxy, halogen, hydroxy, cyano, nitro or the group —$NR^5R^6$ or —C(O)$R^4$, $R^4$ stands for hydrogen, hydroxy, $C_1$-$C_6$-alkyl, $C_1$-$C_6$-haloalkyl, $C_1$-$C_6$-alkoxy or the group —$NR^5R^6$, $R^5$ and $R^6$ independently from one another stand for hydrogen, $C_1$-$C_6$-alkyl, aryl or for a group —C(O)$R^4$, wherein $C_1$-$C_6$-alkyl or aryl can optionally be substituted one or more times, the same way or differently with halogen, hydroxy, cyano, nitro or the group —$NR^7R^{7a}$ or —C(O)$R^4$, $R^7$ and $R^{7a}$ independently from one another stand for $C_1$-$C_2$ alkyl, cyclopropyl, or phenyl, whereby $C_1$-$C_2$ alkyl, cyclopropyl, or phenyl may be optionally substituted one or more times, the same way or differently with M, M stands for a substituent of the group comprising, preferably consisting of, cyano, halogen, hydroxy, nitro or for $C_1$-$C_6$-alkyl, $C_2$-$C_6$-alkenyl, $C_2$-$C_6$-alkynyl, $C_1$-$C_6$-alkoxy, aryl, $C_3$-$C_{10}$-heteroaryl, —$(CH_2)_m$-phenyl or —$(CH_2)_m$—O—$(CH_2)_q$phenyl, wherein $C_1$-$C_6$-alkyl, $C_2$-$C_6$-alkenyl, $C_2$-$C_6$-alkynyl, $C_1$-$C_6$-alkoxy, aryl, $C_3$-$C_{10}$-heteroaryl, —$(CH_2)_m$-phenyl or —$(CH_2)_m$—O—$(CH_2)_q$phenyl can optionally be substituted one or more times, the same way or differently with a substituent of the group comprising, preferably consisting of, amino, cyano, halogen, hydroxy, nitro, or $C_1$-$C_6$-alkoxy, the structural moiety:

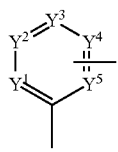

is selected from the group consisting of:

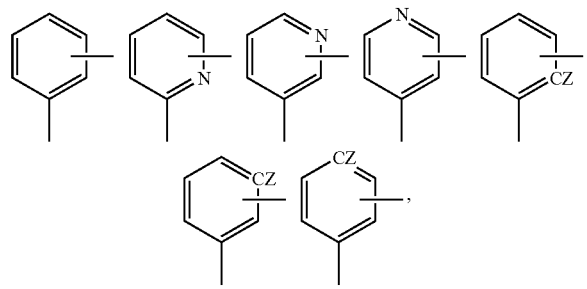

wherein z stands for cyano, nitro, halogen, hydroxy or a substituent of the group comprising, preferably consisting of, —$NR^5R^6$, —$OR^3$, —$C(O)R^7$, —$C(O)OR^7$, —$C(O)NR^7R^{7a}$, —$S(O)R^7$ or —$S(O)_2R^7$ or for $C_1$-$C_6$-alkyl, $C_2$-$C_6$-alkenyl, $C_2$-$C_6$-alkynyl or $C_3$-$C_{10}$-cycloalkyl, whereby $C_1$-$C_6$-alkyl, $C_2$-$C_6$-alkenyl, $C_2$-$C_6$-alkynyl or $C_3$-$C_{10}$-cycloalkyl can optionally be substituted one or more times, the same way or different with cyano, nitro, halogen, hydroxy, —$OR^3$ or —$NR^5R^6$, and m stands for an integer of 0, 1, 2, 3, or 4,
n stands for an integer of 0, 1, 2, 3, or 4,
p stands for an integer of 0, 1, 2, 3, or 4, and
q stands for an integer of 0, 1, 2, 3, or 4, as well as N-oxides, solvates, hydrates, isomers, diastereomers, enantiomers and salts thereof.

Compounds of general formula (I) are even more particularly preferred, wherein $R^1$ stands for $C_1$-$C_6$-alkyl substituted with K, $C_3$-$C_{10}$-cycloalkyl substituted with K, unsubstituted $C_1$-$C_6$-alkyl, particularly tert-butyl, or isopropyl, or unsubstituted $C_3$-$C_{10}$-cycloalkyl, particularly cyclopropyl, K stands for halogen, hydroxy or stands for morpholinyl, piperazinyl, piperidinyl or phenoxy, L stands for $C_1$-$C_6$-alkyl or —$C(O)O$—$C_1$-$C_6$-alkyl, whereby $C_1$-$C_6$-alkyl or —$C(O)O$—$C_1$-$C_6$-alkyl can optionally be substituted one or more times, the same way or differently with halogen, $R^A$ stands for hydrogen, $R^2$ stands for a substituent of the group comprising —$C(O)$—$NH$—$R^7$, —$S(O)_2$—$R^7$, or —$C(O)R^7$, $R^7$ stands for $C_1$-$C_2$-alkyl, cyclopropyl, or phenyl, whereby $C_1$-$C_2$-alkyl, cyclopropyl, or phenyl may be optionally substituted one or more times, the same way or differently with M, M stands for a substituent of the group comprising, preferably consisting of, cyano, halogen, hydroxy, nitro or for $C_1$-$C_6$-alkyl, $C_2$-$C_6$-alkenyl, $C_2$-$C_6$-alkynyl, $C_1$-$C_6$-alkoxy, aryl, $C_3$-$C_{10}$-heteroaryl, —$(CH_2)_m$-phenyl or —$(CH_2)_m$—O—$(CH_2)_q$phenyl, wherein $C_1$-$C_6$-alkyl, $C_2$-$C_6$-alkenyl, $C_2$-$C_6$-alkynyl, $C_1$-$C_6$-alkoxy, aryl, $C_3$-$C_{10}$-heteroaryl, —$(CH_2)_m$-phenyl or —$(CH_2)_m$—O—$(CH_2)_q$phenyl can optionally be substituted one or more times, the same way or differently with a substituent of the group comprising, preferably consisting of, amino, cyano, halogen, hydroxy, nitro, or $C_1$-$C_6$-alkoxy, the structural moiety:

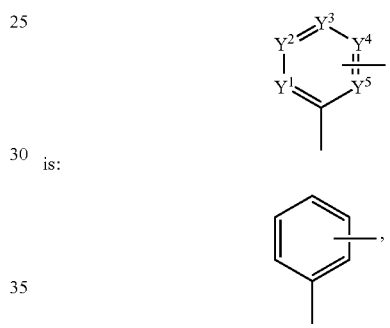

is:

m stands for 0 or 1,
n stands for 0 or 1,
p stands for 0, and
q stands for 0 or 1, as well as N-oxides, solvates, hydrates, isomers, diastereomers, enantiomers and salts thereof.

Compounds of general formula (I) are even further more particularly preferred, wherein:

$R^1$ stands for tert-butyl, isopropyl or cyclopropyl, $R^A$ stands for hydrogen, $R^2$ stands for a substituent of the group comprising, preferably consisting of, —$C(O)$—$NH$—$R^7$, —$S(O)_2$—$R^7$, or —$C(O)R^7$, $R^7$ stands for $C_1$-$C_2$-alkyl, cyclopropyl, or phenyl, whereby $C_1$-$C_2$-alkyl, cyclopropyl, or phenyl may be optionally substituted one or more times, the same way or differently with M, M stands for a substituent of the group comprising, preferably consisting of, phenyl, hydroxyl, cyano, halogen, nitro, $C_1$-$C_2$-haloalkyl, $C_1$-$C_2$-alkoxy, $C_1$-$C_2$-haloalkoxy, —$(CH_2)_m$-phenyl or —$(CH_2)_m$—O—$(CH_2)_q$phenyl, or for $C_1$-$C_2$-alkyl, whereby the phenyl substituent may be optionally substituted one or more times, the same way or different with hydroxy, cyano, halogen, nitro, $C_1$-$C_2$-haloalkyl, $C_1$-$C_2$-alkoxy, $C_1$-$C_2$-haloalkoxy, or $C_1$-$C_2$-alkyl, the structural moiety:

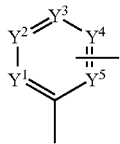

is:

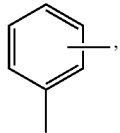

m stands for 0 or 1,
n stands for 0 or 1,
q stands for 0 or 1,
and
p stands for 0, as well as N-oxides, solvates, hydrates, isomers, diastereomers, enantiomers and salts thereof.

Advantageously, the following compounds are even more particularly preferred still 1-[4-(3-amino-6-tert-butyl-1H-pyrazolo[3,4-b]pyridin-4-yl)-phenyl]-3-phenyl-urea;
N-[4-(3-amino-6-tert-butyl-1H-pyrazolo[3,4-b]pyridin-4-yl)-phenyl]-benzenesulfonamide;
1-[4-(3-amino-6-tert-butyl-1H-pyrazolo[3,4-b]pyridin-4-yl)-phenyl]-3-(3-fluoro-phenyl)-urea;
1-[4-(3-amino-6-tert-butyl-1H-pyrazolo[3,4-b]pyridin-4-yl)-phenyl]-3-(2-fluoro-phenyl)-urea 1-[4-(3-amino-6-tert-butyl-1H-pyrazolo[3,4-b]pyridin-4-yl)-phenyl]-3-(2,5-difluoro-phenyl)-urea;
1-[4-(3-amino-6-tert-butyl-1H-pyrazolo[3,4-b]pyridin-4-yl)-phenyl]-3-(3,4-difluoro-phenyl)-urea;
1-[4-(3-amino-6-tert-butyl-1H-pyrazolo[3,4-b]pyridin-4-yl)-phenyl]-3-naphthalen-1-yl-urea;
1-[4-(3-amino-6-tert-butyl-1H-pyrazolo[3,4-b]pyridin-4-yl)-phenyl]-3-naphthalen-2-yl-urea;
1-[4-(3-amino-6-tert-butyl-1H-pyrazolo[3,4-b]pyridin-4-yl)-phenyl]-3-m-tolyl-urea;
1-[4-(3-amino-6-tert-butyl-1H-pyrazolo[3,4-b]pyridin-4-yl)-phenyl]-3-(2-nitro-phenyl)-urea;
1-[4-(3-amino-6-tert-butyl-1H-pyrazolo[3,4-b]pyridin-4-yl)-phenyl]-3-(2,4-difluoro-phenyl)-urea;
1-[4-(3-amino-6-tert-butyl-1H-pyrazolo[3,4-b]pyridin-4-yl)-phenyl]-3-(4-fluoro-phenyl)-urea
1-[4-(3-amino-6-tert-butyl-1H-pyrazolo[3,4-b]pyridin-4-yl)-phenyl]-3-(4-cyano-phenyl)-urea;
1-[4-(3-amino-6-cyclopropyl-1H-pyrazolo[3,4-b]pyridin-4-yl)-phenyl]-3-phenyl-urea;
1-[4-(3-amino-6-cyclopropyl-1H-pyrazolo[3,4-b]pyridin-4-yl)-phenyl]-3-(2-fluoro-phenyl)-urea;
1-[4-(3-amino-6-isopropyl-1H-pyrazolo[3,4-b]pyridin-4-yl)-phenyl]-3-(3-trifluoromethyl-phenyl)-urea;
N-[4-(3-amino-6-tert-butyl-1H-pyrazolo[3,4-b]pyridin-4-yl)-phenyl]-4-methyl-benzamide
1-[4-(3-amino-6-tert-butyl-1H-pyrazolo[3,4-b]pyridin-4-yl)-phenyl]-3-benzyl-urea
1-[4-(3-amino-6-tert-butyl-1H-pyrazolo[3,4-b]pyridin-4-yl)-phenyl]-3-phenethyl-urea;
1-[4-(3-amino-6-tert-butyl-1H-pyrazolo[3,4-b]pyridin-4-yl)-phenyl]-3-isopropyl-urea;
1-[4-(3-amino-6-tert-butyl-1H-pyrazolo[3,4-b]pyridin-4-yl)-phenyl]-3-cyclopentyl-urea
1-[4-(3-amino-6-tert-butyl-1H-pyrazolo[3,4-b]pyridin-4-yl)-phenyl]-3-cyclohexyl-urea;
1-[4-(3-amino-6-tert-butyl-1H-pyrazolo-[3,4-b]pyridin-4-yl)-phenyl]-3-(3-ethyl-phenyl)-urea;
1-[4-(3-amino-6-tert-butyl-1H-pyrazolo[3,4-b]pyridin-4-yl)-phenyl]-3-(2-fluoro-3-trifluoromethyl-phenyl)-urea;
1-[4-(3-amino-6-tert-butyl-1H-pyrazolo-[3,4-b]pyridin-4-yl)-phenyl]-3-p-tolyl-urea;
1-[4-(3-amino-6-tert-butyl-1H-pyrazolo-[3,4-b]pyridin-4-yl)-phenyl]-3-(3-benzyl-phenyl)-urea;
1-[4-(3-amino-6-tert-butyl-1H-pyrazolo-[3,4-b]pyridin-4-yl)-phenyl]-3-(3-trifluoro-methyl-phenyl)-urea;
1-[4-(3-amino-6-tert-butyl-1H-pyrazolo-[3,4-b]pyridin-4-yl)-phenyl]-3-(3-cyano-phenyl)-urea;
1-[4-(3-amino-6-tert-butyl-1H-pyrazolo-[3,4-b]pyridin-4-yl)-phenyl]-3-p-tolyl-urea;
1-[4-(3-amino-6-tert-butyl-1H-pyrazolo-[3,4-b]pyridin-4-yl)-phenyl]-3-(3-methoxy-phenyl)-urea;
1-[4-(3-amino-6-tert-butyl-1H-pyrazolo[3,4-b]pyridin-4-yl)-phenyl]-3-(2-fluoro-5-methyl-phenyl)-urea;
1-[4-(3-amino-6-tert-butyl-1H-pyrazolo-[3,4-b]pyridin-4-yl)-phenyl]-3-(3-phenoxy-phenyl)-urea;
1-[4-(3-amino-6-tert-butyl-1H-pyrazolo-[3,4-b]pyridin-4-yl)-phenyl]-3-(2-methoxy-5-methyl-phenyl)-urea;
1-[4-(3-amino-6-tert-butyl-1H-pyrazolo-[3,4-b]pyridin-4-yl)-phenyl]-3-(3-nitro-phenyl)-urea;
1-[4-(3-amino-6-tert-butyl-1H-pyrazolo[3,4-b]pyridin-4-yl)-phenyl]-3-(2-chloro-5-trifluoromethyl-phenyl)-urea;
1-[4-(3-amino-6-tert-butyl-1H-pyrazolo[3,4-b]pyridin-4-yl)-phenyl]-3-biphenyl-4-yl-urea
1-[4-(3-amino-6-tert-butyl-1H-pyrazolo[3,4-b]pyridin-4-yl)-phenyl]-3-(2-fluoro-5-trifluoromethyl-phenyl)-urea;
1-[4-(3-amino-6-tert-butyl-1H-pyrazolo-[3,4-b]pyridin-4-yl)-phenyl]-3-(3-ethoxy-phenyl)-urea;
1-[4-(3-amino-6-tert-butyl-1H-pyrazolo-[3,4-b]pyridin-4-yl)-phenyl]-3-(3,5-dimethyl-phenyl)-urea;
1-[4-(3-amino-6-tert-butyl-1H-pyrazolo-[3,4-b]pyridin-4-yl)-phenyl]-3-(3,4-dimethyl-phenyl)-urea;
1-[4-(3-amino-6-tert-butyl-1H-pyrazolo-[3,4-b]pyridin-4-yl)-phenyl]-3-(2,3-dimethyl-phenyl)-urea;
1-[4-(3-amino-6-tert-butyl-1H-pyrazolo-[3,4-b]pyridin-4-yl)-phenyl]-3-(2,5-dimethyl-phenyl)-urea
1-[4-(3-amino-6-tert-butyl-1H-pyrazolo[3,4-b]pyridin-4-yl)-phenyl]-3-((S)-1-phenyl-ethyl)-urea;
1-[4-(3-amino-6-tert-butyl-1H-pyrazolo[3,4-b]pyridin-4-yl)-phenyl]-3-((R)-1-phenyl-ethyl)-urea;
1-[4-(3-amino-6-cyclo-propyl-1H-pyrazolo-[3,4-b]pyridin-4-yl)-phenyl]-3-m-tolyl-urea;
N-[4-(3-amino-6-tert-butyl-1H-pyrazolo[3,4-b]pyridin-4-yl)-phenyl]-3-methoxy-benzamide
N-[4-(3-amino-6-tert-butyl-1H-pyrazolo[3,4-b]pyridin-4-yl)-phenyl]-2-phenyl-acetamide;
N-[4-(3-amino-6-tert-butyl-1H-pyrazolo[3,4-b]pyridin-4-yl)-phenyl]-2-o-tolyl-acetamide;
1-phenyl-cyclopropanecarboxylic acid[4-(3-amino-6-tert-butyl-1H-pyrazolo[3,4-b]pyridin-4-yl)-phenyl]-amide;
N-[4-(3-amino-6-tert-butyl-1H-pyrazolo[3,4-b]pyridin-4-yl)-phenyl]-2-(3-methoxy-phenyl)-acetamide;
N-[4-(3-amino-6-tert-butyl-1H-pyrazolo[3,4-b]pyridin-4-yl)-phenyl]-2-phenyl-isobutyramide;
N-[4-(3-amino-6-tert-butyl-1H-pyrazolo[3,4-b]pyridin-4-yl)-phenyl]-2-(4-chloro-phenyl)-acetamide;
N-[4-(3-amino-6-tert-butyl-1H-pyrazolo[3,4-b]pyridin-4-yl)-phenyl]-2-(4-methoxy-phenyl)-acetamide;

N-[4-(3-amino-6-tert-butyl-1H-pyrazolo[3,4-b]pyridin-4-yl)-phenyl]-3-methyl-benzamide
N-[4-(3-amino-6-tert-butyl-1H-pyrazolo[3,4-b]pyridin-4-yl)-phenyl]-2-phenyl-butyramide;
N-[4-(3-amino-6-tert-butyl-1H-pyrazolo-[3,4-b]pyridin-4-yl)-phenyl]-3,4-difluoro-benzenesulfonamide;
N-[4-(3-amino-6-tert-butyl-1H-pyrazolo-[3,4-b]pyridin-4-yl)-phenyl]-3-nitro-benzenesulfonamide;
N-[4-(3-amino-6-tert-butyl-1H-pyrazolo-[3,4-b]pyridin-4-yl)-phenyl]-3-fluoro-benzenesulfonamide;
N-[4-(3-amino-6-tert-butyl-1H-pyrazolo-[3,4-b]pyridin-4-yl)-phenyl]-3,5-difluoro-benzenesulfonamide;
N-[4-(3-amino-6-tert-butyl-1H-pyrazolo-[3,4-b]pyridin-4-yl)-phenyl]-4-methyl-benzenesulfonamide;
N-[4-(3-amino-6-tert-butyl-1H-pyrazolo-[3,4-b]pyridin-4-yl)-phenyl]-3-methyl-benzenesulfonamide;
N-[4-(3-amino-6-tert-butyl-1H-pyrazolo-[3,4-b]pyridin-4-yl)-phenyl]-2,4-difluoro-benzenesulfonamide;
N-[4-(3-amino-6-cyclo-propyl-1H-pyrazolo-[3,4-b]pyridin-4-yl)-phenyl]-benzene-sulfonamide;
N-[4-(3-amino-6-cyclo-propyl-1H-pyrazolo-[3,4-b]pyridin-4-yl)-phenyl]-3-nitro-benzenesulfonamide;
N-[4-(3-amino-6-cyclo-propyl-1H-pyrazolo-[3,4-b]pyridin-4-yl)-phenyl]-4-methyl-benzenesulfonamide; and
N-[4-(3-amino-6-cyclo-propyl-1H-pyrazolo-[3,4-b]pyridin-4-yl)-phenyl]-3-methyl-benzenesulfonamide.

Another aspect of the invention is a method of preparing pyrazolopyridines of general formula (I) described supra, the method comprising the following method steps:

A) an aldehyde of general formula 1 is allowed to react with a methyl ketone of general formula 2, an alkyl cyanoacetate and a suitable ammonium salt, preferably ammonium acetate, to produce an intermediate compound of general formula 3:

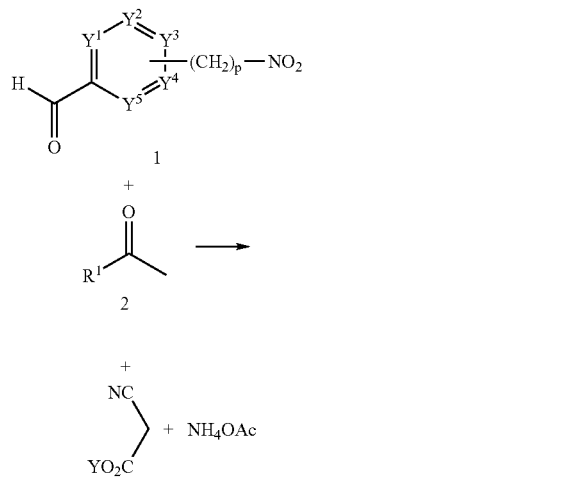

B) an intermediate compound of general formula 3 is converted to an intermediate compound of general formula 4:

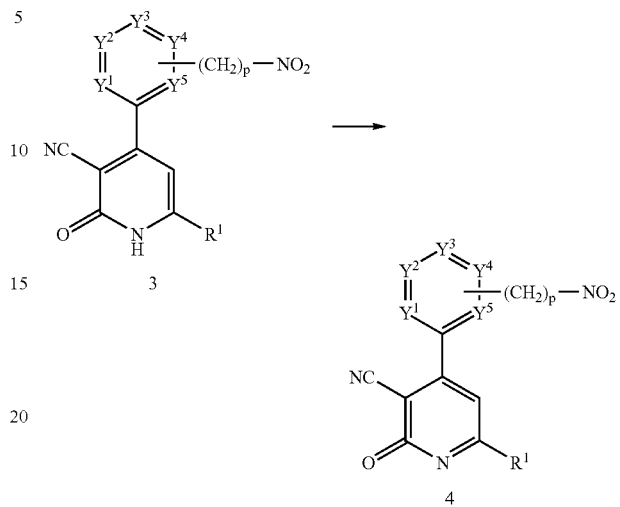

C) an intermediate compound of general formula 4 is converted, for example by reduction, to an intermediate compound of general formula 5:

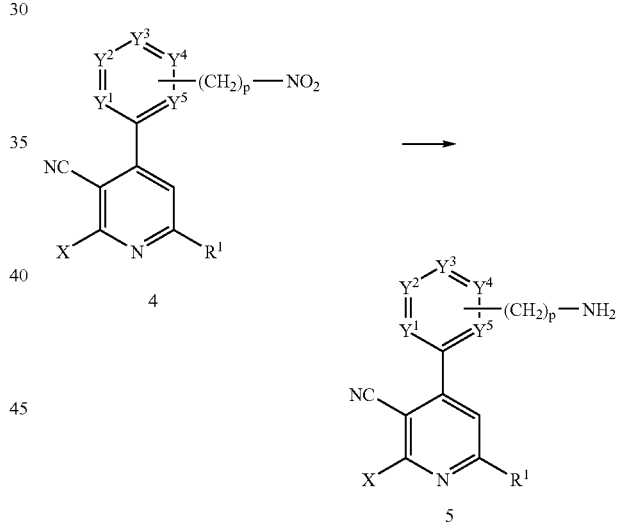

D) an intermediate compound of general formula 5 is converted to an intermediate compound of general formula 6:

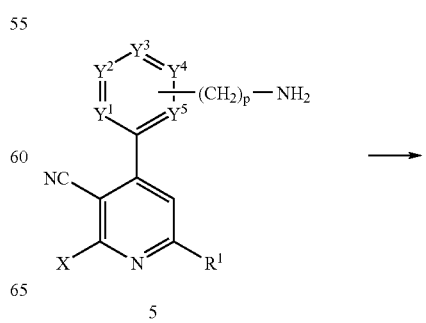

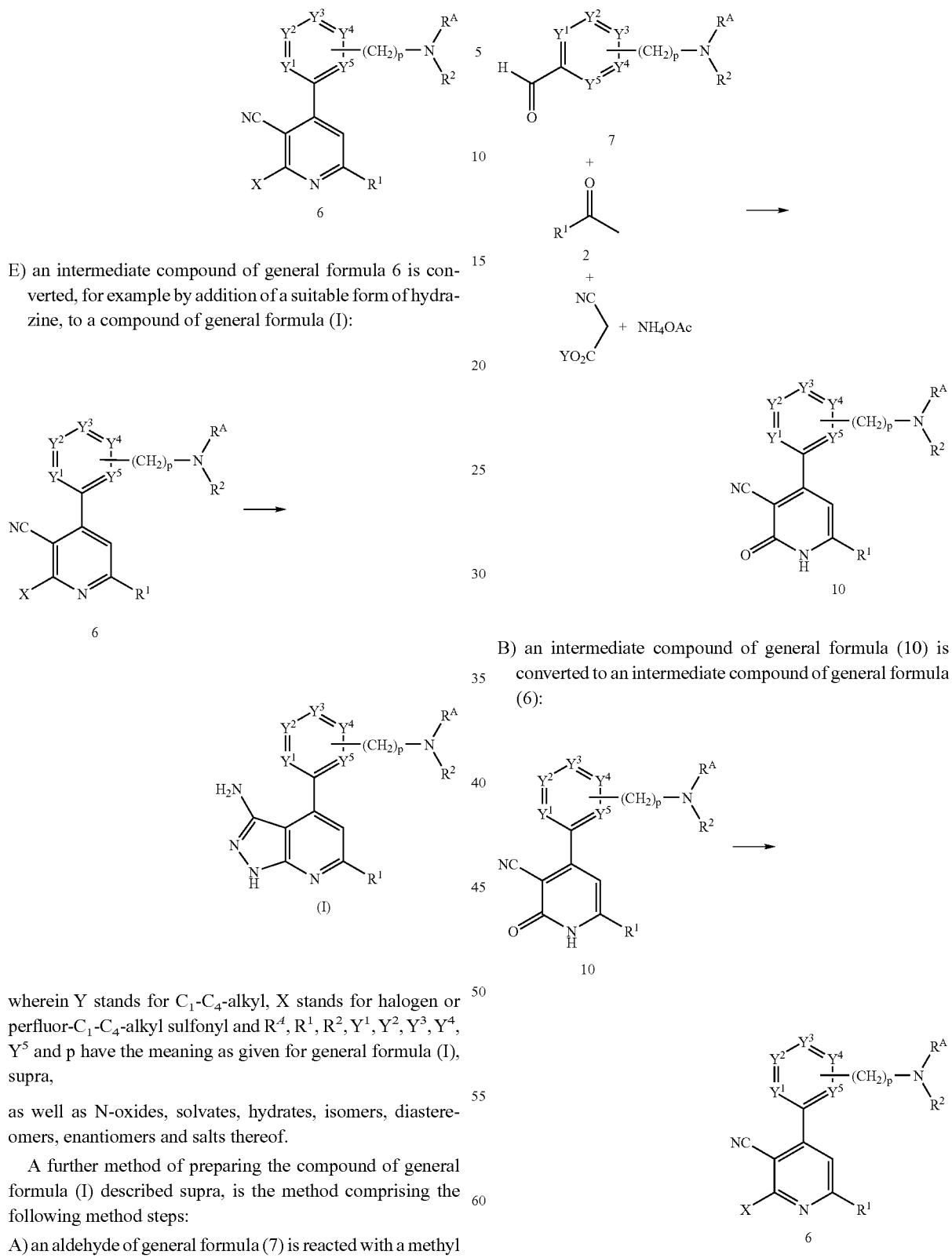

E) an intermediate compound of general formula 6 is converted, for example by addition of a suitable form of hydrazine, to a compound of general formula (I):

wherein Y stands for $C_1$-$C_4$-alkyl, X stands for halogen or perfluor-$C_1$-$C_4$-alkyl sulfonyl and $R^A$, $R^1$, $R^2$, $Y^1$, $Y^2$, $Y^3$, $Y^4$, $Y^5$ and p have the meaning as given for general formula (I), supra, as well as N-oxides, solvates, hydrates, isomers, diastereomers, enantiomers and salts thereof.

A further method of preparing the compound of general formula (I) described supra, is the method comprising the following method steps:

A) an aldehyde of general formula (7) is reacted with a methyl ketone of general formula (2), an alkyl cyanoacetate and a suitable ammonium salt, preferably ammonium acetate, to produce an intermediate compound of general formula (10):

B) an intermediate compound of general formula (10) is converted to an intermediate compound of general formula (6):

C) an intermediate compound of general formula (6) is converted to a compound of general formula (I) as described above:

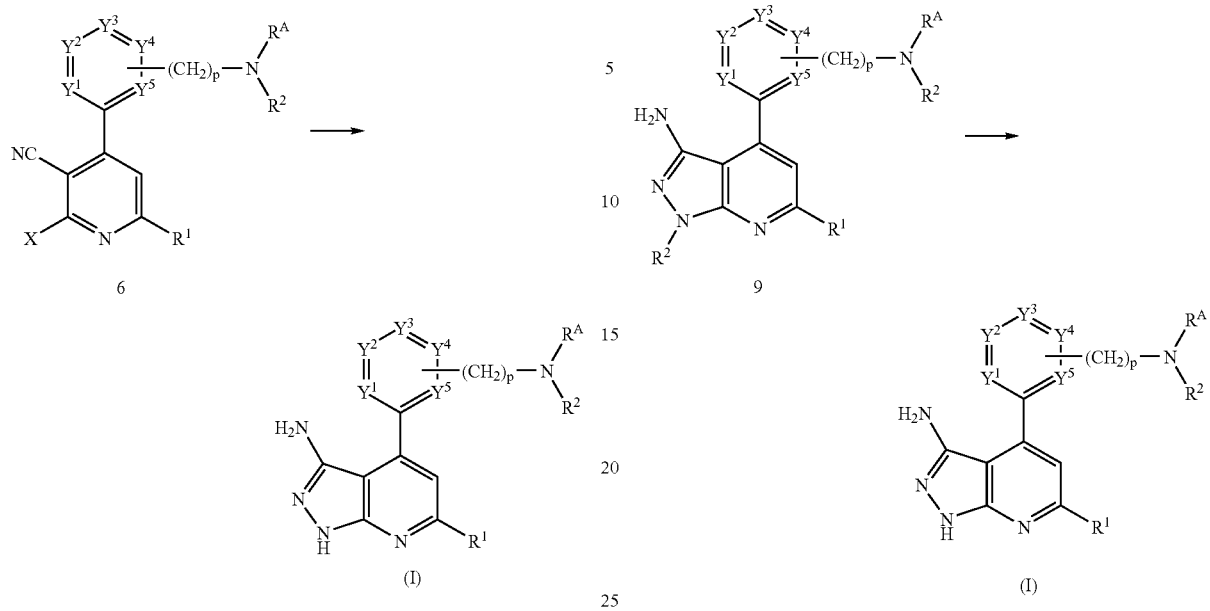

wherein Y stands for $C_1$-$C_4$-alkyl, X stands for halogen or perfluor-$C_1$-$C_4$-alkyl sulfonyl and $R^A$, $R^1$, $R^2$, $Y^1$, $Y^2$, $Y^3$, $Y^4$, $Y^5$ and p have the meaning given for general formula (I), supra, as well as N-oxides, solvates, hydrates, isomers, diastereomers, enantiomers and salts thereof.

A further method of preparing pyrazolopyridines of general formula (I) described supra, is the method comprising the following method steps:

A) an intermediate compound of general formula 8 is converted to an intermediate compound of general formula 9:

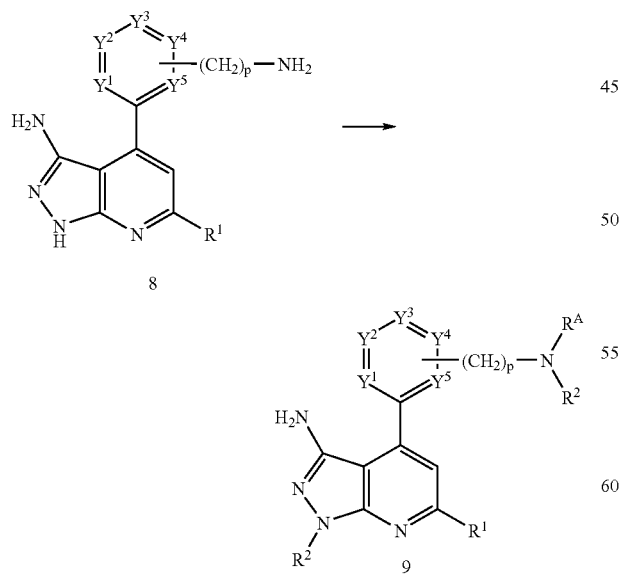

B) an intermediate compound of formula 9 is converted to a compound of general formula (I):

wherein $R^A$, $R^1$, $R^2$, $Y^1$, $Y^2$, $Y^3$, $Y^4$, $Y^5$ and p have the meaning described in general formula (I) supra, as well as N-oxides, solvates, hydrates, isomers, diastereomers, enantiomers and salts thereof.

In accordance with a further embodiment, the present invention relates to a compound of general formula (6):

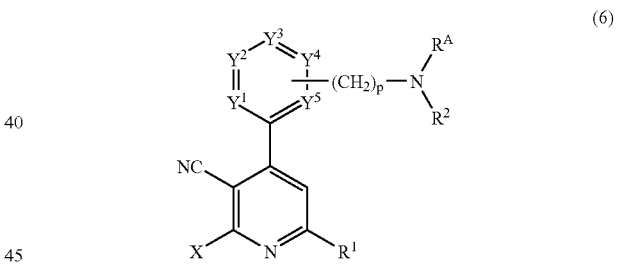

wherein Y stands for $C_1$-$C_4$-alkyl, X stands for halogen or perfluor-$C_1$-$C_4$-alkyl sulfonyl and $R^A$, $R^1$, $R^2$, $Y^1$, $Y^2$, $Y^3$, $Y^4$, $Y^5$ and p have the meaning as given for general formula (I) as defined supra, wherein when X stands for Cl, $R^1$ is not p-chlorophenyl, and $R^A$ and $R^2$ are both not $CH_3$.

Further another embodiment of the present invention relates to the use of a compound of general formula (6) as mentioned supra for the preparation of a compound of general formula (I) as defined supra.

The compounds of the present invention can be used in treating diseases of dysregulated vascular growth or diseases which are accompanied with dysregulated vascular growth. Especially, the compounds effectively interfere with angiopoietin and therefore influence Tie2 signalling. Surprisingly, the compounds block Tie2 signalling, whilst showing less deleterious pharmacological activity. This effect will therefore allow prolonged treatment of patients with the inventive compounds offering good tolerability and high anti-angiogenic efficacy, where persistent angiogenesis plays a pathological role.

Therefore, another aspect of the present invention is a use of the compound of general formula (I) described supra for manufacturing a pharmaceutical composition for the treatment of diseases of dysregulated vascular growth or of diseases which are accompanied with dysregulated vascular growth.

Preferably, the use is in the treatment of diseases, wherein the diseases are tumours and/or metastases thereof.

Another use is in the treatment of diseases, wherein the diseases are retinopathy, other angiogenesis dependent diseases of the eye, in particular cornea transplant rejection or age-related macular degeneration, rheumatoid arthritis, and other inflammatory diseases associated with angiogenesis, in particular psoriasis, delayed type hypersensitivity, contact dermatitis, asthma, multiple sclerosis, restenosis, pulmonary hypertension, stroke, and diseases of the bowel.

A further use is in the treatment of diseases, wherein the diseases are coronary and peripheral artery disease.

Another use is in the treatment of diseases, wherein the diseases are ascites, oedema such as brain tumour associated oedema, high altitude trauma, hypoxia induced cerebral oedema pulmonary oedema and macular oedema or oedema following burns and trauma, chronic lung disease, adult respiratory distress syndrome, bone resorbtion and for benign proliferating diseases such as myoma, benign prostate hyperplasia and wound healing for the reduction of scar formation, reduction of scar formation scar formation during regeneration of damaged nerves, endometriosis, pre-eclampsia, postmenopausal bleeding and ovarian hyperstimulation.

A further use is in the treatment of diseases, wherein the diseases are retinopathy, other angiogenesis dependent diseases of the eye, rheumatoid arthritis, and other inflammatory diseases associated with angiogenesis.

Yet another aspect of the invention is a method of treating a disease of dysregulated vascular growth or diseases which are accompanied with dysregulated vascular growth, by administering an effective amount of a compound of general formula (I) described supra.

Preferably, the diseases of said method is tumour and/or metastases thereof.

Also, the diseases of said method are retinopathy, other angiogenesis dependent diseases of the eye, in particular cornea transplant rejection or age-related macular degeneration, e.g. rheumatoid arthritis, and other inflammatory diseases associated with angiogenesis, in particular psoriasis, delayed type hypersensitivity, contact dermatitis, asthma, multiple sclerosis, restenosis, pulmonary hypertension, stroke, and diseases of the bowel.

Further, the disease of the method are coronary and peripheral artery disease.

Other diseases of the method are ascites, oedema such as brain tumour associated oedema, high altitude trauma, hypoxia induced cerebral oedema pulmonary oedema and macular oedema or oedema following burns and trauma, chronic lung disease, adult respiratory distress syndrome, bone resorbtion and for benign proliferating diseases such as myoma, benign prostate hyperplasia and wound healing for the reduction of scar formation, reduction of scar formation scar formation during regeneration of damaged nerves, endometriosis, pre-eclampsia, postmenopausal bleeding and ovarian hyperstimulation.

The compounds of the present invention can thus be applied for the treatment of diseases accompanied by neoangiogenesis. This holds principally for all solid tumours, e.g. breast, colon, renal, lung and/or brain tumours or metastases thereof and can be extended to a broad range of diseases, where pathologic angiogenesis is persistent. This applies for diseases with inflammatory association, diseases associated with oedema of various forms and diseases associated with stromal proliferation and pathologic stromal reactions broadly. Particularly suited is the treatment for gynaecological diseases where inhibition of angiogenic, inflammatory and stromal processes with pathologic character can be inhibited. At the same time the toxic side effects on normal proliferating tissue are low. The treatment is therefore an addition to the existing armament to treat diseases associated with neoangiogenesis.

The compounds of the present invention can be used in particular in therapy and prevention of tumour growth and metastases, especially in solid tumours of all indications and stages with or without pre-treatment if the tumour growth is accompanied with persistent angiogenesis. However, it is not restricted to tumour therapy but is also of great value for the treatment of other diseases with dysregulated vascular growth. This includes retinopathy and other angiogenesis dependent diseases of the eye (e.g. cornea transplant rejection, age-related macular degeneration), rheumatoid arthritis, and other inflammatory diseases associated with angiogenesis such as psoriasis, delayed type hypersensitivity, contact dermatitis, asthma, multiple sclerosis, restenosis, pulmonary hypertension, stroke and inflammatory diseases of the bowel, such as Crohn's disease. It includes coronary and peripheral artery disease. It can be applied for disease states such as ascites, oedema, such as brain tumour associated oedema, high altitude trauma, hypoxia induced cerebral oedema, pulmonary oedema and macular oedema or oedema following burns and trauma. Furthermore, it is useful for chronic lung disease, adult respiratory distress syndrome. Also for bone resorption and for benign proliferating diseases such as myoma, benign prostate hyperplasia and wound healing for the reduction of scar formation. It is therapeutically valuable for the treatment of diseases, where deposition of fibrin or extracellular matrix is an issue and stroma proliferation is accelerated (e.g. fibrosis, cirrhosis, carpal tunnel syndrome etc). In addition it can be used for the reduction of scar formation during regeneration of damaged nerves, permitting the reconnection of axons. Further uses are endometriosis, pre-eclampsia, postmenopausal bleeding and ovarian hyperstimulation.

Another aspect of the present invention is a pharmaceutical composition which contains a compound of Formula (I) or pharmaceutically acceptable salts thereof, N-oxides, solvates, hydrates, isomers or mixtures of isomers thereof, in admixture with one or more suitable excipients. This composition is particularly suited for the treatment of diseases of dysregulated vascular growth or of diseases which are accompanied with dysregulated vascular growth as explained above.

In order that the compounds of the present invention be used as pharmaceutical products, the compounds or mixtures thereof may be provided in a pharmaceutical composition, which, as well as the compounds of the present invention for enteral, oral or parenteral application contain suitably pharmaceutically acceptable organic or inorganic inert base material, e.g. purified water, gelatin, gum Arabic, lactate, starch, magnesium stearate, talcum, vegetable oils, polyalkylenglycol, etc.

The pharmaceutical compositions of the present invention may be provided in a solid form, e.g. as tablets, dragées, suppositories, capsules or in liquid form, e.g. as a solution, suspension or emulsion. The pharmaceutical composition may additionally contain auxiliary substances, e.g. preservatives, stabilisers, wetting agents or emulsifiers, salts for adjusting the osmotic pressure or buffers.

For parenteral applications, (including intravenous, subcutaneous, intramuscular, intravascular or infusion), sterile injection solutions or suspensions are preferred, especially aqueous solutions of the compounds in polyhydroxyethoxy containing castor oil.

The pharmaceutical compositions of the present invention may further contain surface active agents, e.g. salts of gallenic acid, phosphorlipids of animal or vegetable origin, mixtures thereof and liposomes and parts thereof.

For oral application tablets, dragées or capsules with talcum and/or hydrocarbon-containing carriers and binders, e.g. lactose, maize and potato starch, are preferred. Further application in liquid form is possible, for example as juice, which contains sweetener if necessary.

The dosage will necessarily be varied depending upon the route of administration, age, weight of the patient, the kind and severity of the illness being treated and similar factors. The daily dose is in the range of 0.5 to 1,500 mg. A dose can be administered as unit dose or in part thereof and distributed over the day. Accordingly the optimum dosage may be determined by the practitioner who is treating any particular patient.

Another aspect of the present invention is a method which may be used for preparing the compounds according to the present invention.

The following Table lists the abbreviations used in this paragraph, and in the Examples section. NMR peak forms are stated as they appear in the spectra, possible higher order effects have not been considered.

| Abbreviation | Meaning |
| --- | --- |
| $\alpha_D^{20}$ | Specific optical rotation. Measured on a Perkin-Elmer 343 polarimeter, referenced to the sodium D line at 589 nM and measured at 20° C., unless otherwise stated. The concentration, c, of the |

-continued

| Abbreviation | Meaning |
| --- | --- |
| | solution, in g/100 mL solvent, plus the solvent used, is given with the data in parentheses. |
| Ac | acetyl |
| Boc | tert-butyloxycarbonyl |
| br | broad |
| c- | cyclo- |
| CI | chemical ionisation |
| d | doublet |
| dd | doublet of doublets |
| DCM | dichloromethane |
| DIPEA | N,N-diisopropylethylamine |
| DMF | N,N-dimethylformamide |
| DMSO | dimethyl sulfoxide |
| eq | Equivalent |
| ESI | electrospray ionisation: results for the observed ions are reported as a mass/charge (m/z) ratio |
| GP | general procedure |
| hep | heptet |
| m | multiplet |
| mc | centred multiplet |
| Mp. | Melting point in ° C. |
| MS | mass spectrometry |
| NMR | nuclear magnetic resonance spectroscopy: chemical shifts (□) are given in ppm. |
| POPd | dihydrogen dichlorobis(di-tert-butyl phosphinito-κP)palladate(2); CombiPhos Catalysts, Inc. |
| q | quartet |
| s | singlet |
| t | triplet |
| TEA | triethylamine |
| TFA | trifluoroacetic acid |
| THF | tetrahydrofuran |

The following schemes and general procedures illustrate general synthetic routes to the compounds of the invention and are not intended to be limiting. Specific examples are described in the subsequent paragraph.

A first reaction scheme is outlined infra:

Synthesis of Compounds of General Formula (I)

Scheme 1

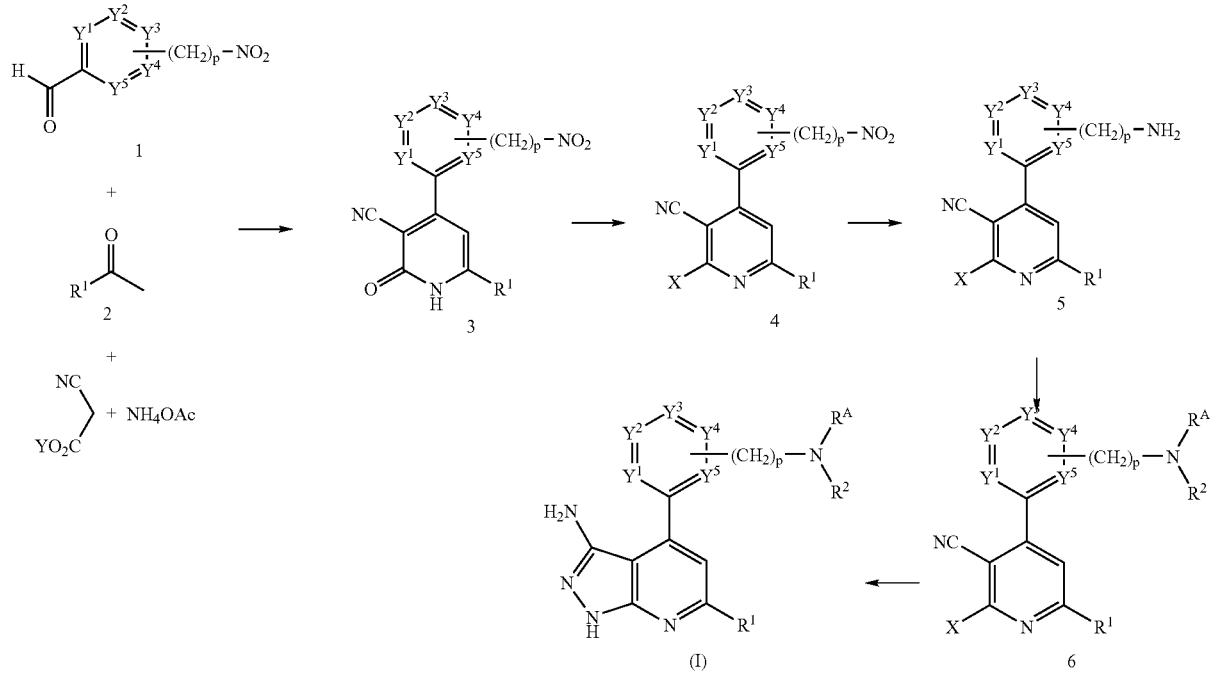

wherein Y stands for $C_1$-$C_4$-alkyl, X stands for halogen or perfluor-$C_1$-$C_4$-alkyl sulfonyl and $R^A$, $R^1$, $R^2$, $Y^1$, $Y^2$, $Y^3$, $Y^4$, $Y^5$ and p have the meaning as given for general formula (I).

Compounds of general formula (I) can be synthesised according to the procedure depicted in Scheme 1. Reaction of an aldehyde of general formula 1 with a methyl ketone of general formula 2, an alkyl cyanoacetate, and a suitable ammonium salt, such as ammonium acetate for example, in a suitable solvent, such as ethanol for example, at temperatures upto the boiling point of the solvent, whereby in the case of ethanol 80° C. is preferred, yields intermediate compounds of general formula 3. Conversion of intermediate compounds of general formula 3 into intermediates of general formula 4 may be achieved by a variety of methods, e.g. when when X=Cl, reaction with phosphorus oxychloride, optionally in the presence of DMF, may be employed; or, for example, when X=trifluoromethanesulphonyl (TfO⁻), reaction with trifluoromethanesulphonic acid anhydride, in the presence of a suitable base, e.g. pyridine, which may also be used as solvent, optionally in the presence of an inert solvent, e.g. dichloromethane, at temperatures ranging from −20° C. to room temperature, whereby 0° C. up to room temperature is preferred, may be employed. Reduction of the nitro group in intermediate compounds of general formula (4) gives intermediate compounds of general formula (5). The person skilled in the art is well aware of many methods for nitro group reduction, whereby preferred is the reduction of intermediate compounds of general formula (4) with tin (II) chloride dihydrate in a suitable solvent, e.g. is ethanol, at temperatures ranging from room temperature to the boiling point of the solvents, whereby in the case of ethanol 80° C. is preferred. Intermediate compounds of general formula (6) are formed from intermediate compounds of general formula (5) by reaction with, for example, a suitably functionalised isocyanate, sulfonyl chloride or acid chloride, in the presence of a suitable base as necessary, e.g. pyridine, which may also be used as solvent, optionally in the presence of an inert solvent, e.g. dichloromethane, at temperatures ranging from −20° C. to room temperature, whereby room temperature is preferred, may be employed. The person skilled in the art is well aware of alternative methods of forming ureas, sulphonamides or amides. In the case of ureas, carbamoyl chlorides or arylcarbamates may provide useful starting materials. Ureas may also be formed from suitably functionalised amines and suitable phosgene equivalents, whereby carbonyl diimidazole chemistry may be also be employed. In the case of amide formation, it is also possible to start from the corresponding ester. The ester may be reacted according to a method described in *J. Org. Chem.* 1995, 8414 with trimethylaluminium and the corresponding amine in suitable solvents such as toluene, at temperatures of 0° C. to the boiling point of the solvent. If the molecule contains two ester groups, both are converted into the same amide. Instead of trimethylaluminium, sodium hexamethyldisilazide can also be used. For amide formation, however, all processes that are known from peptide chemistry are also available. For example, the corresponding acid, obtained from the corresponding ester by saponification, can be reacted with the amine in aprotic polar solvents, such as, for example, dimethylformamide, via an activated acid derivative, which is obtainable, for example, with hydroxybenzotriazole and a carbodiimide, such as, for example, diisopropylcarbodiimide, at temperatures of between 0° C. and the boiling point of the solvent, preferably at 80° C., or else with preformed reagents, such as, for example, O-(7-azabenzotriazol-1-yl)-1,1,3,3-tetramethyluronium hexafluorophosphate (HATU) (*Chem. Comm.* 1994, 201), at temperatures of between 0° C. and the boiling point of the solvent, preferably at room temperature. The addition of a suitable base such as N-methylmorpholine, for example, is necessary. Amide formation, may also be accomplished via the acid halide, mixed acid anhydride, imidazolide or azide.

Reaction of intermediate compounds of general formula (6) with hydrazine hydrate in a suitable solvent eg n-propanol at temperatures from room temperature upto the boiling point of the solvent, whereby in the case of n-PrOH 100° C. is preferred, leads to compounds of general formula (I).

The substituents $Y^1$, $Y^2$, $Y^3$, $Y^4$, $Y^5$, $R^1$, $R^A$, $R^2$ may be further modified on each step [(general formula 3 to general formula 6)] or in the last step [(general formula (I))]. These modifications can be such as the introduction of protecting groups, cleavage of protecting groups, reduction or oxidation of functional groups, substitution or other reactions. Appropriate protecting groups, their introduction are well-known to the person skilled in the art. The sequence shown in Scheme 1 can be also changed in a way that modifications or introduction of the substituents are performed earlier or later.

In particular, the introduction of substituents $R^A$ and $R^2$ can be performed earlier or later. It is possible, that for example aldehydes of general formula 1 already contain the the group $(CH_2)_p NR^A R^2$ instead of $(CH_2)_p NO_2$. On the other hand, it is also possible for example to introduce $R^2$ after the pyrazole ring has been formed. In certain cases double addition occurs and compounds of general formula 9 (Scheme 2) are obtained. In these cases, a selective cleavage of the group $R^2$ at pyrazole nitrogen 1 can be achieved for example by treatment of the compound of general formula 9 with potassium carbonate in methanol to give compounds of general formula (I).

In particular, in the context of the production of compounds of general formula (I), the introduction of substituents $R^A$ and $R^2$ can be performed earlier. In such cases the aldehyde of general formula (1) in scheme 1 is replaced by an aldehyde of general formula (7) and analogous chemistry leads to compounds of general formula (I).

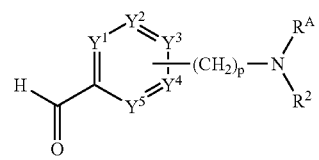

7 wherein $R^A$, $R^2$, $Y^1$, $Y^2$, $Y^3$, $Y^4$, $Y^5$ and p have the meaning as given for general formula (I).

A second reaction scheme is outlined below:

Synthesis of Compounds of General Formula (I)

Scheme 2

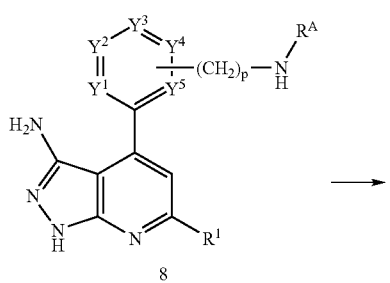

8

-continued

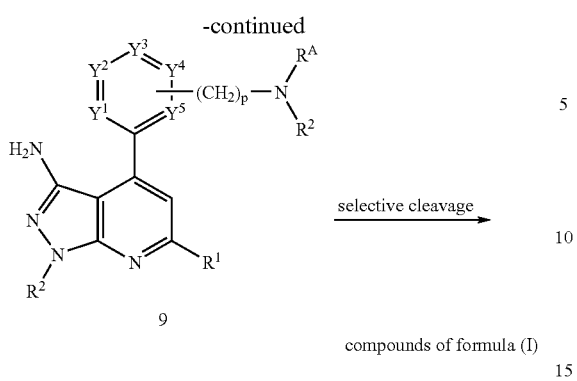

compounds of formula (I)

The substituents $Y^1$, $Y^2$, $Y^3$, $Y^4$, $Y^5$, $R^1$, $R^A$, $R^2$ and p have the same meaning as given for the general formula 1. In addition, functional groups may be protected. Possible protecting groups are ketals/acetals, esters, amides, nitro groups, carbamates, alkyl ethers, allyl ethers, benzyl ethers, or silyl ethers such as, for example, trimethylsilyl, tert-butyldimethylsilyl, tert-butyl-diphenylsilyl, triethylsilyl.

Scheme 2 illustrates yet another strategy for the synthesis of compounds of general formula (I) in which $R^2$ is introduced after the pyrazole ring has been formed. It will be apparent to the person skilled in the art that in certain cases, double addition may occur and compounds of general formula (9) (Scheme 2) are obtained. In these cases, a selective cleavage of the group $R^2$ at pyrazole nitrogen 1 may be achieved for example by treatment of intermediate compounds of general formula (9) with a suitable base, such as potassium carbonate, in a suitable solvent, such as methanol, to give compounds of general formula (I).

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallisation. In some cases, impurities may be stirred out using a suitable solvent. In some cases, the compounds may be purified by chromatography, particularly flash chromatography, using for example prepacked silica gel cartridges, e.g. from Separtis such as Isolute® Flash silica get or Isolute® Flash NH2 silica gel in combination with a Flashmaster II autopurifier (Biotage) and eluants such as gradients of hexane/EtOAc or DCM/ethanol. In some cases, the compounds may be purified by preparative HPLC using for example a Waters autopurifier equipped with a diode array detector and/or on-line electrospray ionization mass spectrometer in combination with a suitable prepacked reverse phase column and eluants such as gradients of water and acetonitrile which may contain additives such as trifluoroacetic acid or aqueous ammonia.

EXAMPLE 1

Figure 1:
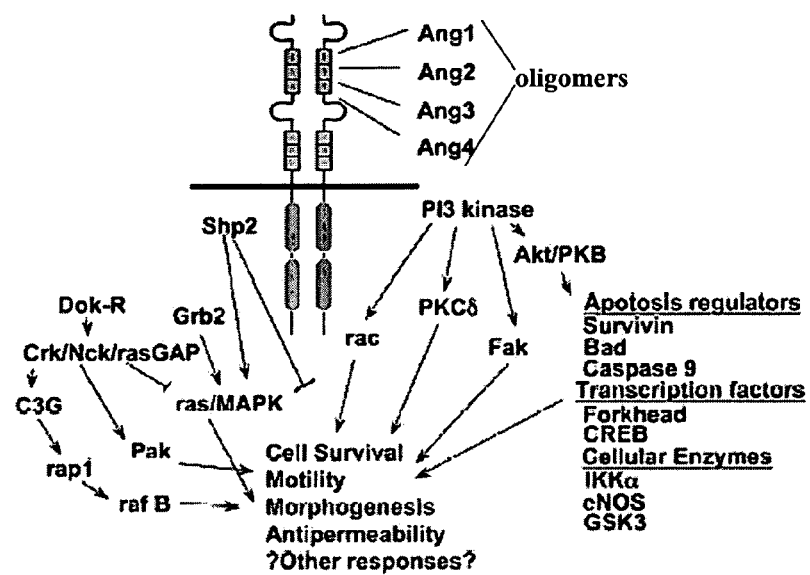
FIG. 1 illustrates an overview of the mechanism of Tie2 signalling.

Preparation of 1-[4-(3-amino-6-tert-butyl-1H-pyrazolo[3,4-b]pyridin-4-yl)-phenyl]-3-phenyl-urea

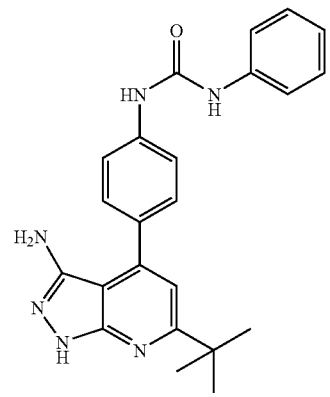

EXAMPLE 1a

Preparation of 1-(4-hydroxymethyl-phenyl)-3-phenylurea

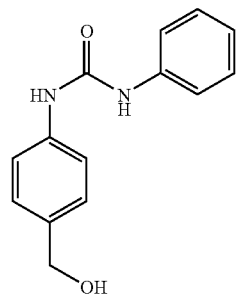

A solution of 3.75 g 4-aminobenzylalcohol and 3.3 ml isocyanato-benzene in 120 ml dichloromethane was stirred at 23° C. for 2 hours. Afterwards, the reaction mixture was filtered. The crystalline product was washed with diethyl-ether. 6.82 g product was obtained which was used without further purification.

$^1$H-NMR (d6-DMSO): δ=4.40 (2H); 5.06 (1H); 6.96 (1H); 7.16-7.32 (4H); 7.35-7.52 (4H); 8.63 (2H) ppm.

EXAMPLE 1b

Preparation of 1-(4-formyl-phenyl)-3-phenyl-urea

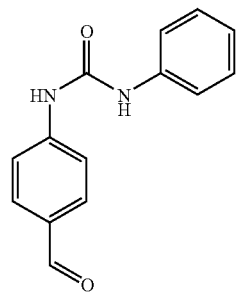

A solution of 3.41 g 1a and 10 g manganese dioxide in toluene was stirred at 23° C. for 20 hours. Afterwards, the

EXAMPLE 1c

Preparation of 1-[4-(6-tert-butyl-3-cyano-2-oxo-1,2-dihydro-pyridin-4-yl)-phenyl]-3-phenyl-urea

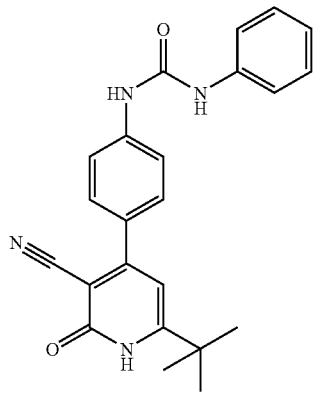

A solution of 6.66 g ammonium acetate, 1.14 ml methyl cyanoacetate, 1.32 ml 3,3-dimethylbutan-2-one, and 2.57 g 1b in 100 ml ethanol was stirred at 80° C. for 6 hours. Afterwards, it was cooled to 23° C. and the precipitated product was obtained by filtration. The product was purified by recrystallisation from methylene chloride/methanol. 1.44 g product was isolated.

$^1$H-NMR (d6-DMSO): δ=1.30 (9H); 6.25 (2H); 6.99 (1H); 7.29 (2H); 7.46 (2H); 7.13 (4H); 8.79 (1H); 9.02 (1H); 12.18 (1H) ppm.

EXAMPLE 1d

Preparation of trifluoromethanesulfonic acid 6-tert-butyl-3-cyano-4-[4-(3-phenyl-ureido)-phenyl]-pyridin-2-yl ester

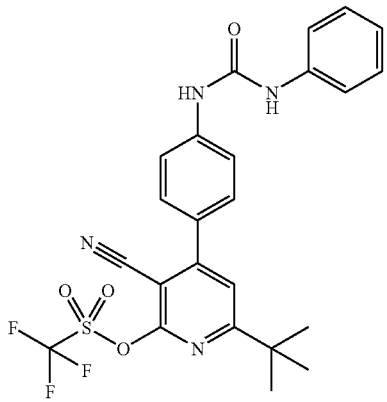

A solution of 340 mg 1c and 300 μl trifluoromethane-sulfonic acid anhydride in pyridine was stirred at 0° C. for 3 hours. Afterwards, the reaction mixture was poured into a saturated aqueous sodium hydrogen carbonate solution. It was extracted with ethyl acetate and the organic layer was washed with brine. It was dried over sodium sulfate and evaporated in vacuo. The crude product was purified by column chromatography on silica gel. 116 mg product was obtained.

$^1$H-NMR (d6-DMSO): δ=1.36 (9H); 7.00 (1H); 7.29 (2H); 7.47 (2H); 7.65-7.85 (5H); 8.80 (1H); 9.07 (1H) ppm.

EXAMPLE 1e

Preparation of 1-[4-(3-amino-6-tert-butyl-1H-pyrazolo[3,4-b]pyridin-4-yl)-phenyl]-3-phenyl-urea

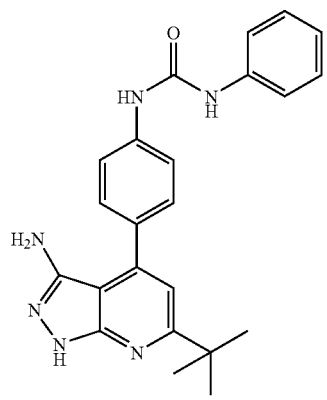

A solution of 78 mg 1d and 30 μl hydrazine hydrate (80%) in propanol was stirred at 100° C. for 3 hours. Afterwards, the reaction mixture was cooled to 0° C. and left at this temperature for 2 hours. Then, the precipitated product was isolated by filtration. The product was washed with ice-cold propanol and dried at 50° C. in vacuo. The crude product was purified by column chromatography on silica gel. 25 mg product was isolated.

$^1$H-NMR (d6-DMSO): δ=1.39 (9H); 4.52 (2H); 6.93-7.03 (2H); 7.29 (2H); 7.44-7.58 (4H); 7.65 (2H); 8.81 (1H); 8.99 (1H); 12.12 (1H) ppm.

EXAMPLE 2

Preparation of N-[4-(3-amino-6-tert-butyl-1H-pyrazolo[3,4-b]pyridin-4-yl)-phenyl]-benzenesulfonamide

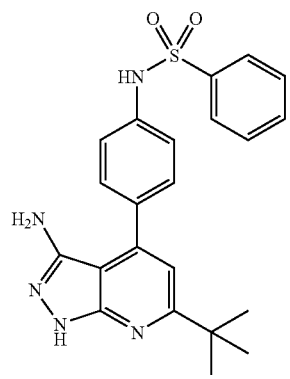

EXAMPLE 2a

Preparation of
n-(4-hydroxymethyl-phenyl)-benzenesulfonamide

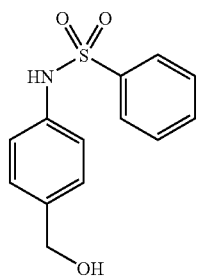

A solution of 500 mg (4-aminophenyl)-methanol, 1.7 ml triethylamine, and 780 µl benzenesulfonyl chloride in 10 ml tetrahydrofuran was stirred at 23° C. for 17 hours. Afterwards, the reaction mixture was poured into ice-old hydrochloric acid. It was stirred for 10 minutes and then extracted with ethyl acetate. The organic Layer was washed with brine and dried over sodium sulfate. The crude product was purified by column chromatography on silica gel. 572 mg product was isolated.

$^1$H-NMR (CDCl$_3$): δ=4.62 (2H); 6.68 (2H); 7.05 (2H); 7.24 (2H); 7.40-7.48 (2H); 7.54 (1H); 7.77 (2H) ppm.

EXAMPLE 2b

Preparation of
N-(4-formyl-phenyl)-benzenesulfonamide

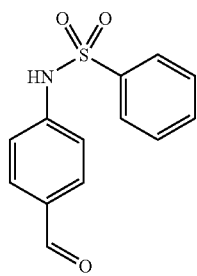

A solution of 303 mg 2a, 260 mg 4-methyl-morpholine 4-oxide, and 22 mg tetrapropylammonium perruthenate in dichloromethane was stirred with molecular sieves (4 Å) at 23° C. for 17 hours. Afterwards, it was filtered and the filtrate was evaporated in vacuo. The crude product was purified by column chromatography on silica gel. 234 mg product was isolated.

$^1$H-NMR (CDCl$_3$): δ=7.23 (2H); 7.35-7.65 (4H); 7.78 (2H); 7.89 (2H); 9.89 (1H) ppm.

EXAMPLE 2c

Preparation of N-[4-(6-tert-butyl-3-cyano-2-oxo-1,2-dihydro-pyridin-4-yl)-phenyl]-benzenesulfonamide

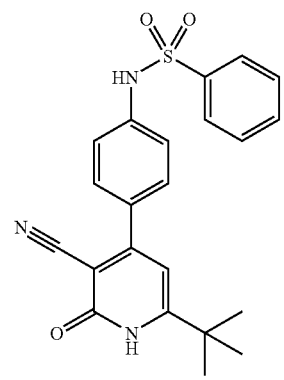

In analogy to the procedure described for Example 1c reaction of 1.16 g ammonium acetate, 200 µl methyl cyanoacetate, 235 µl 3,3-dimethylbutan-2-one, and 492 mg of 2b yielded 237 mg product.

$^1$H-NMR (d6-DMSO): δ=1.26 (9H); 6.18 (1H); 7.23 (2H); 7.52-7.70 (5H); 7.86 (2H); 10.80 (1H); 12.22 (1H) ppm.

EXAMPLE 2d

Preparation of trifluoromethanesulfonic acid 4-(4-benzenesulfonylamino-phenyl)-6-tert-butyl-3-cyano-pyridin-2-yl ester

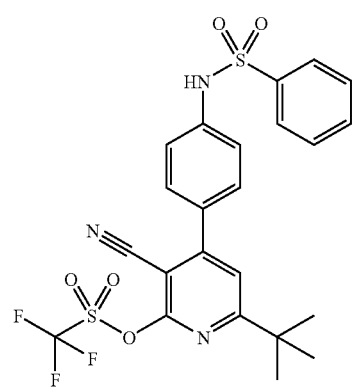

In analogy to the procedure described for Example 1d reaction of 193 mg 2c and 240 µl trifluoromethanesulfonic acid anhydride in pyridine yielded 219 mg product.

$^1$H-NMR (CDCl$_3$): δ=1.36 (9H); 7.22-7.35 (4H); 7.45-7.60 (2H); 7.69 (1H); 7.86 (1H); 8.62 (2H) ppm.

EXAMPLE 2e

Preparation of N-[4-(3-amino-6-tert-butyl-1H-pyrazolo[3,4-b]pyridin-4-yl)-phenyl]-benzenesulfonamide

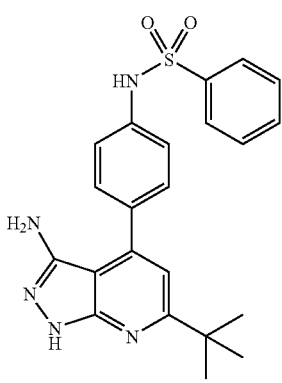

In analogy to the procedure described for Example 1e, reaction of 212 mg 2d and 72 µl hydrazine hydrate in propanol yielded 69 mg product.

$^1$H-NMR (d6-DMSO): δ=1.33 (9H); 4.40 (2H); 6.89 (1H); 7.25 (2H); 7.46 (2H); 7.52-7.68 (3H); 7.84 (2H); 10.52 (1H); 12.12 (1H) ppm.

EXAMPLE 3

Preparation of 1-[4-(3-amino-6-tert-butyl-1H-pyrazolo[3,4-b]pyridin-4-yl)-phenyl]-3-(3-fluoro-phenyl)-urea

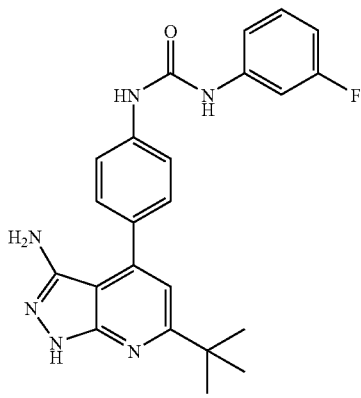

EXAMPLE 3a

Preparation of 6-tert-butyl-4-(4-nitro-phenyl)-2-oxo-1,2-dihydro-pyridine-3-carbonitrile

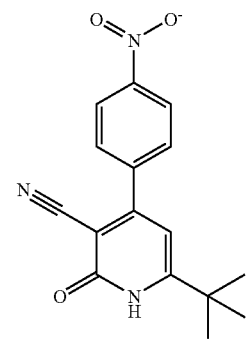

In analogy to the procedure described for Example 1c reaction of 41 g ammonium acetate, 7 ml methyl cyanoacetate, 8.2 ml 3,3-dimethylbutan-2-one, and 10 g 4-nitrobenzaldehyde yielded 4.71 g product.

$^1$H-NMR (d6-DMSO): δ=1.32 (9H); 6.30 (1H); 7.92 (2H); 8.39 (2H) ppm.

EXAMPLE 3b

Preparation of trifluoromethanesulfonic acid 6-tert-butyl-3-cyano-4-(4-nitro-phenyl)-pyridin-2-yl ester

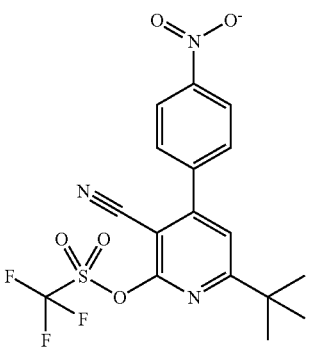

In analogy to the procedure described for Example 1d, reaction of 2.5 g 3a and 4.25 ml trifluoromethanesulfonic acid anhydride in pyridine yielded 3.01 g product.

$^1$H-NMR (CDCl$_3$): δ=1.41 (9H); 7.48 (1H); 7.78 (2H); 8.42 (2H) ppm.

EXAMPLE 3c

Preparation of trifluoromethanesulfonic acid 4-(4-amino-phenyl)-6-tert-butyl-3-cyano-pyridin-2-yl ester

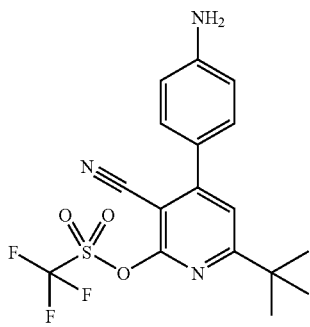

A solution of 3 g 3b and 8 g tin(II) chloride dihydrate in 50 ml ethanol was stirred at 70° C. for 10 minutes. Afterwards, the reaction mixture was poured into 120 ml of an aqueous solution of ammonia (33%). It was stirred for 45 minutes at 23° C. Afterwards, it was extracted with ethyl acetate. The organic layer was washed with brine, dried over sodium sulfate and evaporated in vacuo. The crude product (2.6 g) was used without further purification.

$^1$H-NMR (d6-DMSO): δ=1.32 (9H); 5.96 (2H); 6.71 (2H); 7.54 (2H); 7.65 (1H) ppm.

EXAMPLE 3d

Preparation of trifluoromethanesulfonic acid 6-tert-butyl-3-cyano-4-{4-[3-(3-fluoro-phenyl)-ureido]-phenyl}-pyridin-2-yl ester

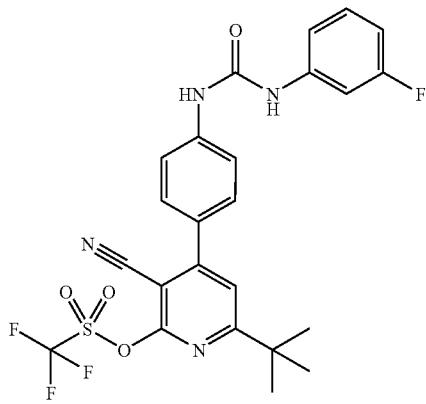

In analogy to the procedure described for Example 1a, reaction of 200 mg 3c and 60 μl 1-fluoro-3-isocyanato-benzene yielded 260 mg product.

$^1$H-NMR (d6-DMSO): δ=1.35 (9H); 6.80 (1H); 7.14 (1H); 7.30 (1H); 7.49 (1H); 7.66-7.85 (5H); 8.96 (1H); 9.13 (1H) ppm.

EXAMPLE 3e

Preparation of 1-[4-(3-amino-6-tert-butyl-1H-pyrazolo[3,4-b]pyridin-4-yl)-phenyl]-3-(3-fluoro-phenyl)-urea

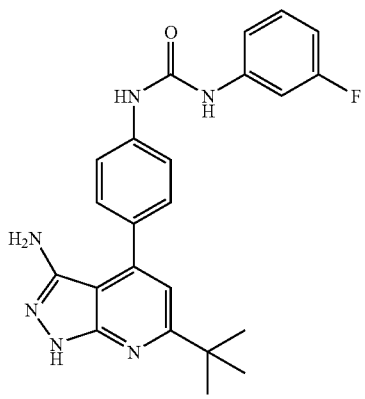

In analogy to the procedure described for Example 1e reaction of 260 mg 3d with 91 μl hydrazine hydrate in propanol yielded 141 mg product.

$^1$H-NMR (d6-DMSO): δ=1.38 (9H); 4.50 (2H); 6.79 (1H); 6.96 (1H); 7.15 (1H); 7.31 (1H); 7.49-7.60 (3H); 7.65 (2H); 8.98 (2H); 12.11 (1H) ppm.

EXAMPLE 4

Preparation of 1-[4-(3-amino-6-tert-butyl-1H-pyrazolo[3,4-b]pyridin-4-yl)-phenyl]-3-(2-fluoro-phenyl)-urea

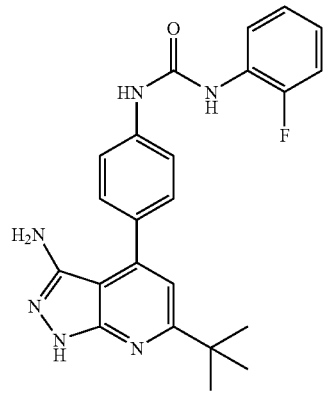

EXAMPLE 4a

Preparation of trifluoromethanesulfonic acid 6-tert-butyl-3-cyano-4-{4-[3-(2-fluoro-phenyl)-ureido]-phenyl}-pyridin-2-yl ester

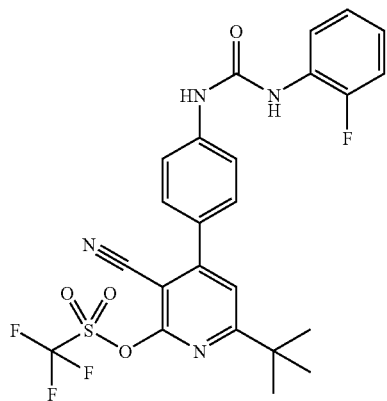

In analogy to the procedure described for Example 1a, reaction of 200 mg 3c and 60 µl 1-fluoro-2-isocyanato-benzene yielded 201 mg product.

$^1$H-NMR (d6-DMSO): δ=1.35 (9H); 7.03 (1H); 7.10-7.30 (2H); 7.69 (2H); 7.78 (3H); 8.16 (1H); 8.70 (1H); 9.45 (1H) ppm.

EXAMPLE 4b

Preparation of 1-[4-(3-amino-6-tert-butyl-1H-pyrazolo[3,4-b]pyridin-4-yl)-phenyl]-3-(2-fluoro-phenyl)-urea

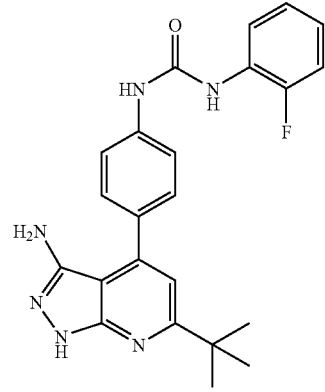

In analogy to the procedure described for Example 1e, reaction of 196 mg 4a with 70 µl hydrazine hydrate in propanol yielded 61 mg product.

$^1$H-NMR (d6-DMSO): δ=1.38 (9H); 4.50 (2H); 6.95 (1H); 7.04 (1H); 7.16 (1H); 7.26 (1H); 7.55 (2H); 7.66 (2H); 8.18 (1H); 8.62 (1H); 9.31 (1H); 12.10 (1H) ppm.

EXAMPLE 5

Preparation of 1-[4-(3-amino-6-tert-butyl-1H-pyrazolo[3,4-b]pyridin-4-yl)-phenyl]-3-(2,5-difluoro-phenyl)-urea

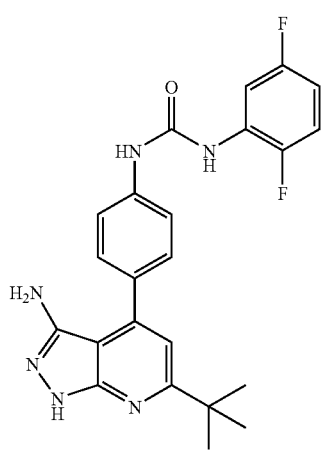

EXAMPLE 5a

Preparation of trifluoromethanesulfonic acid 6-tert-butyl-3-cyano-4-{4-[3-(2,5-difluoro-phenyl)-ureido]-phenyl}-pyridin-2-yl ester

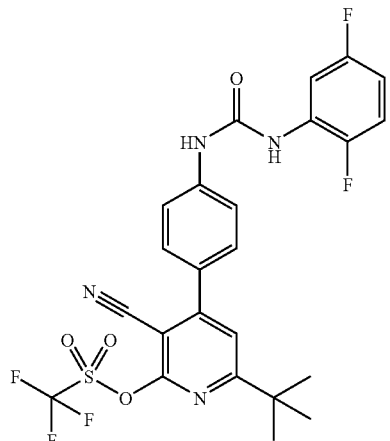

In analogy to the procedure described for Example 1a, reaction of 200 mg 3c and 71 µl 1-1,4-difluoro-2-isocyanato-benzene yielded 264 mg product.

$^1$H-NMR (d6-DMSO): δ=1.36 (9H); 6.85 (1H); 7.31 (1H); 7.70 (2H); 7.79 (3H); 8.04 (1H); 8.90 (1H); 9.50 (1H) ppm.

EXAMPLE 5b

Preparation of 1-[4-(3-amino-6-tert-butyl-1H-pyrazolo[3,4-b]pyridin-4-yl)-phenyl]-3-(2,5-difluorophenyl)-urea

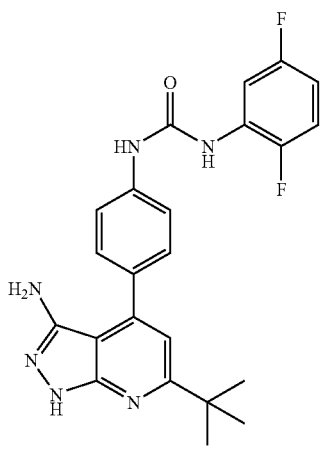

In analogy to the procedure described for Example 1e, reaction of 261 mg 5a with 90 µl hydrazine hydrate in propanol yielded 63 mg product.

$^1$H-NMR (d6-DMSO): δ=1.39 (9H); 4.51 (2H); 6.84 (1H); 6.96 (1H); 7.31 (1H); 7.58 (2H); 7.66 (2H); 8.06 (1H); 8.84 (1H); 9.38 (1H); 12.10 (1H) ppm.

EXAMPLE 6

Preparation of 1-[4-(3-amino-6-tert-butyl-1H-pyrazolo[3,4-b]pyridin-4-yl)-phenyl]-3-(3,4-difluorophenyl)-urea

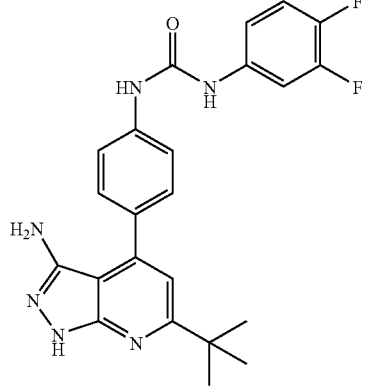

EXAMPLE 6a

Preparation of trifluoromethanesulfonic acid 6-tert-butyl-3-cyano-4-{4-[3-(3,4-difluoro-phenyl)-ureido]-phenyl}-pyridin-2-yl ester

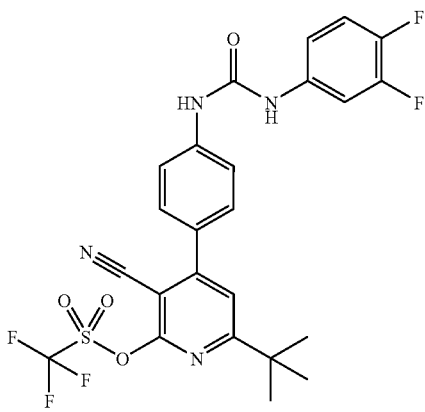

In analogy to the procedure described for Example 1a, reaction of 200 mg 3c and 71 µl 1,2-difluoro-4-isocyanatobenzene yielded 275 mg product.

$^1$H-NMR (d6-DMSO): δ=1.31 (9H); 7.12 (1H); 7.32 (1H); 7.60-7.78 (6H); 9.02 (1H); 9.14 (1H) ppm.

EXAMPLE 6b

Preparation of 1-[4-(3-amino-6-tert-butyl-1H-pyrazolo[3,4-b]pyridin-4-yl)-phenyl]-3-(3,4-difluorophenyl)-urea

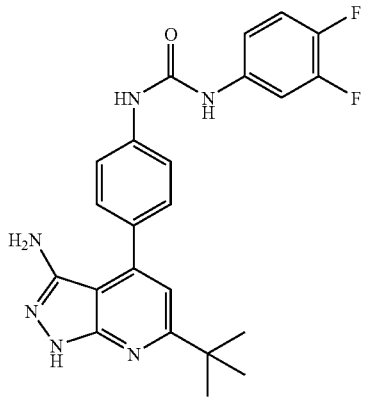

In analogy to the procedure described for Example 1e, reaction of 270 mg 6a with 91 µl hydrazine hydrate in propanol yielded 153 mg product.

$^1$H-NMR (d6-DMSO): δ=1.32 (9H); 4.46 (2H); 6.91 (1H); 7.11 (1H); 7.31 (1H); 7.50 (2H); 7.58-7.70 (3H) 8.95 (2H) ppm.

EXAMPLE 7

Preparation of 1-[4-(3-amino-6-tert-butyl-1H-pyrazolo[3,4-b]pyridin-4-yl)-phenyl]-3-naphthalen-1-yl-urea

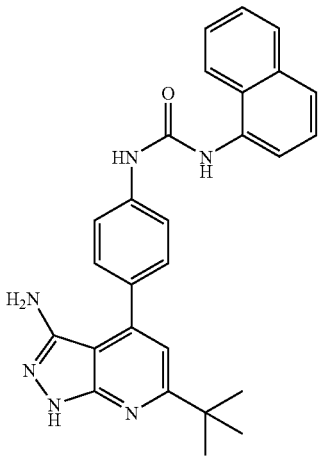

EXAMPLE 7a

Preparation of trifluoromethanesulfonic acid 6-tert-butyl-3-cyano-4-[4-(3-naphthalen-1-yl-ureido)-phenyl]-pyridin-2-yl ester

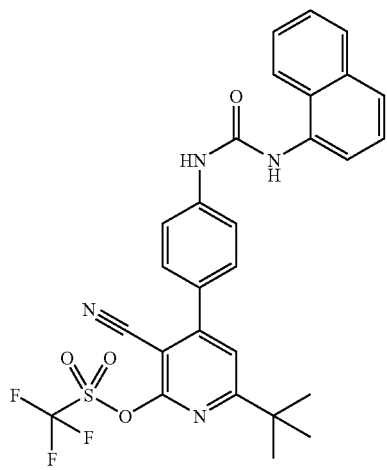

In analogy to the procedure described for Example 1a, reaction of 200 mg 3c and 80 μl 1-isocyanato-naphthalene yielded 283 mg product.

$^1$H-NMR (d6-DMSO): δ=1.31 (9H); 7.45 (1H); 7.50-7.62 (2H); 7.65 (1H); 7.70-7.80 (5H); 7.91 (1H); 7.98 (1H); 8.10 (1H); 8.88 (1H); 9.41 (1H) ppm.

EXAMPLE 7b

Preparation of 1-[4-(3-amino-6-tert-butyl-1H-pyrazolo[3,4-b]pyridin-4-yl)-phenyl]-3-naphthalen-1-yl-urea

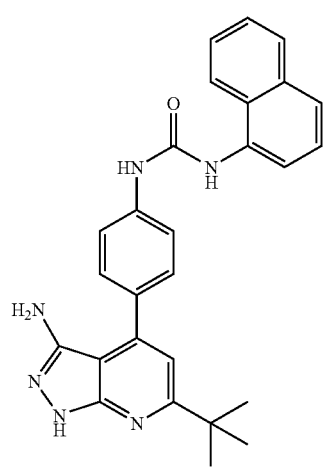

In analogy to the procedure described for Example 1e, reaction of 280 mg 7a with 91 μl hydrazine hydrate in propanol yielded 137 mg product.

$^1$H-NMR (d6-DMSO): δ=1.39 (9H); 4.51 (2H); 6.98 (1H); 7.45-7.78 (8H); 7.95 (1H); 8.02 (1H); 8.16 (1H); 8.84 (1H); 9.30 (1H); 12.12 (1H) ppm.

EXAMPLE 8

Preparation of 1-[4-(3-amino-6-tert-butyl-1H-pyrazolo[3,4-b]pyridin-4-yl)-phenyl]-3-naphthalen-2-yl-urea

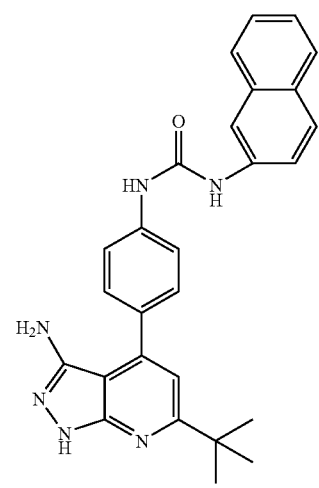

EXAMPLE 8a

Preparation of trifluoromethanesulfonic acid 6-tert-butyl-3-cyano-4-[4-(3-naphthalen-2-yl-ureido)-phenyl]-pyridin-2-yl ester

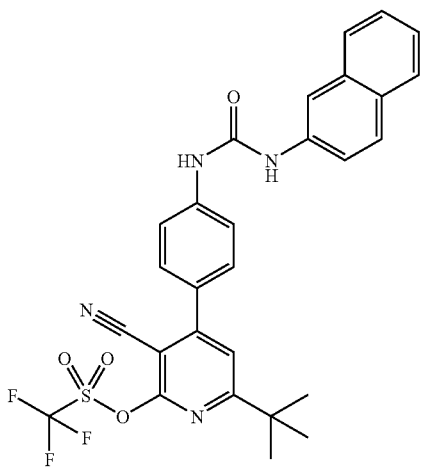

In analogy to the procedure described for Example 1a, reaction of 200 mg 3c and 93 mg 2-isocyanato-naphthalene yielded 234 mg product.

$^1$H-NMR (d6-DMSO): δ=1.32 (9H); 7.36 (1H); 7.45 (1H); 7.51 (1H); 7.70-7.90 (8H); 8.12 (1H); 9.06 (1H); 9.19 (1H) ppm.

EXAMPLE 8b

Preparation of 1-[4-(3-amino-6-tert-butyl-1H-pyrazolo[3,4-b]pyridin-4-yl)-phenyl]-3-naphthalen-2-yl-urea

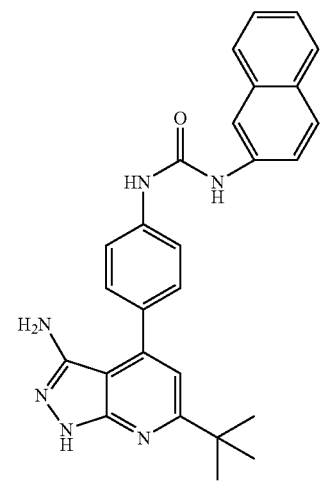

In analogy to the procedure described for Example 1e, reaction of 227 mg 8a with 75 μl hydrazine hydrate in propanol yielded 131 mg product.

$^1$H-NMR (d6-DMSO): δ=1.40 (9H); 4.52 (2H); 6.98 (1H); 7.38 (1H); 7.48 (1H); 7.56 (3H); 7.70 (2H); 7.78-7.90 (3H); 8.13 (1H); 9.00 (1H); 9.05 (1H); 12.12 (1H) ppm.

EXAMPLE 9

Preparation of 1-[4-(3-amino-6-tert-butyl-1H-pyrazolo[3,4-b]pyridin-4-yl)-phenyl]-3-m-tolyl-urea

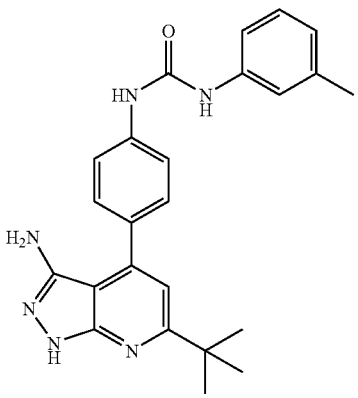

EXAMPLE 9a

Preparation of trifluoromethanesulfonic acid 6-tert-butyl-3-cyano-4-[4-(3-m-tolyl-ureido)-phenyl]-pyridin-2-yl ester

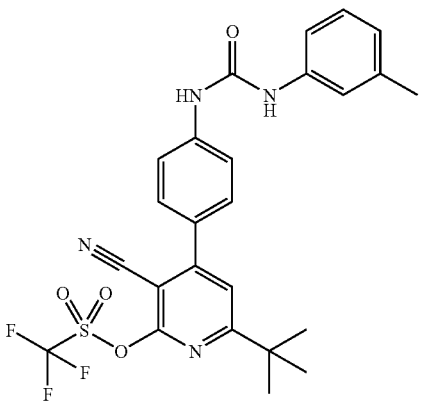

In analogy to the procedure described for Example 1a. reaction of 200 mg 3c and 70 pt 1-isocyanato-3-methyl-benzene yielded 244 mg product.

$^1$H-NMR (d6-DMSO): δ=1.38 (9H); 2.30 (3H); 6.71 (1H); 7.12-7.28 (2H); 7.32 (1H); 7.64-7.83 (5H); 8.71 (1H); 9.03 (1H) ppm.

EXAMPLE 9b

Preparation of 1-[4-(3-amino-6-tert-butyl-1H-pyrazolo[3,4-b]pyridin-4-yl)-phenyl]-3-m-tolyl-urea

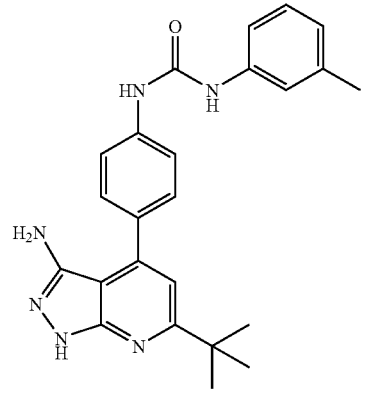

In analogy to the procedure described for Example 1e, reaction of 237 mg 9a with 81 µl hydrazine hydrate in propanol yielded 113 mg product.

$^1$H-NMR (d6-DMSO): δ=1.32 (9H); 2.23 (3H); 4.48 (2H); 6.77 (1H); 6.91 (1H); 7.12 (1H); 7.22 (1H); 7.28 (1H); 7.50 (2H); 7.60 (2H); 8.64 (1H); 8.89 (1H); 12.08 (1H) ppm.

EXAMPLE 10

Preparation of 1-[4-(3-amino-6-tert-butyl-1H-pyrazolo[3,4-b]pyridin-4-yl)-phenyl]-3-(2-nitro-phenyl)-urea

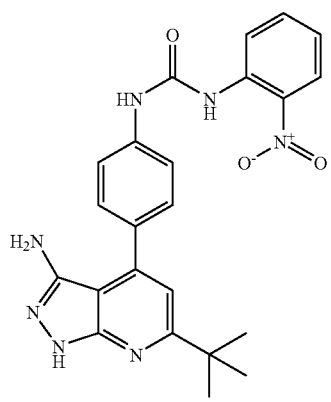

EXAMPLE 10a

Preparation of trifluoromethanesulfonic acid 6-tert-butyl-3-cyano-4-{4-[3-(2-nitro-phenyl)-ureido]-phenyl}-pyridin-2-yl ester

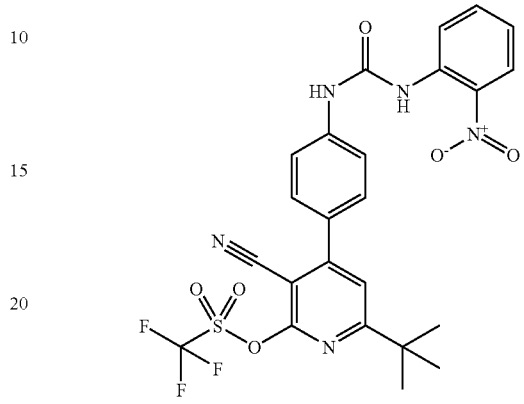

In analogy to the procedure described for Example 1a, reaction of 200 mg 3c and 91 mg 1-isocyanato-2-nitro-benzene yielded 275 mg product.

$^1$H-NMR (d6-DMSO): δ=1.35 (9H); 7.23 (1H); 7.70-7.86 (6H); 8.11 (1H); 8.30 (1H); 9.67 (1H); 10.17 (1H) ppm.

EXAMPLE 10b

Preparation of 1-[4-(3-amino-6-tert-butyl-1H-pyrazolo[3,4-b]pyridin-4-yl)-phenyl]-3-(2-nitro-phenyl)-urea

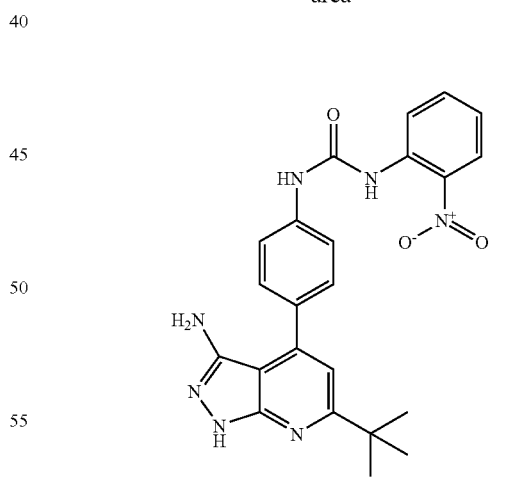

In analogy to the procedure described for Example 1e, reaction of 270 mg 10a with 88 µl hydrazine hydrate in propanol yielded 97 mg product.

$^1$H-NMR (d6-DMSO): δ=1.38 (9H); 4.50 (2H); 6.97 (1H); 7.22 (1H); 7.56 (2H); 7.66-7.78 (3H); 8.11 (1H); 8.31 (1H); 9.65 (1H); 10.06 (1H); 12.10 (1H) ppm.

EXAMPLE 11

Preparation of 1-[4-(3-amino-6-tert-butyl-1H-pyrazolo[3,4-b]pyridin-4-yl)-phenyl]-3-(2,4-difluorophenyl)-urea

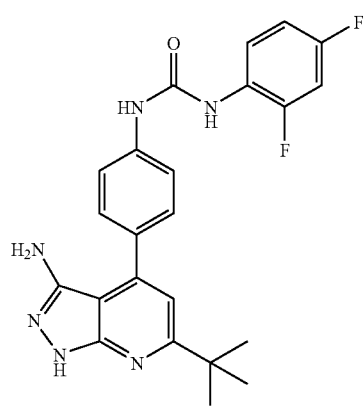

EXAMPLE 11a

Preparation of trifluoro-methanesulfonic acid 6-tert-butyl-3-cyano-4-{4-[3-(2,4-difluoro-phenyl)-ureido]-phenyl}-pyridin-2-yl ester

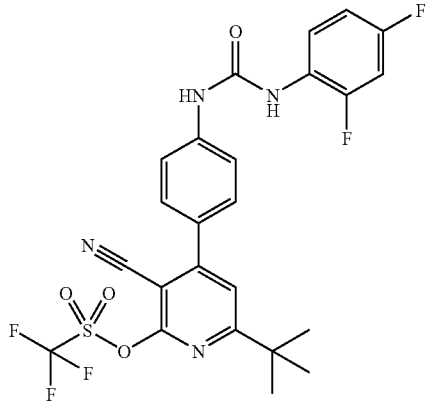

In analogy to the procedure described for Example 1a, reaction of 200 mg 3c and 71 pt 2,4-difluoro-1-isocyanato-benzene yielded 259 mg product.

$^1$H-NMR (d6-DMSO): δ=1.35 (9H); 7.08 (1H); 7.32 (1H); 7.69 (2H); 7.78 (3H); 8.09 (1H); 8.65 (1H); 9.40 (1H) ppm.

EXAMPLE 11b

Preparation of 1-[4-(3-amino-6-tert-butyl-1H-pyrazolo[3,4-b]pyridin-4-yl)-phenyl]-3-(2,4-difluorophenyl)-urea

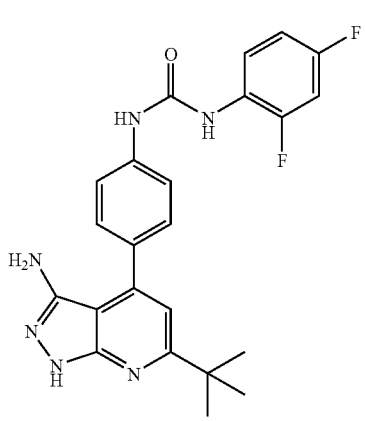

In analogy to the procedure described for Example 1e, reaction of 254 mg 11a with 85 µl hydrazine hydrate in propanol yielded 58 mg product.

$^1$H-NMR (d6-DMSO): δ=1.37 (9H); 4.50 (2H); 6.96 (1H); 7.07 (1H); 7.32 (1H); 7.55 (2H); 7.63 (2H); 8.10 (1H); 8.57 (1H); 9.22 (1H); 12.10 (1H) ppm.

EXAMPLE 12

Preparation of 1-[4-(3-amino-6-tert-butyl-1H-pyrazolo[3,4-b]pyridin-4-yl)-phenyl]-3-(4-fluoro-phenyl)-urea

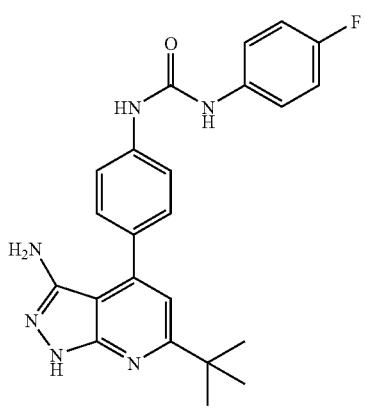

EXAMPLE 12a

Preparation of trifluoromethanesulfonic acid 6-tert-butyl-3-cyano-4-{4-[3-(4-fluorophenyl)-ureido]-phenyl}-pyridin-2-yl ester

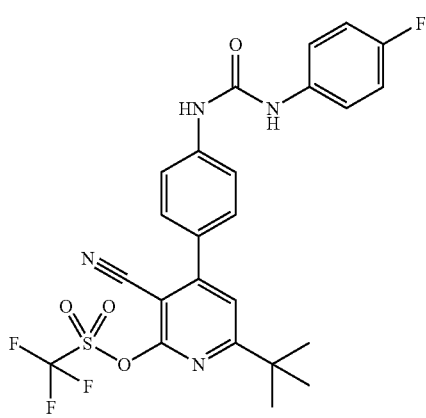

In analogy to the procedure described for Example 1a, reaction of 200 mg 3c and 70μ 4-fluoro-1-isocyanato-benzene yielded 264 mg product.

$^1$H-NMR (d6-DMSO): δ=1.34 (9H); 7.14 (2H); 7.48 (2H); 7.65-7.82 (5H); 8.83 (1H); 9.06 (1H) ppm.

EXAMPLE 12b

Preparation of 1-[4-(3-amino-6-tert-butyl-1H-pyrazolo[3,4-b]pyridin-4-yl)-phenyl]-3-(4-fluoro-phenyl)-urea

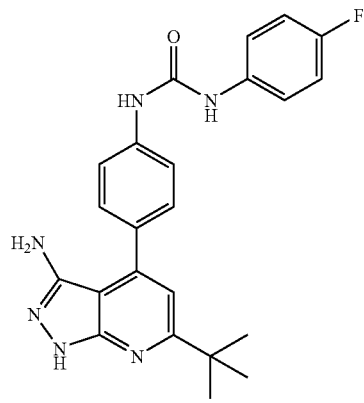

In analogy to the procedure described for Example 1e, reaction of 259 mg 12a with 88 μl hydrazine hydrate in propanol yielded 127 mg product.

$^1$H-NMR (d6-DMSO): δ=1.36 (9H); 4.46 (2H); 6.91 (1H); 7.10 (2H); 7.40-7.53 (4H); 7.60 (2H); 8.74 (1H); 8.86 (1H); 12.08 (1H) ppm.

EXAMPLE 13

Preparation of 1-[4-(3-amino-6-tert-butyl-1H-pyrazolo[3,4-b]pyridin-4-yl)-phenyl]-3-(4-cyano-phenyl)-urea

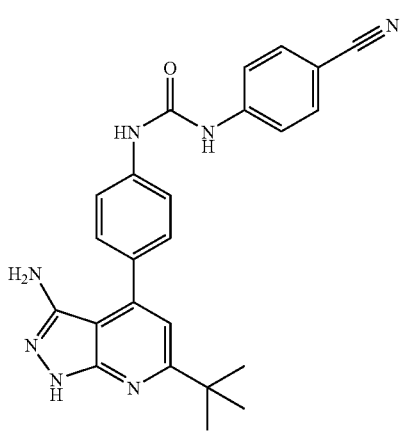

EXAMPLE 13a

Preparation of trifluoromethanesulfonic acid 6-tert-butyl-3-cyano-4-{4-[3-(4-cyano-phenyl)-ureido]-phenyl}-pyridin-2-yl ester

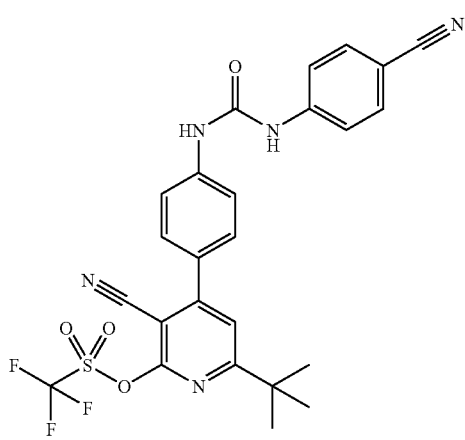

In analogy to the procedure described for Example 1a, reaction of 200 mg 3c and 90 μl 4-isocyanato-benzonitrile yielded 142 mg product.

$^1$H-NMR (d6-DMSO): δ=1.35 (9H); 7.62-7.83 (9H); 9.23 (1H); 9.32 (1H) ppm.

EXAMPLE 13b

Preparation of 1-[4-(3-amino-6-tert-butyl-1H-pyrazolo[3,4-b]pyridin-4-yl)-phenyl]-3-(4-cyano-phenyl)-urea

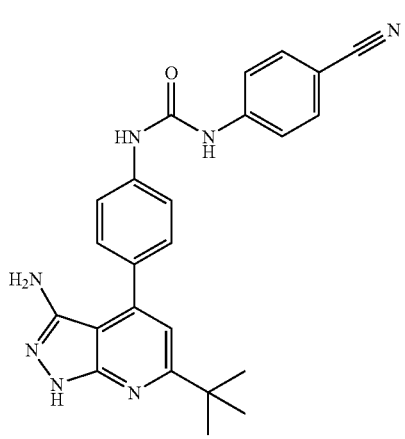

In analogy to the procedure described for Example 1e, reaction of 259 mg 13a with 50 µl hydrazine hydrate in propanol yielded 53 mg product.

$^1$H-NMR (d6-DMSO): δ=1.32 (9H); 4.48 (2H); 6.91 (1H); 7.51 (2H); 7.61 (4H); 7.70 (2H); 9.07 (1H); 9.24 (1H); 12.10 (1H) ppm.

EXAMPLE 14

Preparation of 1-[4-(3-amino-6-cyclopropyl-1H-pyrazolo[3,4-b]pyridin-4-yl)-phenyl]-3-phenyl-urea

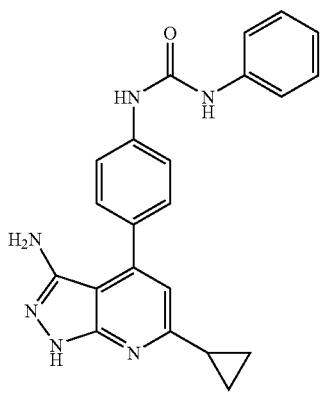

EXAMPLE 14a

Preparation of 6-cyclopropyl-4-(4-nitro-phenyl)-2-oxo-1,2-dihydro-pyridine-3-carbonitrile

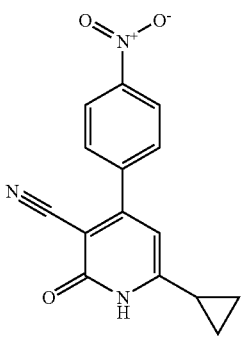

In analogy to the procedure described for Example 3a, reaction of 17.9 g ammonium acetate, 3.5 ml methyl cyanoacetate, 3.8 ml 1-cyclopropyl-ethanone, and 5 g 4-nitrobenzaldehyde yielded 3.23 g product.

$^1$H-NMR (d6-DMSO): δ=1.00-1.25 (4H); 2.00 (1H); 6.10 (1H); 7.88 (2H); 8.37 (2H); 12.82 (1H) ppm.

EXAMPLE 14b

Preparation of trifluoromethanesulfonic acid 3-cyano-6-cyclopropyl-4-(4-nitro-phenyl)-pyridin-2-yl ester

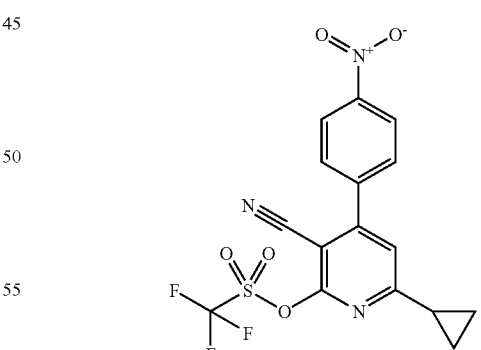

In analogy to the procedure described for Example 3b, reaction of 1.5 g 14a and 2.69 ml trifluoromethanesulfonic acid anhydride in pyridine yielded 1.49 g product.

$^1$H-NMR (CDCl$_3$): δ=1.26 (4H); 2.15 (1H); 7.40 (1H); 7.78 (2H); 8.41 (2H) ppm.

EXAMPLE 14c

Preparation of trifluoromethanesulfonic acid 4-(4-amino-phenyl)-3-cyano-6-cyclopropyl-pyridin-2-yl ester

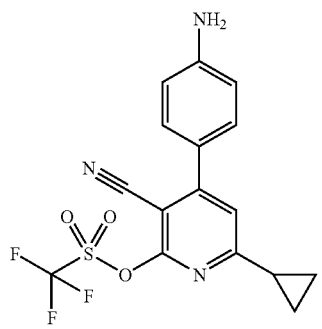

In analogy to the procedure described for Example 3c, reaction of 1.49 g 14b and 4.1 g tin (II) chloride dihydrate in ethanol yielded 1.2 g product.

$^1$H-NMR (d6-DMSO): δ=0.98 (2H); 1.17 (2H); 2.31 (1H); 5.92 (2H); 6.70 (2H); 7.51 (2H); 7.76 (1H) ppm.

EXAMPLE 14d

Preparation of trifluoromethanesulfonic acid 3-cyano-6-cyclopropyl-4-[4-(3-phenyl-ureido)-phenyl]-pyridin-2-yl ester

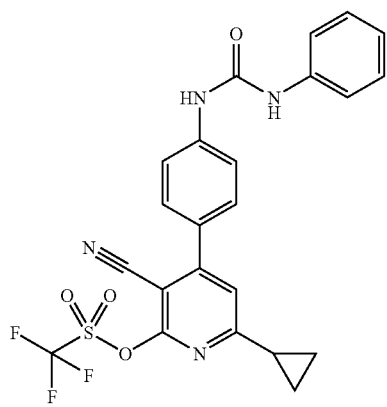

In analogy to the procedure described for Example 3d, reaction of 250 mg 14c and 70 µl isocyanato-benzene yielded 266 mg product.

$^1$H-NMR (d6-DMSO): δ=1.03 (2H); 1.21 (2H); 2.37 (1H); 6.99 (1H); 7.30 (2H); 7.48 (2H); 7.65-7.77 (4H); 7.86 (1H); 8.86 (1H); 9.10 (1H); 1.36 (9H); 7.22-7.35 (4H); 7.45-7.60 (2H); 7.69 (1H); 7.86 (1H); 8.62 (2H) ppm.

EXAMPLE 14e

Preparation of 1-[4-(3-amino-6-cyclopropyl-1H-pyrazolo[3,4-b]pyridin-4-yl)-phenyl]-3-phenyl-urea

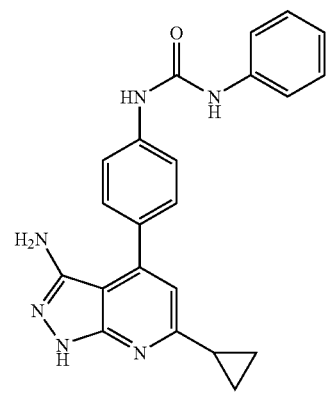

In analogy to the procedure described for Example 3e, reaction of 261 mg 14d with 95 µl hydrazine hydrate in propanol yielded 78 mg product.

$^1$H-NMR (d6-DMSO): δ=1.00 (4H); 2.19 (1H); 4.48 (2H); 6.86 (1H); 6.99 (1H); 7.30 (2H); 7.45-7.59 (4H); 7.63 (2H); 8.78 (1H); 8.91 (1H); 11.97 (1H) ppm.

EXAMPLE 15

Preparation of 1-[4-(3-amino-6-cyclopropyl-1H-pyrazolo[3,4-b]pyridin-4-yl)-phenyl]-3-(2-fluoro-phenyl)-urea

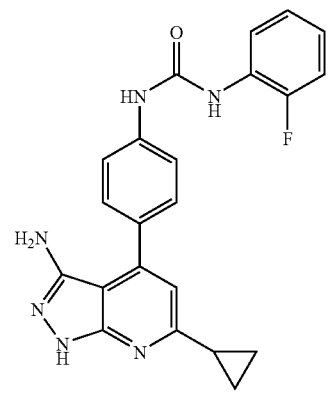

EXAMPLE 15a

Preparation of trifluoromethanesulfonic acid 3-cyano-6-cyclopropyl-4-{4-[3-(2-fluorophenyl)-ureido]-phenyl}-pyridin-2-yl ester

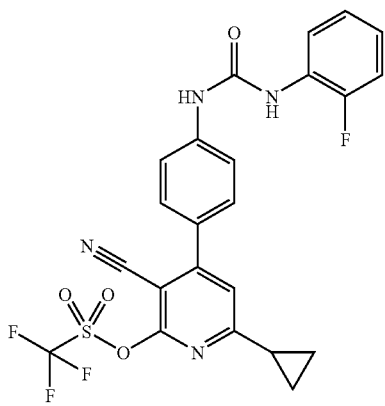

In analogy to the procedure described for Example 3d, reaction of 200 mg 14c and 71 μl 1-fluoro-2-isocyanato-benzene yielded 179 mg product.

$^1$H-NMR (d6-DMSO): δ=0.99 (2H); 1.19 (2H); 2.32 (1H); 7.00 (1H); 7.11 (1H); 7.21 (1H); 7.61-7.74 (4H); 7.83 (1H); 8.10 (1H); 8.69 (1H); 9.42 (1H) ppm.

EXAMPLE 15b

Preparation of 1-[4-(3-amino-6-cyclopropyl-1H-pyrazolo[3,4-b]pyridin-4-yl)-phenyl]-3-(2-fluoro-phenyl)-urea

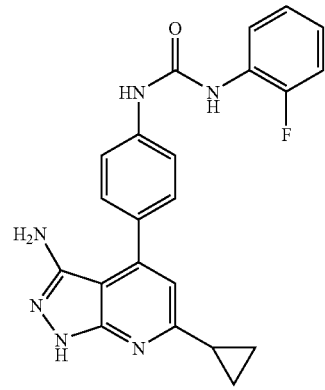

In analogy to the procedure described for Example 3a, reaction of 175 mg 15a with 62 μl hydrazine hydrate in propanol yielded 35 mg product.

$^1$H-NMR (d6-DMSO): δ=0.94 (4H); 2.15 (1H); 4.45 (2H); 6.80 (1H); 6.99 (1H); 7.10 (1H); 7.20 (1H); 7.50 (2H); 7.59 (2H); 8.12 (1H); 8.60 (1H); 9.26 (1H); 11.95 (1H) ppm.

EXAMPLE 16

Preparation of 1-[4-(3-amino-6-isopropyl-1H-pyrazolo[3,4-b]pyridin-4-yl)-phenyl]-3-(3-trifluoromethyl-phenyl)-urea

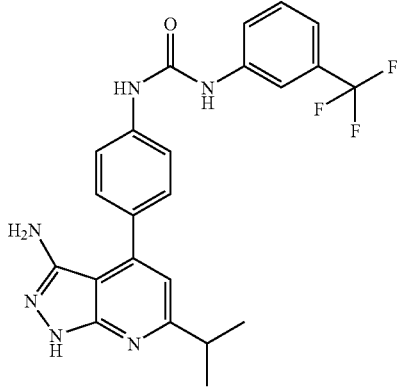

EXAMPLE 16a

Preparation of 6-isopropyl-4-(4-nitro-phenyl)-2-oxo-1,2-dihydro-pyridine-3-carbonitrile

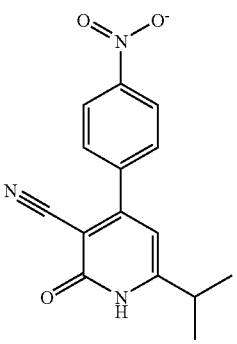

In analogy to the procedure described for Example 3a, reaction of 61.7 g ammonium acetate, 10.67 mL methyl cyanoacetate, 10.71 mL 3-methyl-butan-2-one, and 15.12 g 4-nitrobenzaldehyde yielded 4.24 g product.

$^1$H-NMR (400 MHz; d6-DMSO): δ=1.20 (6H, d); 2.87 (1H, hep); 6.35 (1H, s); 7.87 (2H, d); 8.34 (2H, d); 12.62 (1H, br s) ppm.

EXAMPLE 16b

Preparation of trifluoromethanesulfonic acid 3-cyano-6-isopropyl-4-(4-nitro-phenyl)-pyridin-2-yl ester

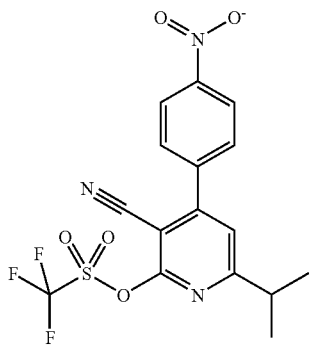

4.19 g 16a was suspended in 110 mL DCM and 1.79 mL pyridine was added followed by the dropwise addition of 3.73 mL trifluoromethanesulphonic acid anhydride. The reaction was stirred for 30 minutes, diluted with water and extracted with DCM. The organic phase was dried through a silicone-treated filter paper and concentrated in vacuo. Purification gave 5.6 g product.

$^1$H-NMR (300 MHz; d6-DMSO): δ=1.24 (6H, d); 3.20 (1H, hep); 7.87 (1H, s); 8.01 (2H, d); 8.42 (2H, d) ppm.

EXAMPLE 16c

Preparation of trifluoromethanesulfonic acid 4-(4-amino-phenyl)-3-cyano-6-isopropyl-pyridin-2-yl ester

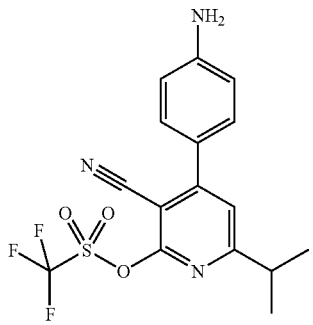

In analogy to the procedure described for Example 3c, reaction of 5.6 g 16b and 15.6 g tin(II) chloride dihydrate in 98 mL ethanol yielded 5.39 g product.

$^1$H-NMR (400 MHz; d6-DMSO): δ=1.20 (6H, d); 3.10 (1H, hep); 5.91 (2H, s); 6.67 (2H, d); 7.50 (2H, d); 7.63 (1H, s) ppm.

EXAMPLE 16d

Preparation of trifluoromethanesulfonic acid 3-cyano-6-isopropyl-4-{4-[3-(3-trifluoromethyl-phenyl)-ureido]-phenyl}-pyridin-2-yl ester

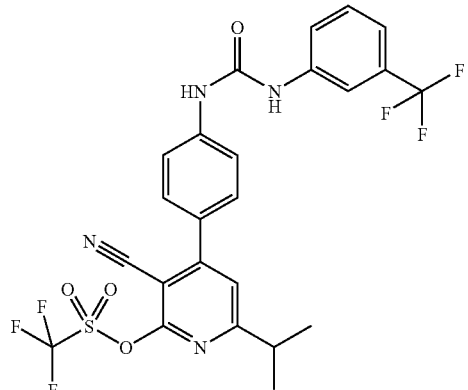

In analogy to the procedure described for Example 3d, reaction of 5.4 g 16c and 3.15 g 1-isocyanato-3-trifluoromethyl-benzene yielded 8.5 g product.

$^1$H-NMR (300 MHz; d6-DMSO): δ=1.23 (6H, d); 3.17 (1H, hep); 7.30 (1H, d); 7.50 (1H, t); 7.58 (1H, d); 7.66-7.73 (4H, m); 7.76 (1H, s); 8.00 (1H, br s); 9.17 (2H, s) ppm.

EXAMPLE 16e

Preparation of 1-[4-(3-amino-6-isopropyl-1H-pyrazolo[3,4-b]pyridin-4-yl)-phenyl]-3-(3-trifluoromethyl-phenyl)-urea

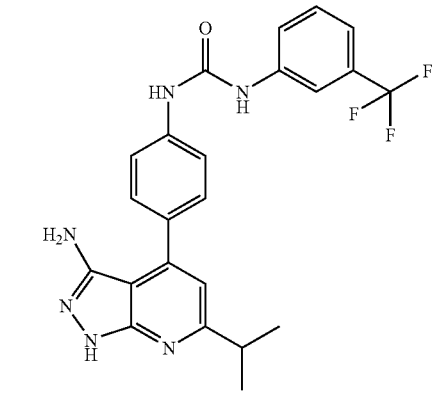

In analogy to the procedure described for Example 3e, reaction of 286 mg 16d with 91 μl hydrazine hydrate in 7.5 mL propanol, followed by purification, gave 70 mg product.

$^1$H-NMR (300 MHz; d6-DMSO): δ=1.25 (6H, d); 3.07 (1H, hep); 4.48 (2H, br s); 6.78 (1H, br s); 7.29 (1H, d), 7.47-7.64 (6H, m); 8.01 (1H, s); 9.00 (1H, s); 9.10 (1H, s), 12.07 (1H, br s) ppm.

EXAMPLE 17

Preparation of N-[4-(3-amino-6-tert-butyl-1H-pyrazolo[3,4-b]pyridin-4-yl)-phenyl]-4-methyl-benzamide

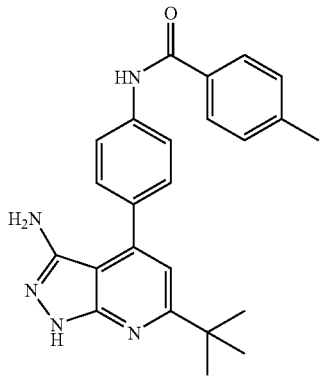

EXAMPLE 17a

Preparation of trifluoromethanesulfonic acid 6-tert-butyl-3-cyano-4-[4-(4-methyl-benzoylamino)-phenyl]-pyridin-2-yl ester

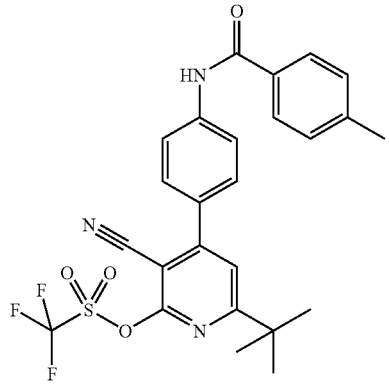

A mixture of 120 mg 3c and 40 μL pyridine in 3.6 mL DCM was reacted with 50 μl 4-methyl-benzoyl chloride. The reaction was stirred for 2 hours before partitioning between water and further DCM. The separated organic phase was dried through a silicone-treated filter paper and concentrated in vacuo. Purification gave 140 mg product.

$^1$H-NMR (300 MHz; d6-DMSO): δ=1.33 (9H, s); 2.37 (3H, s); 7.33 (2H, d); 7.76-7.81 (4H, m); 7.88 (2H, d); 8.00 (2H, d), 10.44 (1H, s) ppm.

EXAMPLE 17b

Preparation of N-[4-(3-amino-6-tert-butyl-1H-pyrazolo[3,4-b]pyridin-4-yl)-phenyl]-4-methyl-benzamide

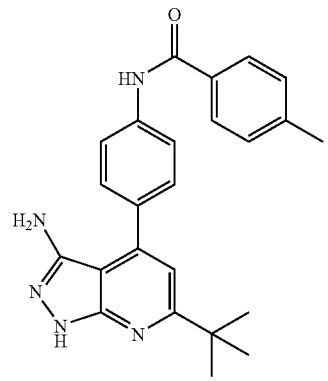

In analogy to the procedure described for Example 1e, reaction of 134 mg 17a with 20 μl hydrazine hydrate in 3.89 mL propanol, followed by purification, yielded 26 mg product.

$^1$H-NMR (400 MHz; d6-DMSO): δ=1.35 (9H, s); 2.37 (3H, s); 4.48 (2H, br s); 6.96 (1H, s); 7.33 (2H, d); 7.56 (2H, d); 7.87 (2H, d); 7.96 (2H, d); 10.34 (1H, s); 12.12 (1H, br s) ppm.

The following examples were prepared by first reacting intermediate 3c with the appropriate isocyanate in analogy to Example 3d, followed by reaction of the resulting crude intermediate with hydrazine hydrate in analogy to Example 3e:

| Example | Structure | Name | 1H-NMR (δ ppm), Mp. (° C.), or $α_D^{20}$ |
|---|---|---|---|
| 18 | 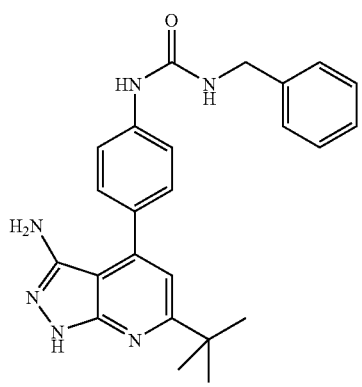 | 1-[4-(3-amino-6-tert butyl-1H-pyrazolo[3,4-b]pyridin-4-yl)-phenyl]-3-benzyl-urea | (d6-DMSO, 300 MHz): 1.34(9H, s), 4.30(2H, d), 4.46(2H, s), 6.68 (1H, t), 6.91(1H, s), 7.19-7.34(5H, m), 7.45 (2H, d), 7.57(2H, d), 8.79(1H, s), 12.07(1H, s) |

-continued

| Example | Structure | Name | 1H-NMR (δ ppm), Mp. (° C.), or $\alpha_D^{20}$ |
| --- | --- | --- | --- |
| 19 | 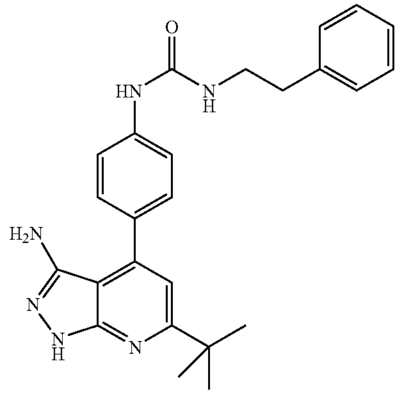 | 1-[4-(3-amino-6-tert-butyl-1H-pyrazolo[3,4-b]pyridin-4-yl)-phenyl]-3-phenethyl-urea | (d6-DMSO, 300 MHz): 1.38(9H, s), 2.78(2H, t), 3.38(2H, signal obscured by residual $H_2O$), 4.51(2H, s), 6.22 (1H, t), 6.93(1H, s), 7.20-7.35(5H, m), 7.48 (2H, d), 7.58(2H, d), 8.75(1H, s), 12.12(1H, s) |
| 20 | 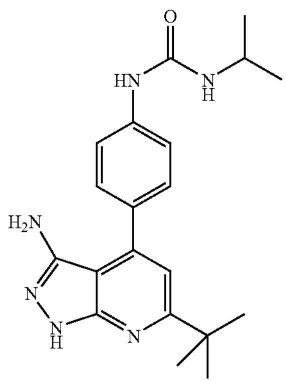 | 1-[4-(3-amino-6-tert-butyl-1H-pyrazolo[3,4-b]pyridin-4-yl)-phenyl]-3-isopropyl-urea | (d6-DMSO, 300 MHz): 1.08(6H, d), 1.34(9H, s), 3.70-3.78(1H, m), 4.45(2H, s), 6.05(1H, d), 6.90(1H, s), 7.42 (2H, d), 7.52(2H, d), 8.50(1H, s), 12.07(1H, s) |
| 21 | 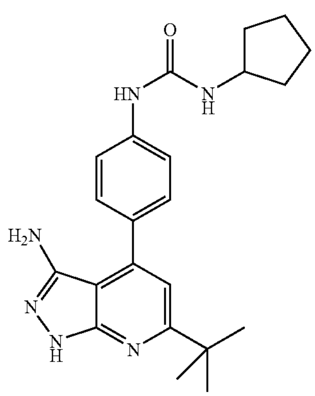 | 1-[4-(3-amino-6-tert-butyl-1H-pyrazolo[3,4-b]pyridin-4-yl)-phenyl]-3-cyclopentyl-urea | (d6-DMSO, 300 MHz): 1.27-1.43(11H, m), 1.46-1.64(4H, m), 1.77-1.87 (2H, m), 3.87-3.98(1H, m), 4.47(2H, s), 6.21 (1H, d), 6.90(1H, s), 7.43(2H, d), 7.52(2H, d), 8.45(1H, s), 12.06 (1H, s) |
| 22 | 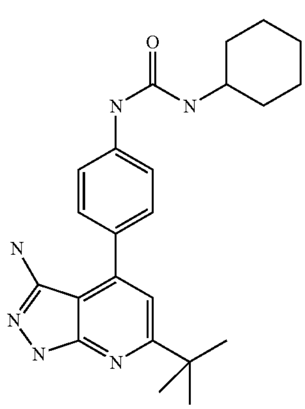 | 1-[4-(3-amino-6-tert-butyl-1H-pyrazolo[3,4-b]pyridin-4-yl)-phenyl]-3-cyclohexyl-urea | (d6-DMSO, 300 MHz): 1.10-1.55(15H, m), 1.60-1.67(2H, m), 1.75-1.83 (2H, m), 3.40-3.50(1H, m), 4.46(2H, s), 6.12 (1H, d), 6.90(1H, s), 7.43(2H, d), 7.52(2H, d), 8.50(1H, s), 12.07 (1H, s) |

-continued

| Example | Structure | Name | 1H-NMR (δ ppm), Mp. (° C.), or $α_D^{20}$ |
|---|---|---|---|
| 23 | 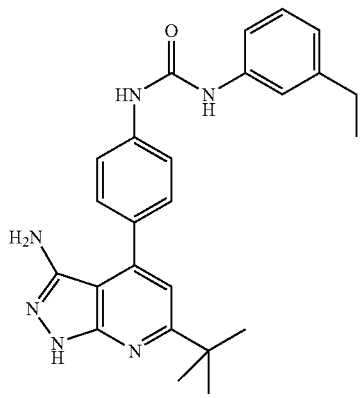 | 1-[4-(3-amino-6-tert-butyl-1H-pyrazolo-[3,4-b]pyridin-4-yl)-phenyl]-3-(3-ethyl-phenyl)-urea | (d6-DMSO, 300 MHz): 1.14(3H, t), 1.43(9H, s), 2.53(2H, q), 4.45 (2H, s), 6.80(1H, d), 6.93(1H, s), 7.16(1H, t), 7.23(1H, dbr), 7.30 (1H, sbr) 7.49(2H, d), 7.60(2H, d), 8.62(1H, s), 8.84(1H, s), 12.06 (1H, s) |
| 24 | 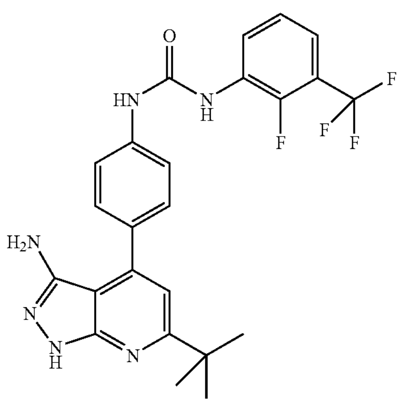 | 1-[4-(3-amino-6-tert-butyl-1H-pyrazolo[3,4-b]pyridin-4-yl)-phenyl]-3-(2-fluoro-3-trifluoromethyl-phenyl)-urea | (d6-DMSO, 300 MHz): 1.35(9H, s), 4.50(2H, s), 6.93 (1H, s), 7.30-7.39(2H, m), 7.53(2H, d), 7.63(2H, d), 8.39-8.49(1H, m), 8.87(1H, s), 9.33(1H, s), 12.10 (1H, s) |
| 25 | 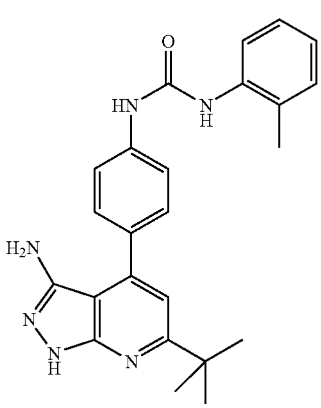 | 1-[4-(3-amino-6-tert-butyl-1H-pyrazolo-[3,4-b]pyridin-4-yl)-phenyl]-3-o-tolyl-urea | (d6-DMSO, 400 MHz): 1.40(9H, s), 2.27(3H, s), 4.52(2H, s), 6.96 (2H, m), 7.17(2H, m), 7.53(2H, d), 7.65(2H, d), 7.86(1H, d), 8.02 (1H, s), 9.28(1H, s), 12.11(1H, s) |

-continued

| Example | Structure | Name | 1H-NMR (δ ppm), Mp. (° C.), or α$_D$$^{20}$ |
|---|---|---|---|
| 26 | 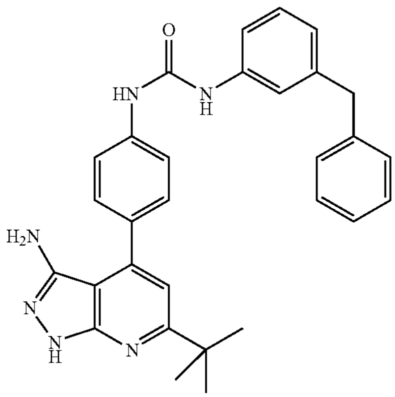 | 1-[4-(3-amino-6-tert-butyl-1H-pyrazolo-[3,4-b]pyridin-4-yl)-phenyl]-3-(3-benzyl-phenyl)-urea | (d6-DMSO, 400 MHz): 1.38(9H, s), 3.91(2H, s), 4.50(2H, s), 6.86 (1H, d), 6.96(1H, s), 7.20(4H, m), 7.30(4H, m), 7.52(2H, d), 7.61 (2H, d), 8.75(1H, s), 8.90(1H, s), 12.11(1H, s) |
| 27 | 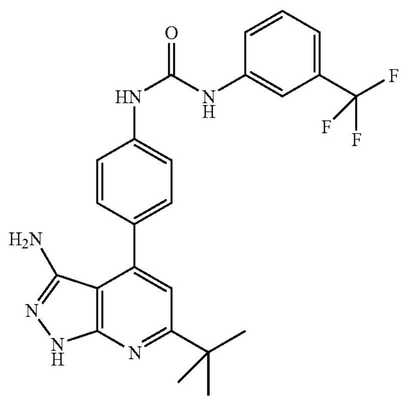 | 1-[4-(3-amino-6-tert-butyl-1H-pyrazolo-[3,4-b]pyridin-4-yl)-phenyl]-3-(3-trifluoro-methyl-phenyl)-urea | (d6-DMSO, 400 MHz): 1.33(9H, s), 4.99(2H, s), 6.92(1H, s), 7.29 (1H, d) 7.50(3H, m), 7.57(1H, d), 7.61(2H, d), 8.00(1H, s), 9.01 (1H, s), 9.11(1H, s), 12.09(1H, s) |
| 28 | 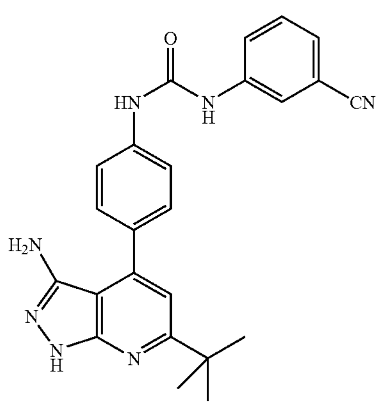 | 1-[4-(3-amino-6-tert-butyl-1H-pyrazolo-[3,4-b]pyridin-4-yl)-phenyl]-3-(3-cyano-phenyl)-urea | (d6-DMSO, 400 MHz): 1.32(9H, s), 4.48(2H, s), 6.91(1H, s), 7.40 (1H, d), 7.47(1H, t), 7.51(2H, d), 7.61(2H, d), 7.96(1H, s), 9.05 (1H, s), 9.08(1H, s), 12.10(1H, s) |

-continued

| Example | Structure | Name | 1H-NMR (δ ppm), Mp. (° C.), or $α_D^{20}$ |
|---|---|---|---|
| 29 | 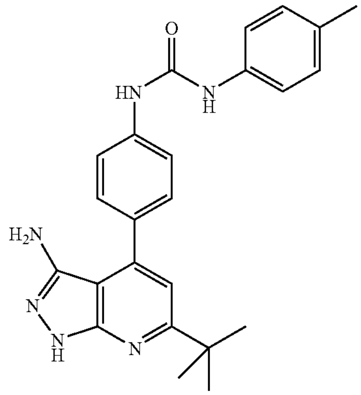 | 1-[4-(3-amino-6-tert-butyl-1H-pyrazolo-[3,4-b]pyridin-4-yl)-phenyl]-3-p-tolyl-urea | (d6-DMSO, 300 MHz): 1.35(9H, s), 2.22(3H, s), 4.47(2H, s), 6.91 (1H, s), 7.05(2H, d), 7.30(2H, d), 7.48(2H, d), 7.60(2H, d), 8.59 (1H, s), 8.81(1H, s), 12.07(1H, s) |
| 30 | 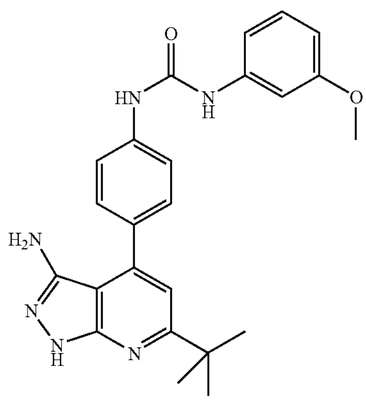 | 1-[4-(3-amino-6-tert-butyl-1H-pyrazolo-[3,4-b]pyridin-4-yl)-phenyl]-3-(3-methoxy-phenyl)-urea | (d6-DMSO, 300 MHz): 1.33(9H, s), 3.70(3H, s), 4.47(2H, s), 6.53 (1H, dd), 6.92(2H, m), 7.15(2H, m), 7.49(2H, d), 7.60(2H, d), 8.74 (1H, s), 8.89(1H, s), 12.08(1H, s) |
| 31 | 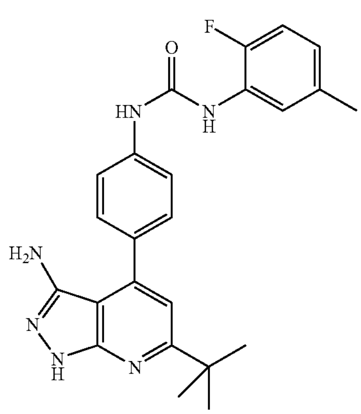 | 1-[4-(3-amino-6-tert-butyl-1 H-pyrazolo[3,4-b]pyridin-4-yl)-phenyl]-3-(2-fluoro-5-methyl-phenyl)-urea | 204 |

| Example | Structure | Name | 1H-NMR (δ ppm), Mp. (° C.), or $\alpha_D^{20}$ |
|---|---|---|---|
| 32 | 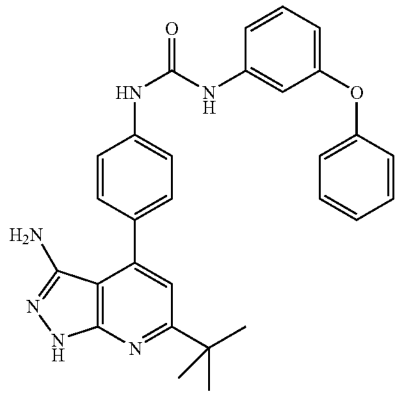 | 1-[4-(3-amino-6-tert-butyl-1H-pyrazolo-[3,4-b]pyridin-4-yl)-phenyl]-3-(3-phenoxy-phenyl)-urea | (d6-DMSO, 400 MHz): 1.35(9H, s), 4.48(2H, s), 6.59(1H, dbr), 6.91 (1H, s), 7.01(2H, s), 7.11(2H, m), 7.25(1H, m), 7.37(2H, m), 7.48 (2H,d), 7.58(2H, d), 8.84(2H, s), 12.07(1H, s) |
| 33 | 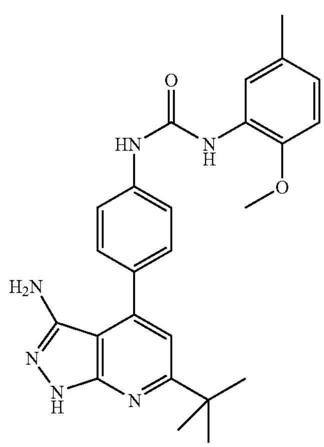 | 1-[4-(3-amino-6-tert-butyl-1H-pyrazolo-[3,4-b]pyridin-4-yl)-phenyl]-3-(2-methoxy-5-methyl-phenyl)-urea | (d6-DMSO, 300 MHz): 1.33(9H, s), 2.20(3H, s), 3.81(3H, s), 4.48 (2H, s), 6.71(1H, dbr), 6.86 81h, d), 6.91(1h, s), 7.50(2H, d), 7.60 (2H, d), 7.98(1H, s), 8.20(1H, s), 9.49(1H, s), 12.08(1H, s) |
| 34 | 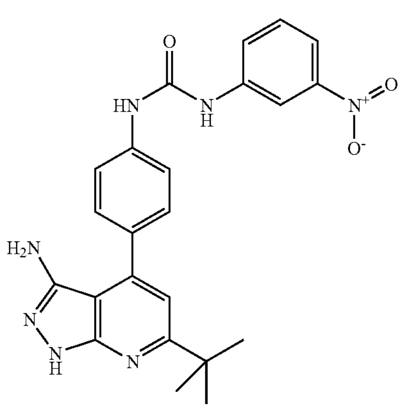 | 1-[4-(3-amino-6-tert-butyl-1H-pyrazolo-[3,4-b]pyridin-4-yl)-phenyl]-3-(3-nitro phenyl)-urea | (d6-DMSO, 400 MHz): 1.36(9H, s), 4.49(2H, s), 6.91(1H, s), 7.53 (3H, m), 7.63(2H, d), 7.70(1H, dbr), 7.80(1H, dbr), 8.54(1H, sbr), 9.07 (1H, s), 9.28(1H, s), 12.09(1H, s) |

| Example | Structure | Name | 1H-NMR (δ ppm), Mp. (° C.), or $α_D^{20}$ |
|---|---|---|---|
| 35 | 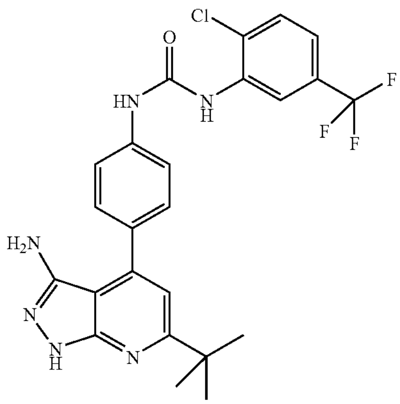 | 1-[4-(3-amino-6-tert-butyl-1H-pyrazolo[3,4-b]pyridin-4-yl)-phenyl]-3-(2-chloro-5-trifluoromethyl-phenyl)-urea | (d6-DMSO, 300 MHz): 133 (9H, s), 4.49(2H, s), 6.93 (1H, s), 7.37(1H, d), 7.53 (2H, d), 7.63(2H, d), 7.70 (1H, d), 8.62(1H, s), 8.67 (1H, s), 9.76(1H, s), 12.10 (1H, s) |
| 36 | 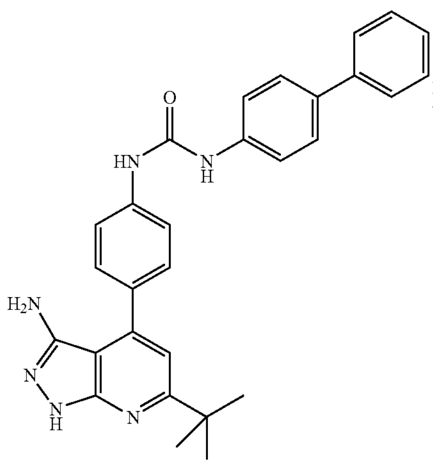 | 1-[4-(3-amino-6-tert-butyl-1H-pyrazolo-[3,4-b[pyridin-4-yl)-phenyl]-3-biphenyl-4-yl-urea | (d6-DMSO, 400 MHz): 1.32(9H, s), 4.49(2H, s), 6.91(1H, s), 7.27(1H, t), 7.40(2H, t), 7.48-ô7.67 (10H, m), 8.83(1H, s), 8.92 (1H, s), 12.08(1H, s) |
| 37 | 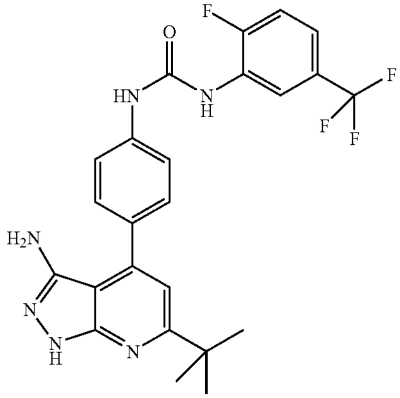 | 1-[4-(3-amino-6-tert-butyl-1H-pyrazolo[3,4-b]pyridin-4-yl)-phenyl]-3-(2-fluoro-5-trifluoromethyl-phenyl)-urea | (d6-DMSO, 300 MHz): 1.35 (9H, s), 4.47(2H, s), 6.93 (1H, s), 7.34-7.40(1H, m), 7.47(1H, d), 7.53(2H, d), 7.63(2H, d), 8.59-8.63 (1H, m), 8.94(1H, s), 9.37 (1H, s), 12.10(1H, s) |

-continued

| Example | Structure | Name | 1H-NMR (δ ppm), Mp. (° C.), or $α_D^{20}$ |
|---|---|---|---|
| 38 | 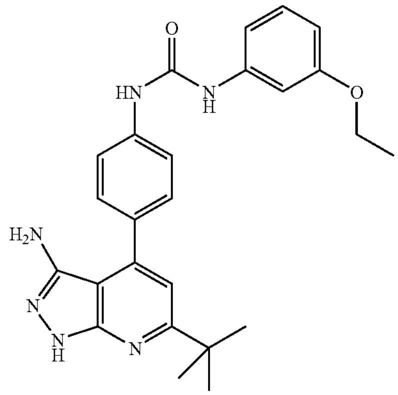 | 1-[4-(3-amino-6-tert-butyl-1H-pyrazolo-[3,4-b]pyridin-4-yl)-phenyl]-3-(3-ethoxy-phenyl)-urea | (d6-DMSO, 300 MHz): 1.29(3H, t), 1.34(9H, s), 3.97(2H, q), 4.47(2H, s), 6.50(1H, sbr), 6.90(1H, dbr), 6.92(1H, s), 7.14 (2H, m), 7.49(2H, d), 7.61 (2H, d), 8.71(1H, s), 8.88 (1H, s), 12.06(1H, s) |
| 39 | 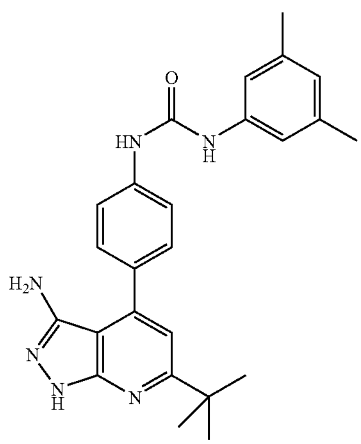 | 1-[4-(3-amino-6-tert-butyl-1H-pyrazolo-[3,4-b]pyridin-4-yl)-phenyl]-3-(3,5-dimethyl-phenyl)-urea | (d6-DMSO, 300 MHz): 1.34(9H, s), 2.20(6H, s), 4.47(2H, s), 6.59 (1H, sbr), 6.91(1H, s), 7.05(2H, sbr), 7.48(2H, d), 7.60(2H, d), 8.52 (1H, s), 8.81(1H, s), 12.06(1H, s) |
| 40 | 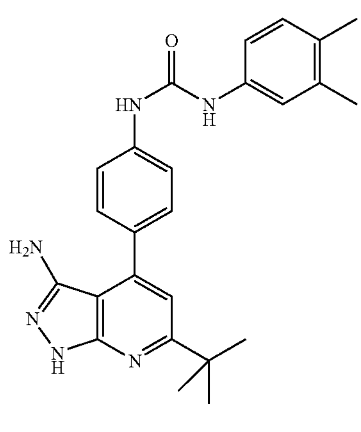 | 1-[4-(3-amino-6-tert-butyl-1H-pyrazolo-[3,4-b]pyridin-4-yl)-phenyl]-3-(3,4-dimethyl-phenyl)-urea | (d6-DMSO, 300 MHz): 1.33(9H, s), 2.11(3H, s), 2.15(3H, s), 4.48 (2H, s), 6.90(1H, s), 7.00(1H, d), 7.14(1H, dbr), 7.22(1H, sbr), 7.48 (2H, d), 7.59(2H, d), 8.50(1H, s), 8.80(1H, s), 12.04(1H, s) |

-continued

| Example | Structure | Name | 1H-NMR (δ ppm), Mp. (° C.), or $α_D^{20}$ |
|---|---|---|---|
| 41 | 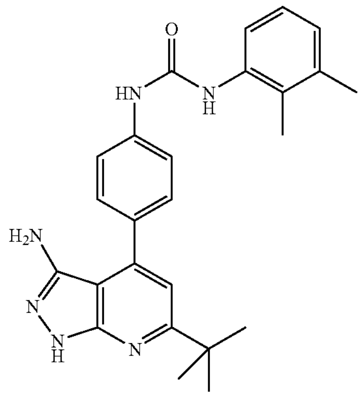 | 1-[4-(3-amino-6-tert-butyl-1H-pyrazolo-[3,4-b]pyridin-4-yl)-phenyl]-3-(2,3-dimethyl-phenyl)-urea | (d6-DMSO, 400 MHz): 1.32(9H, s), 2.11(3H, s), 2.21(3H, s), 4.48 (2H, s), 6.88(1H, d), 6.92(1H, s), 7.01(1H, t), 7.50(3H, m), 7.61 (2H, d), 7.99(1H, s), 9.12(1H, s), 12.07(1H, s) |
| 42 | 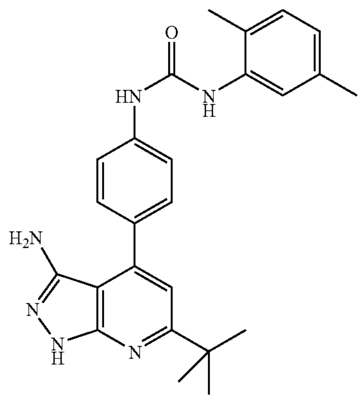 | 1-[4-(3-amino-6-tert-butyl-1H-pyrazolo-[3,4-b]pyridin-4-yl)-phenyl]-3-(2,5-dimethyl-phenyl)-urea | (d6-DMSO, 300 MHz): 1.32(9H, s), 2.17(3H, s), 2.23(3H, s), 4.48 (2H, s), 6.74(1H, dbr), 6.92(1H, s), 7.02(1H, d), 7.49(2H, d), 7.62 (3H, m), 7.88(1H, s), 9.18(1H, s), 12.06(1H, s) |
| 43 | 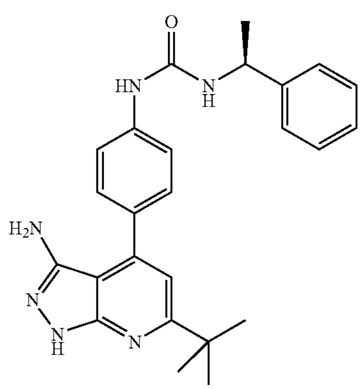 | 1-[4-(3-amino-6-tert-butyl-1H-pyrazolo[3,4-b]pyridin-4-yl)-phenyl]-3-((S)-1-phenyl-ethyl)-urea | $α_D^{20}$ (c = 0.52 in DMF) = −43.4° ±0.4° |
| 44 | 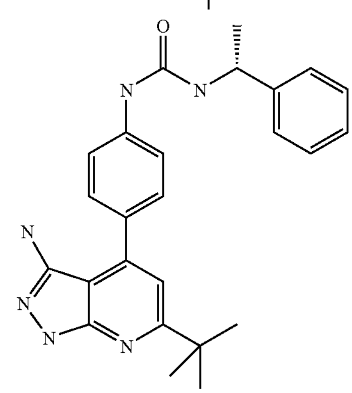 | 1-[4-(3-amino-6-tert-butyl-1H-pyrazolo[3,4-b]pyridin-4-yl)-phenyl]-3-((R)-1-phenyl-ethyl)-urea | $α_D^{20}$ (c = 0.64 in DMF) = +39.9° ±0.4° |

The following example was prepared by first reacting intermediate 14c with 1-isocyanato-3-methyl-benzene in analogy to Example 14d, followed by reaction of the resulting crude intermediate with hydrazine hydrate in analogy to Example 14e:

| Example | Structure | Name | 1H-NMR (δ ppm) |
|---|---|---|---|
| 45 | 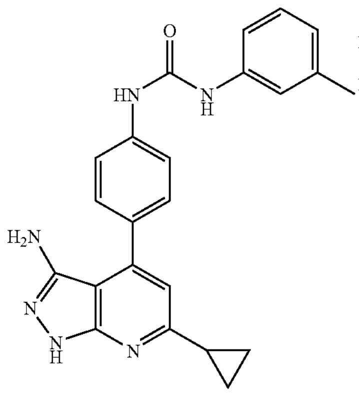 | 1-[4-(3-amino-6-cyclopropyl-1H-pyrazolo-[3,4-b]pyridin-4-yl)-phenyl]-3-m-tolyl-urea | (d6-DMSO, 400 MHz): 0.96(4H, m), 2.15(1H, m), 2.25(3H, s), 4.46 (2H, s), 6.77(1H, dbr), 6.81(1H, s), 7.12(1H, t), 7.20(1H, m), 7.26 (1H, sbr), 7.48(2H, d), 7.60(2H, d), 8.61(1H, s), 8.83(1H, s), 11.96 (1H, s) |

The following examples were prepared by first reacting intermediate 3c with the appropriate acid chloride in analogy to Example 17a, followed by reaction of the resulting crude intermediate with hydrazine hydrate in analogy to Example 17b:

| Example | Structure | Name | 1H-NMR (δ ppm), Mp. (° C.), or ESI (m/z) |
|---|---|---|---|
| 46 | 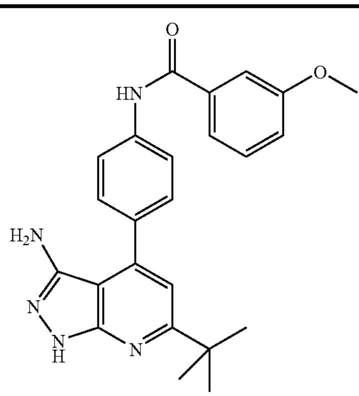 | N-[4-(3-amino-6-tert-butyl-1H-pyrazolo[3,4-b]pyridin-4-yl)-phenyl]-3-methoxy-benzamide | 197 |
| 47 | 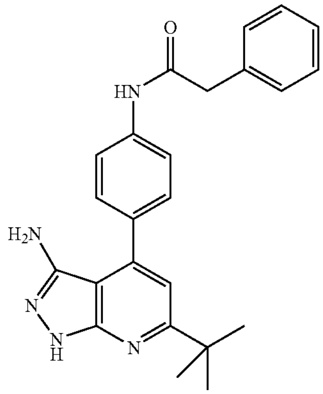 | N-[4-(3-amino-6-tert-butyl-1H-pyrazolo[3,4-b]pyridin-4-yl)-phenyl]-2-phenyl-acetamide | 239 |

| Example | Structure | Name | 1H-NMR (δ ppm), Mp. (° C.), or ESI (m/z) |
|---|---|---|---|
| 48 | 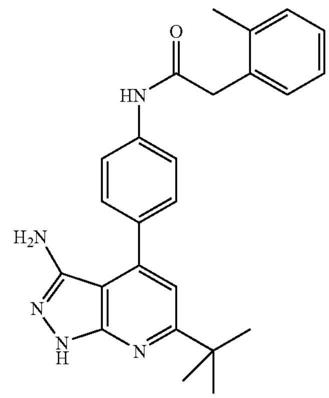 | N-[4-(3-amino-6-tert-butyl-1H-pyrazolo[3,4-b]pyridin-4-yl)-phenyl]-2-o-totyl-acetamide | 257 |
| 49 | 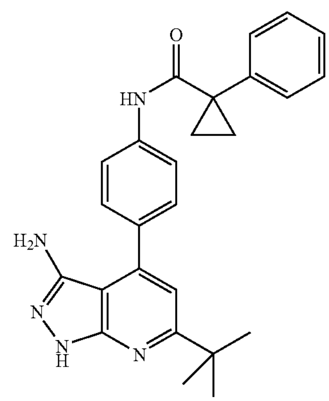 | 1-phenyl-cyclopropanecarboxylic acid [4-(3-amino-6-tert-butyl-1H-pyrazolo[3,4-b]pyridin-4-yl)-phenyl]-amide | 232 |
| 50 | 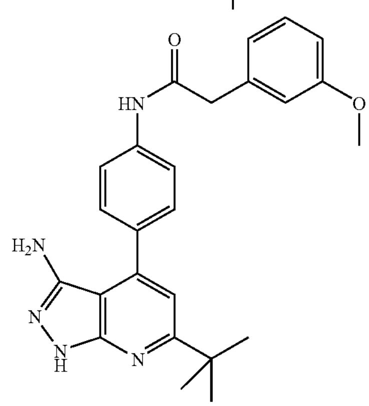 | N-[4-(3-amino-6-tert-butyl-1H-pyrazolo[3,4-b]pyridin-4-yl)-phenyl]-2-(3-methoxy-phenyl)-acetamide | ESI: 430.12 (MH+) m/z |
| 51 | 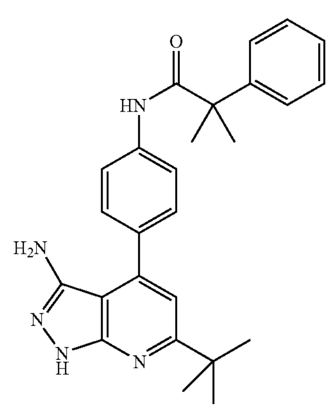 | N-[4-(3-amino-6-tert-butyl-1H-pyrazolo[3,4-b]pyridin-4-yl)-phenyl]-2-phenyl-isobutyramide | (d6-DMSO, 400 MHz): 1.33(9H, s), 1.55(6H, s), 4.45(2H, br s), 6.91 (1H, s), 7.20-7.25 (1H, m), 7.31-7.36 (4H, m), 7.48(2H, d), 7.78(2H, d), 9.28(1H, s), 12.10(1H, s) |

| Example | Structure | Name | 1H-NMR (δ ppm), Mp. (° C.), or ESI (m/z) |
|---|---|---|---|
| 52 | 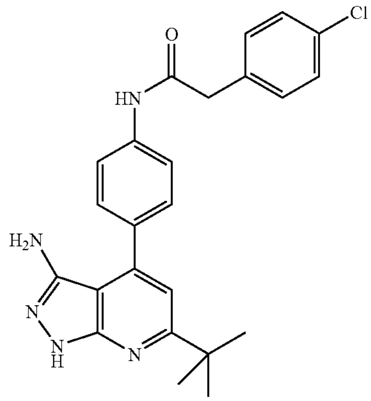 | N-[4-(3-amino-6-tert-butyl-1H-pyrazolo[3,4-b]pyridin-4-yl)-phenyl]-2-(4-chloro-phenyl)-acetamide | 236 |
| 53 | 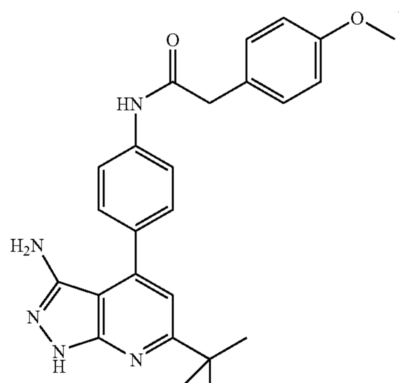 | N-[4-(3-amino-6-tert-butyl-1H-pyrazolo[3,4-b]pyridin-4-yl)-phenyl]-2-(4-methoxy-phenyl)-acetamide | 202 |
| 54 | 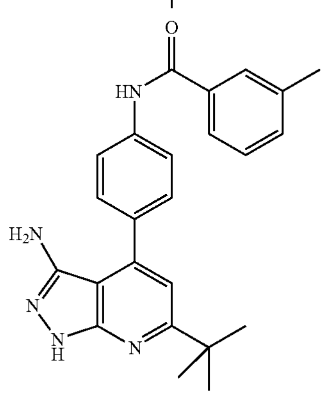 | N-[4-(3-amino-6-tert-butyl-1H-pyrazolo[3,4-b]pyridin-4-yl)-phenyl]-3-methyl-benzamide | (d6-DMSO, 400 MHz): 1.35(9H, s), 2.38(3H, s), 4.49(2H, s), 6.96 (1H, s), 7.38-7.43 (2H, m), 7.57(2H, d), 7.73-7.77(2H, m), 7.95(2H, d), 10.39 (1H, s), 12.12(1H, s) |
| 55 | 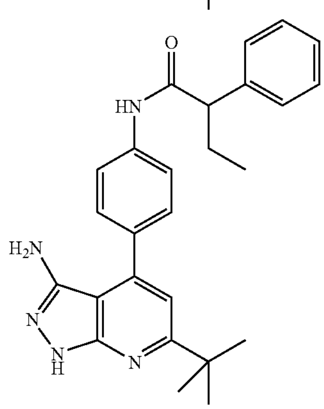 | N-[4-(3-amino-6-tert-butyl-1H-pyrazolo[3,4-b]pyridin-4-yl)-phenyl]-2-phenyl-butyramide | (d6-DMSO, 400 MHz): 0.85(3H, t), 1.33(9H, s), 1.69(1H, mc), 2.05 (1H, mc), 3.57(1H, dd), 4.44(2H, s), 6.89 (1H, s), 7.21(1H, t), 7.30(2H, t), 7.38(2H, d), 7.49(2H, d), 7.75 (2H, d), 10.27(1H, s), 12.09(1H, s) |

The following examples were prepared by first reacting intermediate 3c with the appropriate sulfonyl chloride in analogy to Example 2a, followed by reaction of the resulting crude intermediate with hydrazine hydrate in analogy to Example 2e:

| Example | Structure | Name | 1H-NMR (δ ppm) |
|---|---|---|---|
| 56 | 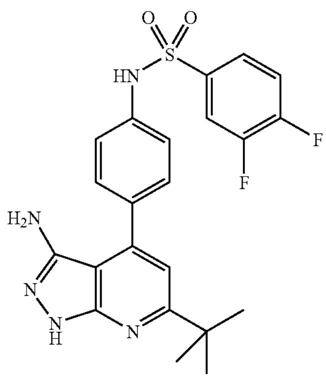 | N-[4-(3-amino-6-tert-butyl-1H-pyrazolo-[3,4-b]pyridin-4-yl)-phenyl]-3,4-difluoro-benzenesulfonamide | (d6-DMSO, 300 MHz): 1.31(9H, s), 4.35(2H, s), 6.87(1H, s), 7.22 (2H, d), 7.48(2H, d), 7.65(2H, m), 7.86(1H, tbr), 10.65(1H, s), 12.09(1H, s) |
| 57 | 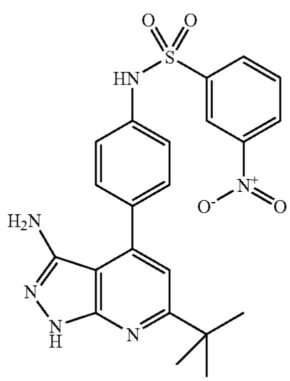 | N-[4-(3-amino-6-tert-butyl-1H-pyrazolo-[3,4-b]pyridin-4-yl)-phenyl]-3-nitro-benzenesulfonamide | (d6-DMSO, 400 MHz): 1.30(9H, s), 4.35(2H, s), 6.84(1H, s), 7.24 (2H, d), 7.48(2H, d), 7.86(1H, t), 8.18(1H, dbr), 8.42(1H, dbr), 8.52(1H, s), 10.80(1H, s), 12.09(1H, s) |
| 58 | 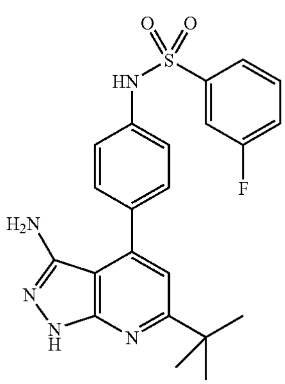 | N-[4-(3-amino-6-tert-butyl-1H-pyrazolo-[3,4-b]pyridin-4-yl)-phenyl]-3-fluoro-benzenesulfonamide | (d6-DMSO, 300 MHz): 1.30(9H, s), 4.33(2H, s), 6.87(1H, s), 7.23 (2H, d), 7.48(3H, m), 7.53(3H, m), 10.75 (1H, s), 12.08(1H, s) |

-continued

| Example | Structure | Name | 1H-NMR (δ ppm) |
|---|---|---|---|
| 59 | 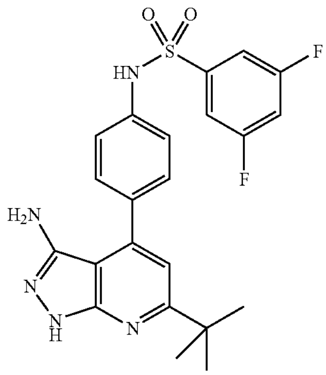 | N-[4-(3-amino-6-tert-butyl-1H-pyrazolo-[3,4-b]pyridin-4-yl)-phenyl]-3,5-difluoro-benzenesulfonamide | (d6-DMSO, 300 MHz): 1.32(9H, s), 4.37(2H, s), 6.88(1H, s), 7.24 (2H, d), 7.50(4H, m), 7.60(1H, m), 10.80 (1H, s), 12.10(1H, s) |
| 60 | 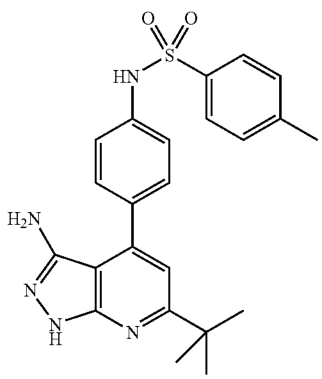 | N-[4-(3-amino-6-tert-butyl-1H-pyrazolo-[3,4-b]pyridin-4-yl)-phenyl]-4-methyl-benzenesulfonamide | (d6-DMSO, 300 MHz): 1.29(9H, s), 2.30(3H, s), 4.34(2H, s), 6.85 (1H, s), 7.20(2H, d), 7.33(2H, d), 7.41(2H, d), 7.68(2H, d), 10.75 (1H, s), 12.07(1H, s) |
| 61 | 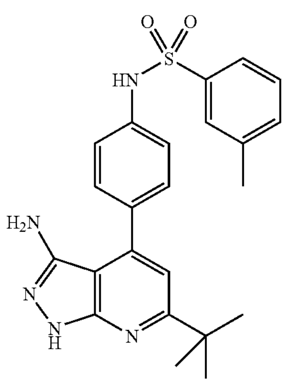 | N-[4-(3-amino-6-tert-butyl-1H-pyrazolo-[3,4-b]pyridin-4-yl)-phenyl]-3-methyl-benzenesulfonamide | (d6-DMSO, 600 MHz): 1.36(9H, s), 2.36(3H, s), 4.40(2H, s), 6.89 (1H, s), 7.27(2H, d), 7.50(4H, m), 7.67(2H, d), 10.80(1H, s), 12.13 (1H, s) |
| 62 | 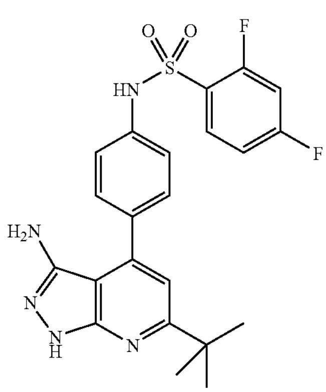 | N-[4-(3-amino-6-tert-butyl-1H-pyrazolo-[3,4-b]pyridin-4-yl)-phenyl]-2,4-difluoro-benzenesulfonamide | (d6-DMSO, 300 MHz): 1.31(9H, s), 4.36(2H, s), 6.35(1H, s), 7.20 (3H, m), 7.45(2H, m), 7.52(1H, dbr), 7.94 (1H, qbr), 10.91(1H, s), 12.09(1H, s) |

The following examples were prepared by first reacting intermediate 14c with the appropriate sulfonyl chloride in analogy to Example 2a, followed by reaction of the resulting crude intermediate with hydrazine hydrate in analogy to Example 2e:

| Example | Structure | Name | 1H-NMR (δ ppm) |
|---|---|---|---|
| 63 | 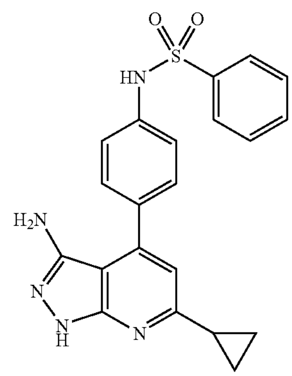 | N-[4-(3-amino-6-cyclopropyl-1H-pyrazolo-[3,4-b]pyridin-4-yl)-phenyl]-benzenesulfonamide | (d6-DMSO, 400 MHz): 0.90(4H, m), 2.10(1H, m), 4.35(2H, s), 6.74 (1H, s), 7.20(2H, d), 7.41(2H, d), 7.50-7.65 (3H, m), 7.78(2H, d), 10.56(1H, s), 11.98 (1H, s) |
| 64 | 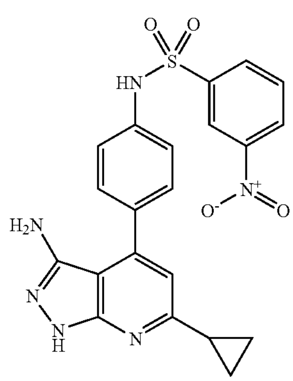 | N-[4-(3-amino-6-cyclopropyl-1H-pyrazolo-[3,4-b]pyridin-4-yl)-phenyl]-3-nitro-benzenesulfonamide | (d6-DMSO, 300 MHz): 0.91(4H, m), 2.12(1H, m), 4.30(2H, s), 6.75 (1H, s), 7.22(2H, d), 7.46(2H, d), 7.73(1H, t), 8.16(1H, dbr), 8.42 (1H, dbr), 8.51(1H, m), 10.73(1H, s), 11.96(1H, s) |
| 65 | 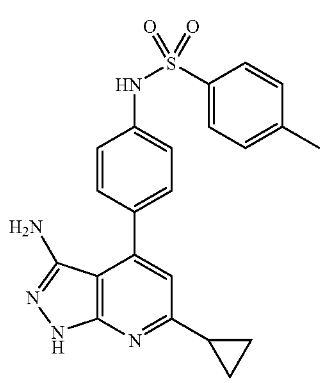 | N-[4-(3-amino-6-cyclopropyl-1H-pyrazolo-[3,4-b]pyridin-4-yl)-phenyl]-4-methyl-benzenesulfonamide | (d6-DMSO, 300 MHz): 0.92(4H, m), 2.12(1H, m), 2.30(3H, s), 4.32 (2H, s), 6.73(1H, s), 7.19(2H, d), 7.32(2H, d), 7.41(2, d), 7.67 (2H, d), 10.70(1H, s), 11.92(1H, s) |

-continued

| Example | Structure | Name | 1H-NMR (δ ppm) |
|---|---|---|---|
| 66 | 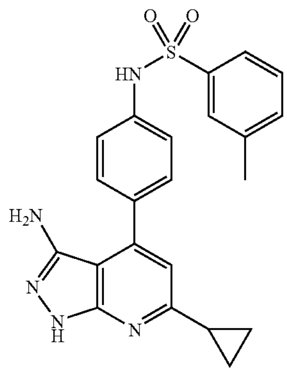 | N-[4-(3-amino-6-cyclo-propyl-1H-pyrazolo-[3,4-b]pyridin-4-yl)-phenyl]-3-methyl-benzenesulfonamide | (d6-DMSO, 400 MHz): 0.93(4H, m), 2.10(1H, m), 2.30(3H, s), 4.32 (2H, s), 6.76(1H, s), 7.20(2H, d), 7.40-7.50 (5H, m), 7.58(1H, m), 10.74(1H, s), 11.97 (1H, s) |

Methods of testing for a particular pharmacological property are well known to persons skilled in the art. For example, modification of the following tyrosine kinase testing protocols may be achieved by using the appropriate tyrosine kinase, the appropriate substrate (such as a biotinylated peptide or biotinylated polymer), and by using the appropriate assay buffer conditions. The example testing experiments described herein serve to illustrate the present invention and the invention is not limited to the examples given.

Biological Experiment 1: ELISA-Assay

To prove the effectiveness of the compounds according to the present invention the following ELISA-method was established and used.

Herein CHO cell-cultures, which are stably transfected by known techniques with Tie2 using DHFR deficiency as selection marker, are stimulated by angiopoietin-2. The specific autophosphorylation of Tie2 receptors is quantified with a sandwich-ELISA using anti-Tie2 antibodies for catch and anti-phosphotyrosine antibodies coupled to HRP as detection.

Materials:

96 well tissue culture plate, sterile, Greiner 96 well FluoroNunc plate MaxiSorp Surface C, Nunc 96 well plate polypropylene for compound dilution in DMSO CHO Tie2/DHFR (transfected cells)

PBS−; PBS++, DMSO

MEM alpha Medium with Glutamax-I without Ribonucleosides and Deoxyribonucleosides (Gibco #32561-029) with 10% FCS after dialysis and 1% PenStrep Lysis buffer: 1 Tablet "Complete" protease inhibitor
  1 cap Vanadate (1 mL>40 mg/mL; working solution 2 mM) ad 50 mL with Duschl buffer pH 7.6

Anti-TIE-II antibody 1:425 in Coating Buffer pH 9.6

Stock solution: 1.275 mg/ml>working.: 3 μg/mL

PBST: 2 bottles PBS(10×)+10 ml Tween, fill up with deionised water

RotiBlock 1:10 in deionised water

Anti-Phosphotyrosine HRP-Conjugated 1:10000 in 3% TopBlock
  3% TopBlock in PBST BM Chemiluminescence ELISA Substrate (POD) solution B 1:100 solution A SF9 cell culture medium Ang2-Fc in SF9 cell culture medium Cell Experiment:

Dispense $5 \times 10^4$ cells/well/98 μl in 96 well tissue culture plate

Incubate at 37° C./5% $CO_2$

After 24 h add compounds according to desired concentrations

Add also to control and stimulated values without compounds 2 μl DMSO

And mix for a few min at room temperature

Add 100 μ Ang2-Fc to all wells except control, which receives insect medium

Incubate 20 min at 37° C.

Wash 3× with PBS++

Add 100 μl Lysis buffer/well and shake a couple of min at room temperature

Store lysates at 20° C. before utilizing for the ELISA

Performance of Sandwich-ELISA

Coat 96 well FluoroNunc Plate MaxiSorp Surface C with anti-Tie2 Mab

1:425 in Coating buffer pH 9.6; 100 μL/well overnight at 4° C.

Wash 2× with PBST

Block plates with 250 μL/well RotiBlock 1:10 in deionised water

Incubate for 2 h at room temperature or overnight at 4° C. shaking

Wash 2× in PBST

Add thawed lysates to wells and incubate overnight shaking at 4° C.

Wash 2× with PBST

Add 100 μL/well anti-Phosphotyrosine HRP-Conjugated 1:10000 in 3%

TopBlock (3% TopBlock in PBST) and incubate overnight under shaking

Wash 6× with PBST

Add 100 μL/well BM Chemiluminescence ELISA Substrate (POD solutions 1 and 2 (1:100)

Determine luminescence with the LumiCount.

Biological Experiment 2: Tie-2-Kinase HTRF-Assay

To prove the effectiveness of the compounds according to the present invention a Tie-2-Kinase HTRF-Assay was established and used.

Tie-2 phosphorylates tyrosine residues of the artificial substrate polyGAT (biotinylated polyGluAlaTyr). Detection of phosphorylated product is achieved specifically by a trimeric detection complex consisting of the phosphorylated substrate, streptavidin-XLent (SA-XLent) which binds to biotin, and Europium Cryptate-labeled anti-phosphotyrosine antibody PT66 which binds to phosphorylated tyrosine. Excitation of Europium fluorescence with 337 nm light results in emission of long-lived light with 620 nm. In case a trimeric detection complex has formed, part of the energy will be transferred to the SA-XLent fluorophore that itself then emits long-lived light of 665 nm (FRET: fluorescence resonance energy transfer). Unphosphorylated substrate does not give rise to light emission at 665 nm, because no FRET-competent trimeric detection complex can be formed. Measurement is performed in a Packard Discovery or BMG Rubystar instrument. A-counts (emission at 665 nm) will be divided by B-counts (emission at 620 nm) and multiplicated with a factor of 10000. The resulting numbers are called the "well ratio" of the sample.

Materials:

Enzyme: Tie-2-Kinase, in house, aliquots (12×10 mL) stored at −80° C.

Substrate: PolyGAT labeled with Biotin (1000 μg/mL); CIS Bio; # 61GATBLB; aliquots stored at −20° C.

ATP: Amersham Pharmacia Biotech Inc. # 27-2056-01; 100 mM; stored at −20° C.

Antibody: PT66-Eu Cryptate; CIS Bio; # 61T66KLB; 30 μg/mL; aliquots stored at −20° C.

SA-XLent; CIS Bio; # 611SAXLB; 1000 μg/mL; aliquots stored at −80° C.

Microplates: 384 Well black, SV, Greiner, # 784076

Solutions:

Assay Buffer:

50 mM HEPES (pH 7.0), 25 mM $MgCl_2$, 5 mM $MnCl_2$, 1 mM DTT, 0.5 mM $Na_3VO_4$, 0.01% (v/v) NP40, 1× Complete EDTA free Enzyme Working Solution:

Tie-2 stock solution is diluted 1:250 in assay buffer

Substrate Working Solution:

PolyGAT (1000 μg/mL; 36.23 μM) is diluted 1:90.6 to 400 nM or 77.3 ng/well, ATP (100 mM) is diluted 1:5000 to 20.0 μM. Both dilutions in assay buffer. Final assay concentrations: poly-GAT: 200 nM or 5.25 μg/mL, ATP: 10 μM (1×Km each).

Detection solution: 50 mM HEPES (pH 7.0), BSA 0.2%, 0.6 M KF, 200 mM EDTA, PT66-Europium Cryptate 2.5 ng/well, SA-XLent C is Bio 90 ng/well.

Assay Steps

All steps at 20° C.

1. 0.75 μL of compound solution in 30% (v/v) DMSO 2. add 7 μL of substrate working solution 3. add 7 μL of enzyme working solution 4. incubate 75 min (reaction volume: 14.75 μL)

5. add 8 μL of detection solution 6. incubate 180 min or over night at 4° C. (total volume: 22.75 μL)

7. measure HTRF in Packard Discovery or BMG Rubystar instrument (delay 50 μs, integrated time 400 μs)

Final Concentrations (in 14.75 μL Reaction Volume):

Enzyme: unknown polyGAT (1×Km): 200 nM (77.3 ng)

ATP (1×Km): 10 μM

DMSO: 1.5% (v/v)

Buffer conditions: 50 mM HEPES (pH 7.0), 25 mM $MgCl_2$, 5 mM $MnCl_2$, 1 mM DTT, 0.5 mM NaVO4, 0.01% (v/v) NP40, 1× Complete Controls:

$C_0$: uninhibited reaction (DMSO only)

$C_i$: inhibited reaction with 20 μM Staurosporine

Biological Experiment 3: Tie-2 Kinase Assay without Preactivation of Kinase

A recombinant fusion protein of GST and the intracellular domains of Tie-2, expressed in insect cells (Hi-5) and purified by Glutathion-Sepharose affinity chromatography was used as kinase. Alternatively, commercially available GST-Tie2-fusion protein (Upstate Biotechnology, Dundee, Scotland) can be used. As substrate for the kinase reaction the biotinylated peptide biotin-Ahx-EPKDDAYPLYSDFG (C-terminus in amide form) was used which can be purchased e.g. from the company Biosynthan GmbH (Berlin-Buch, Germany). Tie-2 (3.5 ng/measurement point) was incubated for 60 min at 22° C. in the presence of 10 μM adenosine-tri-phosphate (ATP) and 1 μM substrate peptide (biotin-Ahx-EPKDDAYPLYS-DFG-$NH_2$) with different concentrations of test compounds (0 μM and concentrations in the range 0.001-20 μM) in 5 μl assay buffer [50 mM Hepes/NaOH pH 7, 10 mM $MgCl_2$, 0.5 mM $MnCl_2$, 1.0 mM dithiothreitol, 0.01% NP40, protease inhibitor mixture ("Complete w/o EDTA" from Roche, 1 tablet per 2.5 ml), 1% (v/v) dimethylsulfoxide]. To stabilize the enzyme, bovine serum albumin (0.1%, w/v) can be added. The reaction was stopped by the addition of 5 μl of an aqueous buffer (25 mM Hepes/NaOH pH 7.5, 0.28% (w/v) bovine serum albumin) containing EDTA (90 mM) and the HTRF (Homogeneous Time Resolved Fluorescence) detection reagents streptavidine-XLent (0.2 μM, from C is Biointernational, Marcoule, France) and PT66-Eu-Chelate (0.3 ng/μl; a europium-chelate labelled anti-phospho-tyrosine antibody from Perkin Elmer).

The resulting mixture was incubated 1 h at 22° C. to allow the binding of the biotinylated phosphorylated peptide to the streptavidine-XLent and the PT66-Eu-Chelate. Subsequently the amount of phosphorylated substrate peptide was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate peptide. The data were normalised (enzyme reaction without inhibitor=0% inhibition, all other assay components but no enzyme=100% inhibition) and $IC_{50}$ values were calculated by a 4 parameter fit using an inhouse software.

Biological Experiment 4: Tie-2 Kinase Assay with Preactivation of Kinase

A recombinant fusion protein of GST and the intracellular domains of Tie-2, expressed in insect cells (Hi-5) and purified by Glutathion-Sepharose affinity chromatography was used as kinase. As substrate for the kinase reaction the biotinylated peptide biotin-Ahx-EPKDDAYPLYSDFG (C-terminus in amid form) was used which can be purchased e.g. from the company Biosynthan GmbH (Berlin-Buch, Germany).

For activation, Tie-2 was incubated at a conc. 12.5 ng/pt of for 20 min at 22° C. in the presence of 250 µM adenosine-tri-phosphate (ATP) in assay buffer [50 mM Hepes/NaOH pH 7, 10 mM $MgCl_2$, 0.5 mM $MnCl_2$, 1.0 mM dithiothreitol, 0.01% NP40, protease inhibitor mixture ("Complete w/o EDTA" from Roche, 1 tablet per 2.5 ml)].

For the subsequent kinase reaction, the preactivated Tie-2 (0.5 ng/measurement point) was incubated for 20 min at 22° C. in the presence of 10 µM adenosine-tri-phosphate (ATP) and 1 µM substrate peptide (biotin-Ahx-EPKDDAYPLYS-DFG-$NH_2$) with different concentrations of test compounds (0 µM and concentrations in the range 0.001-20 µM) in 5 µl assay buffer [50 mM Hepes/NaOH pH 7, 10 mM $MgCl_2$, 0.5 mM $MnCl_2$, 0.1 mM sodium ortho-vanadate, 1.0 mM dithiothreitol, 0.01% NP40, protease inhibitor mixture ("Complete w/o EDTA" from Roche, 1 tablet per 2.5 ml), 1% (v/v) dimethylsulfoxide]. The reaction was stopped by the addition of 5 µl of an aqueous buffer (25 mM Hepes/NaOH pH 7.5, 0.28% (w/v) bovine serum albumin) containing EDTA (90 mM) and the HTRF (Homogeneous Time Resolved Fluorescence) detection reagents streptavidine-XLent (0.2 µM, from Cis Biointernational, Marcoule, France) and PT66-Eu-Chelate (0.3 ng/µl; a europium-chelate labelled anti-phosphotyrosine antibody from Perkin Elmer). The resulting mixture was incubated 1 h at 22° C. to allow the binding of the biotinylated phosphorylated peptide to the streptavidine-XLent and the PT66-Eu-Chelate. Subsequently the amount of phosphorylated substrate peptide was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate peptide. The data were normalised (enzyme reaction without inhibitor=0% inhibition, all other assay components but no enzyme=100% inhibition) and $IC_{50}$ values were calculated by a 4 parameter fit using an inhouse software.

Biological Experiment 5: VEGFR-2 Kinase Assay

To prove the effectiveness of the compounds according to the present invention the following VEGFR-2 kinase assay was established and used.

Recombinant VEGFR-2 protein was expressed in *E. coli* and purified. As kinase substrate, a biotinylated peptide with the amino acid sequence biotin-DFGLARDMYD-KEYYSVG was used, which was obtained from Biosynthan.

VEGFR-2 [Test volume 5 µL] was incubated for 45 min at 22° C. in the presence of different concentrations of test substances (0 µM, including 10 datapoints within the range 0.001-20 µM in duplicate) in assay buffer [50 mM HEPES pH7.0, 25.0 mM $MgCl_2$, 5.0 mM $MnCl_2$, 0.1 mM Na ortho-Vanadate, 1.0 mM Dithiothreitol, 0.001% NP40, 10 µM ATP, 1.2 µM peptide substrate, 1.0% DMSO]. The reaction was stopped by addition of 5 µL of an EDTA/detection-solution [50 mM HEPES pH7.5, 125 mM EDTA, 0.2% BSA, 0.1 µM Streptavidin-XLent (obtained from CisBio), 1 nM PT66-Eu (obtained from PerkinElmer)]. The measurement of the fluorescence emission at 620 nm and 665 nm through excitation with light of wavelength 350 nm was accomplished in a Rubystar HTRF-measurement instrument obtained from BMG Labsystems.

The data (ratio of emission at 665 nm to emission at 620 nm multiplied by 10000) was normalised to 0% inhibition (enzyme reaction without inhibitor) and 100% inhibition (all assay components without enzyme). The determination of the IC50 values was accomplished with a 4-parameter fit using in-house software.

Selected results are presented in the following Table:

TABLE

| Example | Inhibition of Tie-2 kinase (Biological Experiment 3) | Activity in Tie-2 ELISA | Inhibition of VEGFR-2 kinase |
|---|---|---|---|
| 1 | ++++ | +++ | +++ |
| 2 | +++ | +++ | |
| 3 | +++ | ++++ | |
| 9 | ++++ | ++++ | +++ |
| 12 | +++ | ++++ | |
| 14 | +++ | ++++ | ++++ |
| 15 | ++++ | ++++ | +++ |
| 16 | ++++ | ++++ | ++++ |
| 17 | +++ | +++ | +++ |
| 27 | ++++ | ++++ | ++++ |
| 31 | ++++ | | |
| 37 | ++++ | ++++ | ++++ |
| 47 | +++ | +++ | |
| 49 | ++++ | ++++ | |
| 51 | +++ | ++++ | |

++++ stands for mean IC50 ≦ 0.5 µM
+++ stands for mean IC50 between 0.5 µM and 2 µM From the given results it can clearly be seen that the compounds of the present invention display potent inhibition of Tie-2. Even more surprisingly, appropriate modifications produce compounds which display a stronger inhibition of both Tie-2 and VEGF-R2, wherein the respective inhibition of either Tie2 or VEGFR-2 can be tuned: such pharmacological profiles are highly desirable not only for treating diseases of dysregulated vascular growth or diseases which are accompanied with dysregulated vascular growth, in particular solid tumours and metastases thereof, but for treating non-oncological diseases of dysregulated vascular growth or non-oncological diseases which are accompanied with dysregulated vascular growth, such as retinopathy, other angiogenesis dependent diseases of the eye, in particular cornea transplant rejection or age-related macular degeneration, rheumatoid arthritis, and other inflammatory diseases associated with angiogenesis, in particular psoriasis, delayed type hypersensitivity, contact dermatitis, asthma, multiple sclerosis, restenosis, pulmonary hypertension, stroke, and diseases of the bowel, diseases such as coronary and peripheral artery disease, wherein treatment of the said non-oncological diseases are preferably accomplished with less side-effects than in the treatment of oncological diseases.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 050751775, filed Jan. 24, 2005 and U.S. Provisional Application Ser. No. 60/647,407, filed Jan. 28, 2005, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula (I):

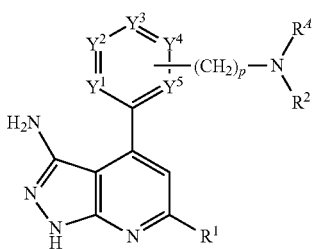

I wherein:
$R^1$ stands for $C_1$-$C_6$-alkyl, $C_2$-$C_6$-alkenyl, $C_2$-$C_6$-alkynyl, $C_3$-$C_{10}$-cycloalkyl, $C_3$-$C_{10}$-heterocycloalkyl, aryl or heteroaryl optionally being substituted one or more times, the same way or differently with K, wherein the $C_3$-$C_{10}$-heterocycloalkyl is at least once interrupted by a nitrogen, oxygen and/or sulfur and wherein the $C_3$-$C_{10}$-cycloalkyl ring and/or $C_3$-$C_{10}$-heterocycloalkyl ring is optionally interrupted one or more times, the same or differently with a group —C(O)—, —S(O)— or —S(O)$_2$— and wherein the $C_3$-$C_{10}$-cycloalkyl ring and/or $C_3$-$C_{10}$-heterocycloalkyl ring optionally contains one or more double bonds, K stands for halogen, hydroxy or —OR$^3$ or —NR$^5$R$^6$ or for $C_3$-$C_{10}$-cycloalkyl, $C_3$-$C_{10}$-heterocycloalkyl, aryl or heteroaryl optionally substituted one or more times, the same way or differently with L, wherein the $C_3$-$C_{10}$-heterocycloalkyl is at least one time interrupted by nitrogen, oxygen and/or sulfur and wherein the $C_3$-$C_{10}$-cycloalkyl ring and/or $C_3$-$C_{10}$-heterocycloalkyl ring is optionally interrupted one or more times, the same or differently with a group —C(O)—, —S(O)— or —S(O)$_2$— and wherein the $C_3$-$C_{10}$-cycloalkyl ring and/or $C_3$-$C_{10}$-heterocycloalkyl ring optionally contains one or more double bonds, L stands for —C(O)R$^4$ or —NR$^5$R$^6$ or for $C_1$-$C_6$-alkyl optionally substituted one or more times, the same way or differently with halogen, hydroxy, cyano, nitro or the group —NR$^5$R$^6$ or —C(O)R$^4$, $R^A$ stands for hydrogen or $C_1$-$C_6$-alkyl optionally substituted one or more times, the same way or differently with halogen, hydroxy, cyano, nitro or the group —NR$^5$R$^6$ or —C(O)R$^4$, $R^2$ stands for —C(O)—NR$^7$R$^{7a}$, —S(O)$_2$—R$^7$, —S(O)$_2$NR$^7$R$^{7a}$, —S(O)(NH)R$^7$, —C(O)R$^7$ or —C(O)OR$^7$, $R^3$ stands for $C_1$-$C_6$-alkyl, aryl or —(CH$_2$)$_n$-aryl, wherein $C_1$-$C_6$-alkyl, aryl or —(CH$_2$)$_n$-aryl is optionally substituted one or more times, the same way or differently with $C_1$-$C_6$-alkyl, $C_1$-$C_6$-alkoxy, halogen, hydroxy, cyano, nitro or the group —NR$^5$R$^6$ or —C(O)R$^4$, $R^4$ stands for hydrogen, hydroxy, $C_1$-$C_6$-alkyl, $C_1$-$C_6$-haloalkyl, $C_1$-$C_6$-alkoxy or the group —NR$^5$R$^6$, $R^5$ and $R^6$ independently from one another stand for hydrogen, $C_1$-$C_6$-alkyl, aryl, —(CH$_2$)$_n$-aryl, or —C(O)R$^4$, wherein $C_1$-$C_6$-alkyl or aryl is optionally substituted one or more times, the same way or differently with halogen, hydroxy, cyano, nitro or the group —NR$^7$R$^{7a}$ or —C(O)R$^4$, or $R^5$ and $R^6$ together with the nitrogen atom to which they are attached, form a 3 to 10 membered heterocycloalkyl ring, wherein the heterocycloalkyl ring is at least one time interrupted by nitrogen, oxygen and/or sulfur and is optionally interrupted one or more times, the same way or differently with —C(O)—, —S(O)— and/or —S(O)$_2$— and optionally contains one or more double bonds, $R^7$ and $R^{7a}$ independently from one another stand for hydrogen, $C_1$-$C_6$-alkyl, $C_3$-$C_{10}$-cycloalkyl, $C_3$-$C_{10}$-heterocycloalkyl, aryl or heteroaryl, wherein $C_1$-$C_6$-alkyl, $C_3$-$C_{10}$-cycloalkyl, $C_3$-$C_{10}$-heterocycloalkyl, aryl or heteroaryl is optionally substituted one or more times, the same way or differently with M, wherein the $C_3$-$C_{10}$-heterocycloalkyl is at least one time interrupted by nitrogen, oxygen and/or sulfur and wherein the $C_3$-$C_{10}$-cycloalkyl ring and/or $C_3$-$C_{10}$-heterocycloalkyl ring is optionally interrupted one or more times, the same way or differently with —C(O)—, —S(O)— or —S(O)$_2$— and wherein the $C_3$-$C_{10}$-cycloalkyl ring and/or $C_3$-$C_{10}$-heterocycloalkyl ring optionally contains one or more double bonds, or $R^7$ and $R^{7a}$ together with the nitrogen atom to which they are attached, form a 3 to 10 membered heterocycloalkyl ring, wherein the heterocycloalkyl ring is at least one time interrupted by nitrogen, oxygen and/or sulfur and is optionally interrupted one or more times, the same way or differently with —C(O)—, —S(O)— or —S(O)$_2$— and optionally contains one or more double bonds, M stands for cyano, halogen, hydroxy, nitro or for $C_1$-$C_6$-alkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-haloalkyl, aryl, $C_3$-$C_{10}$-heteroaryl, —(CH$_2$)$_m$-phenyl or —(CH$_2$)$_m$—O—(CH$_2$)$_q$ phenyl, wherein $C_1$-$C_6$-alkyl, $C_2$-$C_6$-alkenyl, $C_2$-$C_6$-alkynyl, $C_1$-$C_6$-alkoxy, aryl, $C_3$-$C_{10}$-heteroaryl, —(CH$_2$)$_m$-phenyl or —(CH$_2$)$_m$—O—(CH$_2$)$_q$phenyl is optionally substituted one or more times, the same way or differently with amino, cyano, halogen, hydroxy, nitro, $C_1$-$C_6$-alkyl, $C_1$-$C_6$-alkoxy, $C_1$-$C_6$-haloalkoxy, $C_1$-$C_6$-haloalkyl, —(CH$_2$)$_m$-phenyl or —(CH$_2$)$_m$—O—(CH$_2$)$_q$phenyl, $Y^1, Y^2, Y^3,$
$Y^4$ and $Y^5$ independently from each other stand for —CH═, or —CZ═, Z stands for cyano, nitro, halogen, hydroxy or —NR$^5$R$^6$, —OR$^3$, —C(O)R$^7$, —C(O)OR$^7$, —C(O)NR$^7$R$^{7a}$, —S(O)R$^7$ or —S(O)$_2$R$^7$ or for $C_1$-$C_6$-alkyl, $C_2$-$C_6$-alkenyl, $C_2$-$C_6$-alkynyl or $C_3$-$C_{10}$-cycloalkyl, wherein the $C_1$-$C_6$-alkyl, $C_2$-$C_6$-alkenyl, $C_2$-$C_6$-alkynyl or $C_3$-$C_{10}$-cycloalkyl is optionally substituted one or more times, the same way or different with cyano, nitro, halogen, hydroxy, —OR$^3$ or —NR$^5$, R$^6$, m stands for an integer of 0, 1, 2, 3, or 4,
n stands for an integer of 0, 1, 2, 3, or 4,
p stands for an integer of 0, 1, 2, 3, or 4, and
q stands for an integer of 0, 1, 2, 3, or 4, or an isomer, diastereomer, enantiomer, or salt thereof.

2. A compound according to claim 1, wherein:

R$^1$ stands for $C_1$-$C_6$-alkyl, $C_2$-$C_6$-alkenyl, $C_2$-$C_6$-alkynyl, $C_3$-$C_{10}$-cycloalkyl, $C_3$-$C_{10}$-heterocycloalkyl, aryl or heteroaryl optionally being substituted one or more times, the same way or differently with K, wherein the $C_3$-$C_{10}$-heterocycloalkyl is at least once interrupted by nitrogen, oxygen and/or sulfur and wherein the $C_3$-$C_{10}$-cycloalkyl ring and/or $C_3$-$C_{10}$-heterocycloalkyl ring is optionally interrupted one or more times, the same or differently with —C(O)—, —S(O)— or —S(O)$_2$— and wherein the $C_3$-$C_{10}$-cycloalkyl ring and/or $C_3$-$C_{10}$-heterocycloalkyl ring optionally contains one or more double bonds, K stands for halogen, hydroxy or —OR$^3$ or —NR$^5$R$^6$ or for $C_3$-$C_{10}$-cycloalkyl, $C_3$-$C_{10}$-heterocycloalkyl, aryl or heteroaryl optionally being substituted one or more times, the same way or differently with L, wherein the $C_3$-$C_{10}$-heterocycloalkyl is at least one time interrupted by nitrogen, oxygen and/or sulfur and wherein the $C_3$-$C_{10}$-cycloalkyl ring and/or $C_3$-$C_{10}$-heterocycloalkyl ring is optionally interrupted one or more times, the same or differently with —C(O)—, —S(O)— or —S(O)$_2$— and wherein the $C_3$-$C_{10}$-cycloalkyl ring and/or $C_3$-$C_{10}$-heterocycloalkyl ring optionally contains one or more double bonds, L stands for —C(O)R$^4$ or —NR$^5$R$^6$ or for $C_1$-$C_6$-alkyl optionally being substituted one or more times, the same way or differently with halogen, hydroxy, cyano, nitro or the group —NR$^5$R$^6$ or —C(O)R$^4$, R$^4$ stands for hydrogen or $C_1$-$C_6$-alkyl optionally being substituted one or more times, the same way or differently with halogen, hydroxy, cyano, nitro or the group —NR$^5$R$^6$ or —C(O)R$^4$, R$^2$ stands for —C(O)—NR$^7$R$^{7a}$, —S(O)$_2$—R$^7$, —S(O)$_2$NR$^7$R$^{7a}$, —S(O)(NH)R$^7$, —C(O)R$^7$ or —C(O)OR$^7$, R$^3$ stands for $C_1$-$C_6$-alkyl, aryl or —(CH$_2$)$_n$-aryl, wherein $C_1$-$C_6$-alkyl, aryl or —(CH$_2$)$_n$-aryl is optionally substituted one or more times, the same way or differently with $C_1$-$C_6$-alkyl, $C_1$-$C_6$-alkoxy, halogen, hydroxy, cyano, nitro or the group —NR$^5$R$^6$ or —C(O)R$^4$, R$^4$ stands for hydrogen, hydroxy, $C_1$-$C_6$-alkyl, $C_1$-$C_6$-haloalkyl, $C_1$-$C_6$-alkoxy or the group —NR$^5$R$^6$, R$^5$ and R$^6$ independently from one another stand for hydrogen, $C_1$-$C_6$-alkyl, aryl, —(CH$_2$)$_n$-aryl, or for a group —C(O)R$^4$, wherein $C_1$-$C_6$-alkyl or aryl is optionally substituted one or more times, the same way or differently with halogen, hydroxy, cyano, nitro or the group —NR$^7$R$^{7a}$ or —C(O)R$^4$, or R$^5$ and R$^6$ together with the nitrogen atom to which they are attached, form a 3 to 10 membered heterocycloalkyl ring, wherein the heterocycloalkyl ring is at least one time interrupted by nitrogen, oxygen and/or sulfur and is optionally interrupted one or more times, the same way or differently with a group —C(O)—, —S(O)— and/or —S(O)$_2$— and optionally contains one or more double bonds, R$^7$ and R$^{7a}$ independently from one another stand for hydrogen, $C_1$-$C_6$-alkyl, $C_3$-$C_{10}$-cycloalkyl, $C_3$-$C_{10}$-heterocycloalkyl, aryl or heteroaryl, wherein $C_1$-$C_6$-alkyl, $C_3$-$C_{10}$-cycloalkyl, $C_3$-$C_{10}$-heterocycloalkyl, aryl or heteroaryl is optionally substituted one or more times, the same way or differently with M, wherein the $C_3$-$C_{10}$-heterocycloalkyl is at least one time interrupted by nitrogen, oxygen and/or sulfur and wherein the $C_3$-$C_{10}$-cycloalkyl ring and/or $C_3$-$C_{10}$-heterocycloalkyl ring is optionally interrupted one or more times, the same way or differently with a group —C(O)—, —S(O)— or —S(O)$_2$— and wherein the $C_3$-$C_{10}$cycloalkyl ring and/or $C_3$-$C_{10}$-heterocycloalkyl ring optionally contains one or more double bonds, or R$^7$ and R$^{7a}$ together with the nitrogen atom to which they are attached, form a 3 to 10 membered heterocycloalkyl ring, wherein the heterocycloalkyl ring is at least one time interrupted by nitrogen, oxygen and/or sulfur and is optionally interrupted one or more times, the same way or differently with a group —C(O)—, —S(O)— or —S(O)$_2$— and optionally contains one or more double bonds, M stands for cyano, halogen, hydroxy, nitro or for $C_1$-$C_6$-alkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-haloalkyl, aryl, $C_3$-$C_{10}$-heteroaryl, —(CH$_2$)$_m$-phenyl or —(CH$_2$)$_m$—O—(CH$_2$)$_q$ phenyl, wherein $C_1$-$C_6$-alkyl, $C_2$-$C_6$-alkenyl, $C_2$-$C_6$-alkynyl, $C_1$-$C_6$-alkoxy, aryl, $C_3$-$C_{10}$-heteroaryl, —(CH$_2$)$_m$-phenyl or —(CH$_2$)$_m$—O—(CH$_2$)$_q$phenyl is optionally substituted one or more times, the same way or differently with amino, cyano, halogen, hydroxy, nitro, $C_1$-$C_6$-alkyl, $C_1$-$C_6$-alkoxy, $C_1$-$C_6$-haloalkoxy, $C_1$-$C_6$-haloalkyl, —(CH$_2$)$_m$-phenyl or —(CH$_2$)$_m$—O—(CH$_2$)$_q$phenyl, the structural moiety:

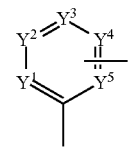

is one of the following moieties:

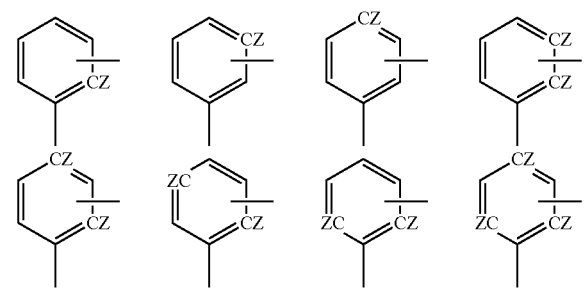

-continued

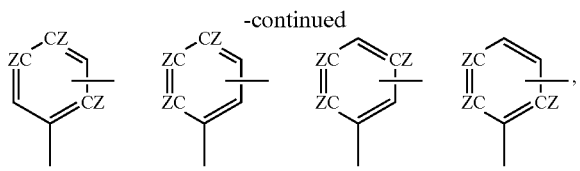

wherein
- Z stands for cyano, nitro, halogen, hydroxy or —$NR^5R^6$, —$OR^3$, —$C(O)R^7$, —$C(O)OR^7$, —$C(O)NR^7R^{7a}$, —$S(O)R^7$ or —$S(O)_2R^7$ or for $C_1$-$C_6$-alkyl, $C_2$-$C_6$-alkenyl, $C_2$-$C_6$-alkynyl or $C_3$-$C_{10}$-cycloalkyl, wherein the $C_1$-$C_6$-alkyl, $C_2$-$C_6$-alkenyl, $C_2$-$C_6$-alkynyl or $C_3$-$C_{10}$-cycloalkyl is optionally substituted one or more times, the same way or different with cyano, nitro, halogen, hydroxy, —$OR^3$ or —$NR^5R^6$,
- m stands for an integer of 0, 1, 2, 3, or 4,
- n stands for an integer of 0, 1, 2, 3, or 4,
- P stands for an integer of 0, 1, 2, 3, or 4, and
- q stands for an integer of 0, 1, 2, 3, or 4, or a
solvate, hydrate, isomer, diastereomer, enantiomer or salt thereof.

3. A compound according to claim 1, wherein:
- $R^1$ stands for $C_1$-$C_6$-alkyl, $C_2$-$C_6$-alkenyl, $C_2$-$C_6$-alkynyl, $C_3$-$C_{10}$-cycloalkyl, aryl or heteroaryl optionally being substituted one or more times, the same way or differently with K,
- K stands for halogen, hydroxy or stands for morpholinyl, piperazinyl, piperidinyl, pyrrolidinyl or phenoxy optionally substituted with L,
- L stands for $C_1$-$C_6$-alkyl or —$C(O)O$—$C_1$-$C_6$ alkyl, wherein the $C_1$-$C_6$-alkyl or —$C(O)O$—$C_1$-$C_6$ alkyl is optionally substituted one or more times, the same way or differently with halogen,
- $R^A$ stands for hydrogen or $C_1$-$C_6$-alkyl optionally being substituted one or more times, the same way or differently with halogen, hydroxy, cyano, nitro or the group —$NR^5R^6$ or —$C(O)R^4$,
- $R^2$ stands for —$C(O)$—$NR^7R^{7a}$, —$S(O)_2$—$R^7$, —$S(O)_2NR^7R^{7a}$, —$S(O)(NH)R^7$, —$C(O)R^7$ or —$C(O)OR^7$,
- $R^3$ stands for $C_1$-$C_6$-alkyl, aryl or —$(CH_2)_n$-aryl, wherein $C_1$-$C_6$-alkyl, aryl or —$(CH_2)_n$-aryl is optionally substituted one or more times, the same way or differently with $C_1$-$C_6$-alkyl, $C_1$-$C_6$-alkoxy, halogen, hydroxy, cyano, nitro or the group —$NR^5R^6$ or —$C(O)R^4$,
- $R^4$ stands for hydrogen, hydroxy, $C_1$-$C_6$-alkyl, $C_1$-$C_6$-haloalkyl, $C_1$-$C_6$-alkoxy or the group —$NR^5R^6$,
- $R^5$ and $R^6$ independently from one another stand for hydrogen, $C_1$-$C_6$-alkyl, aryl or for a group —$C(O)R^4$, wherein $C_1$-$C_6$-alkyl or aryl is optionally substituted one or more times, the same way or differently with halogen, hydroxy, cyano, nitro or the group —$NR^7R^{7a}$ or —$C(O)R^4$,
- $R^7$ and $R^{7a}$ independently from one another stand for hydrogen, $C_1$-$C_6$-alkyl, $C_3$-$C_{10}$-cycloalkyl, $C_3$-$C_{10}$-heterocycloalkyl, aryl or heteroaryl, wherein $C_1$-$C_6$-alkyl, $C_3$-$C_{10}$-cycloalkyl, $C_3$-$C_{10}$-heterocycloalkyl, aryl or heteroaryl optionally being substituted one or more times, the same way or differently with M,
- M stands for cyano, halogen, hydroxy, nitro or for $C_1$-$C_6$-alkyl, $C_2$-$C_6$-alkenyl, $C_2$-$C_6$-alkynyl, $C_1$-$C_6$-alkoxy, aryl, $C_3$-$C_{10}$-heteroaryl, —$(CH_2)_m$-phenyl or —$(CH_2)_m$—O—$(CH_2)_q$phenyl, wherein $C_1$-$C_6$-alkyl, $C_2$-$C_6$-alkenyl, $C_2$-$C_6$-alkynyl, $C_1$-$C_6$-alkoxy, aryl, $C_3$-$C_{10}$-heteroaryl, —$(CH_2)_m$-phenyl or —$(CH_2)_m$—O—$(CH_2)_q$phenyl is optionally substituted one or more times, the same way or differently with amino, cyano, halogen, hydroxy, nitro, or $C_1$-$C_6$-alkoxy, the structural moiety:

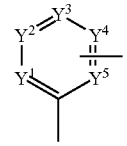

is one of the following moieties:

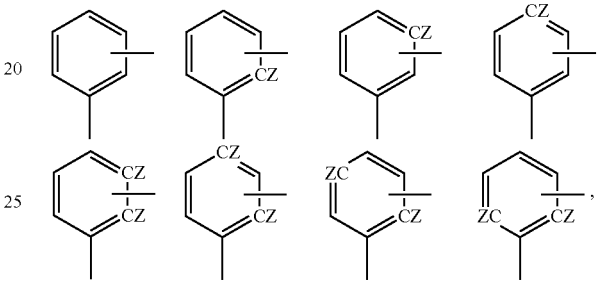

wherein
- Z stands for cyano, nitro, halogen, hydroxy or —$NR^5R^6$, —$OR^3$, —$C(O)R^7$, —$C(O)OR^7$, —$C(O)NR^7R^{7a}$, —$S(O)R^7$ or —$S(O)_2R^7$ or for $C_1$-$C_6$-alkyl, $C_2$-$C_6$-alkenyl, $C_2$-$C_6$-alkynyl or $C_3$-$C_{10}$-cycloalkyl, wherein the $C_1$-$C_6$-alkyl, $C_2$-$C_6$-alkenyl, $C_2$-$C_6$-alkynyl or $C_3$-$C_{10}$-cycloalkyl is optionally substituted one or more times, the same way or different with cyano, nitro, halogen, hydroxy, —$OR^3$ or —$NR^5R^6$,
- m stands for an integer of 0, 1, 2, 3, or 4,
- n stands for an integer of 0, 1, 2, 3, or 4,
- p stands for an integer of 0, 1, 2, 3, or 4, and
- q stands for an integer of 0, 1, 2, 3, or 4, or an isomer, diastereomer, enantiomer, or salt thereof.

4. A compound according to claim 1, wherein:
- $R^1$ stands for $C_1$-$C_6$-alkyl substituted with K, $C_3$-$C_{10}$-cycloalkyl substituted with K, unsubstituted $C_1$-$C_6$-alkyl, or unsubstituted $C_3$-$C_{10}$-cycloalkyl,
- K stands for halogen, hydroxy or stands for morpholinyl, piperazinyl, piperidinyl or phenoxy,
- L stands for $C_1$-$C_6$-alkyl or —$C(O)O$—$C_1$-$C_6$-alkyl, wherein the $C_1$-$C_6$-alkyl or —$C(O)O$—$C_1$-$C_6$-alkyl is optionally substituted one or more times, the same way or differently with halogen,
- $R^A$ stands for hydrogen,
- $R^2$ stands for —$C(O)$—NH—$R^7$, —$S(O)_2$—$R^7$, or —$C(O)R^7$,
- $R^3$ stands for $C_1$-$C_6$-alkyl, aryl or —$(CH_2)_n$-aryl, wherein $C_1$-$C_6$-alkyl, aryl or —$(CH_2)_n$-aryl is optionally substituted one or more times, the same way or differently with $C_1$-$C_6$-alkyl, $C_1$-$C_6$-alkoxy, halogen, hydroxy, cyano, nitro or the group —$NR^5R^6$ or —$C(O)R^4$,
- $R^4$ stands for hydrogen, hydroxy, $C_1$-$C_6$-alkyl, $C_1$-$C_6$-haloalkyl, $C_1$-$C_6$-alkoxy or the group —$NR^5R^6$,
- $R^5$ and $R^6$ independently from one another stand for hydrogen, $C_1$-$C_6$-alkyl, aryl or for a group —$C(O)R^4$, wherein $C_1$-$C_6$-alkyl or aryl is optionally substituted one or more times, the same way or differently with halogen, hydroxy, cyano, nitro or the group —NR$^7$R$^{7a}$ or —C(O)R$^4$, R$^7$ and R$^{7a}$ independently from one another stand for C$_1$-C$_2$-alkyl, cyclopropyl, or phenyl, wherein the C$_1$-C$_2$-alkyl, cyclopropyl, or phenyl is optionally substituted one or more times, the same way or differently with M, M stands for cyano, halogen, hydroxy, nitro or for C$_1$-C$_6$-alkyl, C$_2$-C$_6$-alkenyl, C$_2$-C$_6$-alkynyl, C$_1$-C$_6$-alkoxy, aryl, C$_3$-C$_{10}$-heteroaryl, —(CH$_2$)$_m$-phenyl or —(CH$_2$)$_m$—O—(CH$_2$)$_q$phenyl, wherein C$_1$-C$_6$-alkyl, C$_2$-C$_6$-alkenyl, C$_2$-C$_6$-alkynyl, C$_1$-C$_6$-alkoxy, aryl, C$_3$-C$_{10}$-heteroaryl, —(CH$_2$)$_m$-phenyl or —(CH$_2$)$_m$—O—(CH$_2$)$_q$phenyl is optionally substituted one or more times, the same way or differently with amino, cyano, halogen, hydroxy, nitro, or C$_1$-C$_6$-alkoxy, the structural moiety:

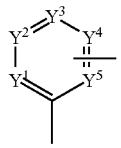

is one of the following moieties:

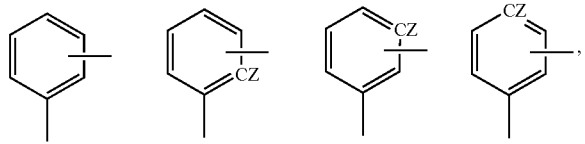

wherein

Z stands for cyano, nitro, halogen, hydroxy or —NR$^5$R$^6$, —OR$^3$, —C(O)R$^7$, —C(O)OR$^7$, —C(O)NR$^7$R$^{7a}$, —S(O)R$^7$ or —S(O)$_2$R$^7$ or for C$_1$-C$_6$-alkyl, C$_2$-C$_6$-alkenyl, C$_2$-C$_6$-alkynyl or C$_3$-C$_{10}$-cycloalkyl, wherein the C$_1$-C$_6$-alkyl, C$_2$-C$_6$-alkenyl, C$_2$-C$_6$-alkynyl or C$_3$-C$_{10}$-cycloalkyl is optionally substituted one or more times, the same way or different with cyano, nitro, halogen, hydroxy, —OR$^3$ or —NR$^5$R$^6$, m stands for an integer of 0, 1, 2, 3, or 4,
n stands for an integer of 0, 1, 2, 3, or 4,
p stands for an integer of 0, 1, 2, 3, or 4, and
q stands for an integer of 0, 1, 2, 3, or 4, or an isomer, diastereomer, enantiomer, or salt thereof.

5. A compound according to claim 1, wherein:
R$^1$ stands for C$_1$-C$_6$-alkyl substituted with K, C$_3$-C$_{10}$-cycloalkyl substituted with
K, unsubstituted C$_1$-C$_6$-alkyl, or unsubstituted C$_3$-C$_{10}$-cycloalkyl, K stands for halogen, hydroxy or stands for morpholinyl, piperazinyl, piperidinyl or phenoxy,
L stands for C$_1$-C$_6$-alkyl or —C(O)O—C$_1$-C$_6$ alkyl, wherein the C$_1$-C$_6$-alkyl or —C(O)O—C$_1$-C$_6$ alkyl is optionally substituted one or more times, the same way or differently with halogen,
R$^4$ stands for hydrogen,
R$^2$ stands for —C(O)—NH—R$^7$, —S(O)$_2$—R$^7$, or —C(O)R$^7$,
R$^7$ stands for C$_1$-C$_2$-alkyl, cyclopropyl, or phenyl, wherein the C$_1$-C$_2$-alkyl, cyclopropyl, or phenyl is optionally substituted one or more times, the same way or differently with M, M stands for cyano, halogen, hydroxy, nitro or for C$_1$-C$_6$-alkyl, C$_2$-C$_6$-alkenyl, C$_2$-C$_6$-alkynyl, C$_1$-C$_6$-alkoxy, aryl, C$_3$-C$_{10}$-heteroaryl, —(CH$_2$)$_m$-phenyl or —(CH$_2$)$_m$—O—(CH$_2$)$_q$phenyl, wherein C$_1$-C$_6$-alkyl, C$_2$-C$_6$-alkenyl, C$_2$-C$_6$-alkynyl, C$_1$-C$_6$-alkoxy, aryl, C$_3$-C$_{10}$-heteroaryl, —(CH$_2$)$_m$-phenyl or —(CH$_2$)$_m$—O—(CH$_2$)$_q$phenyl is optionally substituted one or more times, the same way or differently with amino, cyano, halogen, hydroxy, nitro, or C$_1$-C$_6$-alkoxy, the structural moiety:

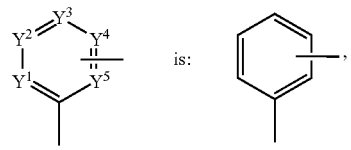

m stands for 0 or 1,
n stands for 0 or 1,
p stands for 0, and
q stands for 0 or 1, or an isomer, diastereomer, enantiomer, or salt thereof.

6. A compound according to claim 1, wherein:
R$^1$ stands for tert-butyl, isopropyl or cyclopropyl,
R$^4$ stands for hydrogen,
R$^2$ stands for —C(O)—NH—R$^7$, —S(O)$_2$—R$^7$, or —C(O)R$^7$,
R$^7$ stands for C$_1$-C$_2$-alkyl, cyclopropyl, or phenyl, wherein the C$_1$-C$_2$-alkyl, cyclopropyl, or phenyl is optionally substituted one or more times, the same way or differently with M, M stands for phenyl, hydroxyl, cyano, halogen, nitro, C$_1$-C$_2$-haloalkyl, C$_1$-C$_2$-alkoxy, C$_1$-C$_2$-haloalkoxy, —(CH$_2$)$_m$-phenyl or —(CH$_2$)$_m$—O—(CH$_2$)$_q$phenyl, or for C$_1$-C$_2$-alkyl, wherein the phenyl is optionally substituted one or more times, the same way or different with hydroxy, cyano, halogen, nitro, C$_1$-C$_2$-haloalkyl, C$_1$-C$_2$-alkoxy, C$_1$-C$_2$-haloalkoxy, or C$_1$-C$_2$-alkyl, the structural moiety:

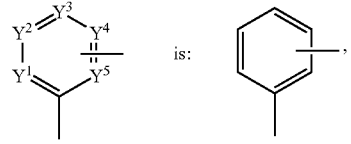

m stands for 0 or 1,
n stands for 0 or 1,
q stands for 0 or 1, and
p stands for 0, or an isomer, diastereomer, enantiomer, or salt thereof.

7. A compound, which is selected from the group consisting of:
1-[4-(3-amino-6-tert-butyl-1H-pyrazolo[3,4-b]pyridin-4-yl)-phenyl]-3-phenyl-urea;
N-[4-(3-amino-6-tert-butyl-1H-pyrazolo[3,4-b]pyridin-4-yl)-phenyl]-benzenesulfonamide;
1-[4-(3-amino-6-tert-butyl-1H-pyrazolo[3,4-b]pyridin-4-yl)-phenyl]-3-(3-fluoro-phenyl)-urea;
1-[4-(3-amino-6-tert-butyl-1H-pyrazolo[3,4-b]pyridin-4-yl)-phenyl]-3-(2-fluoro-phenyl)-urea;
1-[4-(3-amino-6-tert-butyl-1H-pyrazolo[3,4-b]pyridin-4-yl)-phenyl]-3-(2,5-difluoro-phenyl)-urea;

1-[4-(3-amino-6-tert-butyl-1H-pyrazolo[3,4-b]pyridin-4-yl)-phenyl]-3-(3,4-difluoro-phenyl)-urea;
1-[4-(3-amino-6-tert-butyl-1H-pyrazolo[3,4-b]pyridin-4-yl)-phenyl]-3-naphthalen-1-yl-urea;
1-[4-(3-amino-6-tert-butyl-1H-pyrazolo[3,4-b]pyridin-4-yl)-phenyl]-3-naphthalen-2-yl-urea;
1-[4-(3-amino-6-tert-butyl-1H-pyrazolo[3,4-b]pyridin-4-yl)-phenyl]-3-m-tolyl-urea;
1-[4-(3-amino-6-tert-butyl-1H-pyrazolo[3,4-b]pyridin-4-yl)-phenyl]-3-(2-nitro-phenyl)-urea;
1-[4-(3-amino-6-tert-butyl-1H-pyrazolo[3,4-b]pyridin-4-yl)-phenyl]-3-(2,4-difluoro-phenyl)-urea;
1-[4-(3-amino-6-tert-butyl-1H-pyrazolo[3,4-b]pyridin-4-yl)-phenyl]-3-(4-fluoro-phenyl)-urea;
1-[4-(3-amino-6-tert-butyl-1H-pyrazolo[3,4-b]pyridin-4-yl)-phenyl]-3-(4-cyano-phenyl)-urea;
1-[4-(3-amino-6-cyclopropyl-1H-pyrazolo[3,4-b]pyridin-4-yl)-phenyl]-3-phenyl-urea; 1-[4-(3-amino-6-cyclopropyl-1H-pyrazolo[3,4-b]pyridin-4-yl)-phenyl]-3-(2-fluoro-phenyl)-urea;
1-[4-(3-amino-6-isopropyl-1H-pyrazolo[3,4-b]pyridin-4-yl)-phenyl]-3-(3-trifluoromethyl-phenyl)-urea;
N-[4-(3-amino-6-tert-butyl-1H-pyrazolo[3,4-b]pyridin-4-yl)-phenyl]-4-methyl-benzamide;
1-[4-(3-amino-6-tert-butyl-1H-pyrazolo[3,4-b]pyridin-4-yl)-phenyl]-3-benzyl-urea;
1-[4-(3-amino-6-tert-butyl-1H-pyrazolo[3,4-b]pyridin-4-yl)-phenyl]-3-phenethyl-urea;
1-[4-(3-amino-6-tert-butyl-1H-pyrazolo[3,4-b]pyridin-4-yl)-phenyl]-3-isopropyl-urea;
1-[4-(3-amino-6-tert-butyl-1H-pyrazolo[3,4-b]pyridin-4-yl)-phenyl]-3-cyclopentyl-urea;
1-[4-(3-amino-6-tert-butyl-1H-pyrazolo[3,4-b]pyridin-4-yl)-phenyl]-3-cyclohexyl-urea;
1-[4-(3-amino-6-tert-butyl-1H-pyrazolo-[3,4-b]pyridin-4-yl)-phenyl]-3-(3-ethyl-phenyl)-urea;
1-[4-(3-amino-6-tert-butyl-1H-pyrazolo[3,4-b]pyridin-4-yl)-phenyl]-3-(2-fluoro-3-trifluoromethyl-phenyl)-urea; 1-[4-(3-amino-6-tert-butyl-1H-pyrazolo-[3,4-b]pyridin-4-yl)-phenyl]-3-o-tolyl-urea; 1-[4-(3-amino-6-tert-butyl-1H-pyrazolo-[3,4-b]pyridin-4-yl)-phenyl]-3-(3-benzyl-phenyl)-urea;
1-[4-(3-amino-6-tert-butyl-1H-pyrazolo-[3,4-b]pyridin-4-yl)-phenyl]-3-(3-trifluoro-methyl-phenyl)-urea;
1-[4-(3-amino-6-tert-butyl-1H-pyrazolo-[3,4-b]pyridin-4-yl)-phenyl]-3-(3-cyano-phenyl)-urea;
1-[4-(3-amino-6-tert-butyl-1H-pyrazolo-[3,4-b]pyridin-4-yl)-phenyl]-3-p-tolyl-urea;
1-[4-(3-amino-6-tert-butyl-1H-pyrazolo-[3,4-b]pyridin-4-yl)-phenyl]-3-(3-methoxy-phenyl)-urea;
1-[4-(3-amino-6-tert-butyl-1H-pyrazolo[3,4-b]pyridin-4-yl)-phenyl]-3-(2-fluoro-5-methyl-phenyl)-urea;
1-[4-(3-amino-6-tert-butyl-1H-pyrazolo-[3,4-b]pyridin-4-yl)-phenyl]-3-(3-phenoxy-phenyl)-urea;
1-[4-(3-amino-6-tert-butyl-1H-pyrazolo-[3,4-b]pyridin-4-yl)-phenyl]-3-(2-methoxy-5-methyl-phenyl)-urea;
1-[4-(3-amino-6-tert-butyl-1H-pyrazolo-[3,4-b]pyridin-4-yl)-phenyl]-3-(3-nitro-phenyl)-urea;
1-[4-(3-amino-6-tert-butyl-1H-pyrazolo[3,4-b]pyridin-4-yl)-phenyl]-3-(2-chloro-5-trifluoromethyl-phenyl)-urea;
1-[4-(3-amino-6-tert-butyl-1H-pyrazolo-[3,4-b]pyridin-4-yl)-phenyl]-3-biphenyl-4-yl-urea;
1-[4-(3-amino-6-tert-butyl-1H-pyrazolo[3,4-b]pyridin-4-yl)-phenyl]-3-(2-fluoro-5-trifluoromethyl-phenyl)-urea;
1-[4-(3-amino-6-tert-butyl-1H-pyrazolo-[3,4-b]pyridin-4-yl)-phenyl]-3-(3-ethoxy-phenyl)-urea;
1-[4-(3-amino-6-tert-butyl-1H-pyrazolo-[3,4-b]pyridin-4-yl)-phenyl]-3-(3,5-dimethyl-phenyl)-urea;
1-[4-(3-amino-6-tert-butyl-1H-pyrazolo-[3,4-b]pyridin-4-yl)-phenyl]-3-(3,4-dimethyl-phenyl)-urea;
1-[4-(3-amino-6-tert-butyl-1H-pyrazolo-[3,4-b]pyridin-4-yl)-phenyl]-3-(2,3-dimethyl-phenyl)-urea;
1-[4-(3-amino-6-tert-butyl-1H-pyrazolo-[3,4-b]pyridin-4-yl)-phenyl]-3-(2,5-dimethyl-phenyl)-urea;
1-[4-(3-amino-6-tert-butyl-1H-pyrazolo[3,4-b]pyridin-4-yl)-phenyl]-3-((S)-1-phenyl-ethyl)-urea;
1-[4-(3-amino-6-tert-butyl-1H-pyrazolo[3,4-b]pyridin-4-yl)-phenyl]-3-((R)-1-phenyl-ethyl)-urea;
1-[4-(3-amino-6-cyclo-propyl-1H-pyrazolo-[3,4-b]pyridin-4-yl)-phenyl]-3-m-tolyl-urea;
N-[4-(3-amino-6-tert-butyl-1H-pyrazolo[3,4-b]pyridin-4-yl)-phenyl]-3-methoxy-benzamide;
N-[4-(3-amino-6-tert-butyl-1H-pyrazolo[3,4-b]pyridin-4-yl)-phenyl]-2-phenyl-acetamide;
N-[4-(3-amino-6-tert-butyl-1H-pyrazolo[3,4-b]pyridin-4-yl)-phenyl]-2-o-tolyl-acetamide; 1-phenyl-cyclopropanecarboxylic acid [4-(3-amino-6-tert-butyl-1H-pyrazolo[3,4-b]pyridin-4-yl)-phenyl]-amide;
N-[4-(3-amino-6-tert-butyl-1H-pyrazolo[3,4-b]pyridin-4-yl)-phenyl]-2-(3-methoxy-phenyl)-acetamide;
N-[4-(3-amino-6-tert-butyl-1H-pyrazolo[3,4-b]pyridin-4-yl)-phenyl]-2-phenyl-isobutyramide;
N-[4-(3-amino-6-tert-butyl-1H-pyrazolo[3,4-b]pyridin-4-yl)-phenyl]-2-(4-chloro-phenyl)-acetamide;
N-[4-(3-amino-6-tert-butyl-1H-pyrazolo[3,4-b]pyridin-4-yl)-phenyl]-2-(4-methoxy-phenyl)-acetamide;
N-[4-(3-amino-6-tert-butyl-1H-pyrazolo[3,4-b]pyridin-4-yl)-phenyl]-3-methyl-benzamide;
N-[4-(3-amino-6-tert-butyl-1H-pyrazolo[3,4-b]pyridin-4-yl)-phenyl]-2-phenyl-butyramide;
N-[4-(3-amino-6-tert-butyl-1H-pyrazolo-[3,4-b]pyridin-4-yl)-phenyl]-3,4-difluoro-benzenesulfonamide;
N-[4-(3-amino-6-tert-butyl-1H-pyrazolo-[3,4-b]pyridin-4-yl)-phenyl]-3-nitro-benzenesulfonamide;
N-[4-(3-amino-6-tert-butyl-1H-pyrazolo-[3,4-b]pyridin-4-yl)-phenyl]-3-fluoro-benzenesulfonamide;
N-[4-(3-amino-6-tert-butyl-1H-pyrazolo-[3,4-b]pyridin-4-yl)-phenyl]-3,5-difluoro-benzenesulfonamide;
N-[4-(3-amino-6-tert-butyl-1H-pyrazolo-[3,4-b]pyridin-4-yl)-phenyl]-4-methyl-benzenesulfonamide;
N-[4-(3-amino-6-tert-butyl-1H-pyrazolo-[3,4-b]pyridin-4-yl)-phenyl]-3-methyl-benzenesulfonamide;
N-[4-(3-amino-6-tert-butyl-1H-pyrazolo-[3,4-b]pyridin-4-yl)-phenyl]-2,4-difluoro-benzenesulfonamide;
N-[4-(3-amino-6-cyclo-propyl-1H-pyrazolo-[3,4-b]pyridin-4-yl)-phenyl]-benzenesulfonamide;
N-[4-(3-amino-6-cyclo-propyl-1H-pyrazolo-[3,4-b]pyridin-4-yl)-phenyl]-3-nitro-benzenesulfonamide;
N-[4-(3-amino-6-cyclo-propyl-1H-pyrazolo-[3,4-b]pyridin-4-yl)-phenyl]-4-methyl-benzenesulfonamide; and
N-[4-(3-amino-6-cyclo-propyl-1H-pyrazolol-[3,4-b]pyridin-4-yl)-phenyl]-3-methyl-benzenesulfonamide.

8. A method of preparing a compound according to claim 1, comprising converting a compound of formula 6:

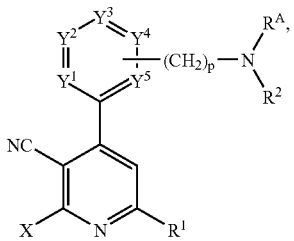     6 to a compound of formula (I):

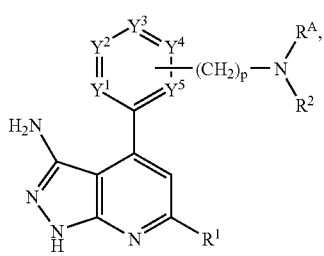     (I)

wherein X stands for halogen or perfluor-$C_1$-$C_4$-alkyl sulfonyl and $R^A$, $R^1$, $R^2$, $Y^1$, $Y^2$, $Y^3$, $Y^4$, $Y^5$ and p have the meaning as defined for the compound of formula (I).

9. A method according to claim 8, wherein said compound of formula 6 is prepared by conversion of a compound of formula 5:

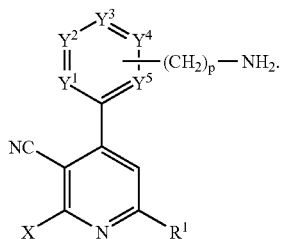     5

10. A method according to claim 9, wherein said compound of formula 5 is prepared by conversion of a compound of formula 4:

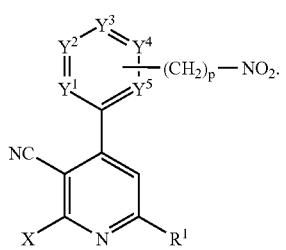     4

11. A method according to claim 10, wherein said compound of formula 4 is prepared by conversion of a compound of formula 3:

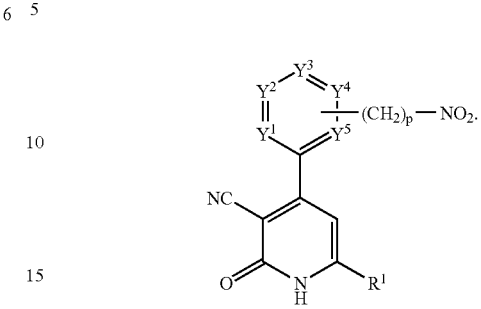     3

12. A method according to claim 11, wherein said compound of formula 3 is prepared from an aldehyde of formula 1:

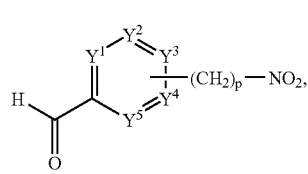     1 by allowing it to react with a methyl ketone of formula 2:

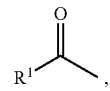     2 an alkyl cyanoacetate:

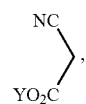

and an ammonium salt.

13. A method according to claim 8, wherein said compound of formula 6 is prepared by conversion of a compound of formula 10:

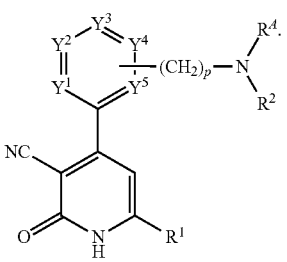     10

14. A method according to claim 13, wherein said compound of formula 10 is prepared by allowing an aldehyde of formula 7:

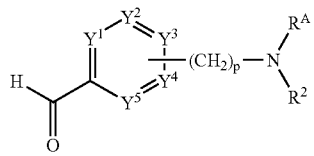

to react with a methyl ketone of formula 2:

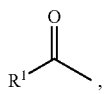

an alkyl cyanoacetate:

and an ammonium salt.

15. A method of preparing a compound according to claim 1, comprising converting a compound of formula 9:

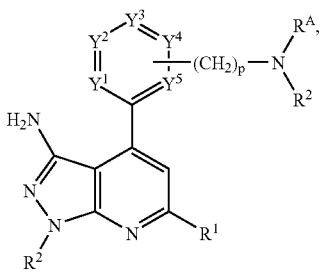

to a compound of formula (I):

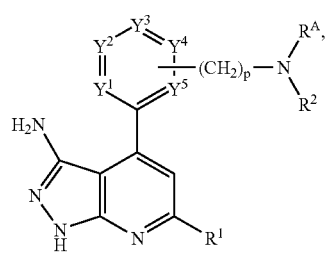

wherein X stands for halogen or perfluor-$C_1$-$C_4$-alkyl sulfonyl and $R^A$, $R^1$, $R^2$, $Y^1$, $Y^2$, $Y^3$, $Y^4$, $Y^5$ and p have the meaning as defined for the compound of formula (I).

16. A method according to claim 15, wherein said compound of formula 9 is prepared by converting a compound of formula 8:

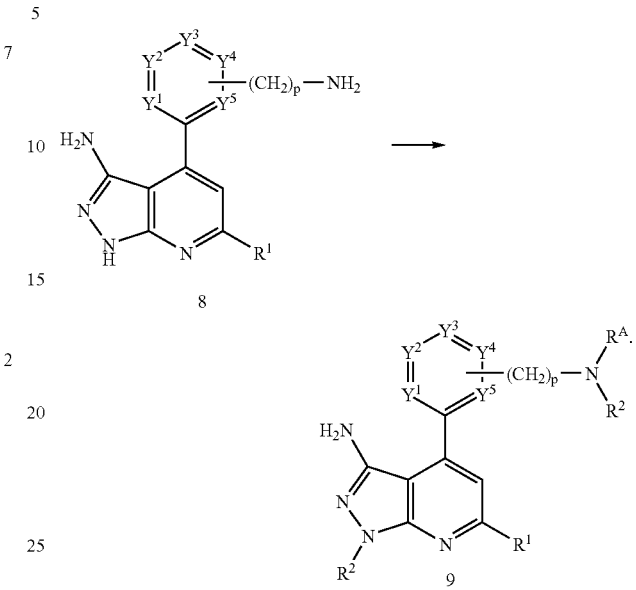

17. A pharmaceutical composition which comprises a compound of formula (I) according to claim 1, or a pharmaceutically acceptable salt or an in vivo hydrolysable ester thereof, and a pharmaceutically-acceptable diluent or carrier.

18. A compound according to claim 1, or a pharmaceutically acceptable salt thereof.

19. A compound according to claim 2, or a pharmaceutically acceptable salt thereof.

20. A compound according to claim 3, or a pharmaceutically acceptable salt thereof.

21. A compound according to claim 4, or a pharmaceutically acceptable salt thereof.

22. A compound according to claim 5, or a pharmaceutically acceptable salt thereof.

23. A compound according to claim 6, or a pharmaceutically acceptable salt thereof.

24. A compound according to claim 1, wherein:

$R^1$ stands for $C_1$-$C_6$-alkyl, $C_2$-$C_6$-alkenyl, $C_2$-$C_6$-alkynyl, $C_3$-$C_{10}$-cycloalkyl, or aryl optionally being substituted one or more times, the same way or differently with K, wherein the $C_3$-$C_{10}$-cycloalkyl ring is optionally interrupted one or more times, the same or differently with a group —C(O)—, —S(O)— or —S(O)$_2$— and wherein the $C_3$-$C_{10}$-cycloalkyl ring optionally contains one or more double bonds, K stands for halogen, hydroxy or —OR$^3$ or —NR$^5$R$^6$ or for $C_3$-$C_{10}$-cycloalkyl, $C_3$-$C_{10}$-heterocycloalkyl, aryl or heteroaryl optionally substituted one or more times, the same way or differently with L, wherein the $C_3$-$C_{10}$-heterocycloalkyl is at least one time interrupted by nitrogen, oxygen and/or sulfur and wherein the $C_3$-$C_{10}$-cycloalkyl ring and/or $C_3$-$C_{10}$-heterocycloalkyl ring is optionally interrupted one or more times, the same or differently with a group —C(O)—, —S(O)— or —S(O)$_2$— and wherein the $C_3$-$C_{10}$-cycloalkyl ring and/or $C_3$-$C_{10}$-heterocycloalkyl ring optionally contains one or more double bonds, L stands for —C(O)R$^4$ or —NR$^5$R$^6$ or for $C_1$-$C_6$-alkyl optionally substituted one or more times, the same way or differently with halogen, hydroxy, cyano, nitro or the group —$NR^5R^6$ or —$C(O)R^4$, $R^4$ stands for hydrogen or $C_1$-$C_6$-alkyl optionally substituted one or more times, the same way or differently with halogen, hydroxy, cyano, nitro or the group —$NR^5R^6$ or —$C(O)R^4$, $R^2$ stands for —$C(O)$—$NR^7R^{7a}$, —$S(O)_2$—$R^7$, —$S(O)_2NR^7R^{7a}$, —$S(O)(NH)R^7$, —$C(O)R^7$ or —$C(O)OR^7$, $R^3$ stands for $C_1$-$C_6$-alkyl, aryl or —$(CH_2)_n$-aryl, wherein $C_1$-$C_6$-alkyl, aryl or —$(CH_2)_n$-aryl is optionally substituted one or more times, the same way or differently with $C_1$-$C_6$-alkyl, $C_1$-$C_6$-alkoxy, halogen, hydroxy, cyano, nitro or the group —$NR^5R^6$ or —$C(O)R^4$, $R^4$ stands for hydrogen, hydroxy, $C_1$-$C_6$-alkyl, $C_1$-$C_6$-haloalkyl, $C_1$-$C_6$-alkoxy or the group —$NR^5R^6$, $R^5$ and $R^6$ independently from one another stand for hydrogen, $C_1$-$C_6$-alkyl, aryl, —$(CH_2)_n$-aryl, or —$C(O)R^4$, wherein $C_1$-$C_6$-alkyl or aryl is optionally substituted one or more times, the same way or differently with halogen, hydroxy, cyano, nitro or the group —$NR^7R^{7a}$ or —$C(O)R^4$, or $R^5$ and $R^6$ together with the nitrogen atom to which they are attached, form a 3 to 10 membered heterocycloalkyl ring, wherein the heterocycloalkyl ring is at least one time interrupted by nitrogen, oxygen and/or sulfur and is optionally interrupted one or more times, the same way or differently with —$C(O)$—, —$S(O)$— and/or —$S(O)_2$— and optionally contains one or more double bonds, $R^7$ and $R^{7a}$ independently from one another stand for hydrogen, $C_1$-$C_6$-alkyl, $C_3$-$C_{10}$-cycloalkyl, $C_3$-$C_{10}$-heterocycloalkyl, aryl or heteroaryl, wherein $C_1$-$C_6$-alkyl, $C_3$-$C_{10}$-cycloalkyl, $C_3$-$C_{10}$-heterocycloalkyl, aryl or heteroaryl is optionally substituted one or more times, the same way or differently with M, wherein the $C_3$-$C_{10}$-heterocycloalkyl is at least one time interrupted by nitrogen, oxygen and/or sulfur and wherein the $C_3$-$C_{10}$-cycloalkyl ring and/or $C_3$-$C_{10}$-heterocycloalkyl ring is optionally interrupted one or more times, the same way or differently with —$C(O)$—, —$S(O)$— or —$S(O)_2$— and wherein the $C_3$-$C_{10}$-cycloalkyl ring and/or $C_3$-$C_{10}$-heterocycloalkyl ring optionally contains one or more double bonds, or $R^7$ and $R^{7a}$ together with the nitrogen atom to which they are attached, form a 3 to 10 membered heterocycloalkyl ring, wherein the heterocycloalkyl ring is at least one time interrupted by nitrogen, oxygen and/or sulfur and is optionally interrupted one or more times, the same way or differently with —$C(O)$—, —$S(O)$— or —$S(O)_2$— and optionally contains one or more double bonds, M stands for cyano, halogen, hydroxy, nitro or for $C_1$-$C_6$-alkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-haloalkyl, aryl, $C_3$-$C_{10}$-heteroaryl, —$(CH_2)_m$-phenyl or —$(CH_2)_m$—O—$(CH_2)_q$phenyl, wherein $C_1$-$C_6$-alkyl, $C_2$-$C_6$-alkenyl, $C_2$-$C_6$-alkynyl, $C_1$-$C_6$-alkoxy, aryl, $C_3$-$C_{10}$-heteroaryl, —$(CH_2)_m$-phenyl or —$(CH_2)_m$—O—$(CH_2)_q$phenyl is optionally substituted one or more times, the same way or differently with amino, cyano, halogen, hydroxy, nitro, $C_1$-$C_6$-alkyl, $C_1$-$C_6$-alkoxy, $C_1$-$C_6$-haloalkoxy, $C_1$-$C_6$-haloalkyl, —$(CH_2)_m$-phenyl or —$(CH_2)_m$—O—$(CH_2)_q$phenyl, $Y^1, Y^2, Y^3$, $Y^4$ and $Y^5$ independently from each other stand for —$CH=$ or —$CZ=$, Z stands for cyano, nitro, halogen, hydroxy or —$NR^5R^6$, —$OR^3$, —$C(O)R^7$, —$C(O)OR^7$, —$C(O)NR^7R^{7a}$, —$S(O)R^7$ or —$S(O)_2R^7$ or for $C_1$-$C_6$-alkyl, $C_2$-$C_6$-alkenyl, $C_2$-$C_6$-alkynyl or $C_3$-$C_{10}$-cycloalkyl, wherein the $C_1$-$C_6$-alkyl, $C_2$-$C_6$-alkenyl, $C_2$-$C_6$-alkynyl or $C_3$-$C_{10}$-cycloalkyl is optionally substituted one or more times, the same way or different with cyano, nitro, halogen, hydroxy, —$OR^3$ or —$NR^5, R^6$, m stands for an integer of 0, 1, 2, 3, or 4, n stands for an integer of 0, 1, 2, 3, or 4, p stands for an integer of 0, 1, 2, 3, or 4, and q stands for an integer of 0, 1, 2, 3, or 4, or a pharmaceutically acceptable salt thereof.

25. A pharmaceutical composition which comprises a compound of claim 7, or a pharmaceutically acceptable salt or an in vivo hydrolysable ester thereof, and a pharmaceutically-acceptable diluent or carrier.

* * * * *